(12) United States Patent
Fujita et al.

(10) Patent No.: US 6,664,208 B1
(45) Date of Patent: Dec. 16, 2003

(54) MODIFIED ALUMINUM OXY COMPOUND, POLYMERIZATION CATALYST AND PROCESS FOR PRODUCING OLEFIN POLYMER AND ALKENYL AROMATIC HYDROCARBON POLYMER

(75) Inventors: Masayuki Fujita, Ichihara (JP); Masaaki Nabika, Ichihara (JP); Tatsuya Miyatake, Ichihara (JP); Tsuyoshi Watanabe, Ichihara (JP); Yoshinori Seki, Ichihara (JP); Nobuo Oi, Narashino (JP)

(73) Assignee: Sumitomo Chemical Company, Limited, Osaka (JP)

( * ) Notice: Subject to any disclaimer, the term of this patent is extended or adjusted under 35 U.S.C. 154(b) by 435 days.

(21) Appl. No.: 09/661,626

(22) Filed: Sep. 13, 2000

Related U.S. Application Data

(63) Continuation-in-part of application No. 09/391,662, filed on Sep. 7, 1999.

(51) Int. Cl.[7] .................................................. B01J 31/14
(52) U.S. Cl. ...................... 502/132; 502/103; 502/152; 502/156; 526/346; 526/160; 526/943; 526/124.5
(58) Field of Search ................................ 502/132, 152, 502/103, 156; 526/346, 160, 943, 124.5

(56) References Cited

U.S. PATENT DOCUMENTS

| | | |
|---|---|---|
| 4,542,199 A | 9/1985 | Kaminsky et al. |
| 4,990,640 A * | 2/1991 | Tsutsui et al. ............... 556/181 |
| 5,041,584 A | 8/1991 | Crapo et al. |
| 5,204,419 A | 4/1993 | Tsutsui et al. |
| 5,329,032 A * | 7/1994 | Tran et al. ................... 556/179 |
| 5,391,793 A * | 2/1995 | Marks et al. ................ 556/179 |
| 5,416,229 A | 5/1995 | Tran et al. |
| 5,489,659 A | 2/1996 | Sugano et al. |
| 5,648,440 A | 7/1997 | Sugano et al. |
| 5,670,589 A * | 9/1997 | Geerts et al. ............... 526/160 |
| 6,100,213 A * | 8/2000 | Kumamoto et al. ........ 502/120 |

FOREIGN PATENT DOCUMENTS

| | | |
|---|---|---|
| DE | 19711304 | 10/1997 |
| EP | 0269002 | 6/1988 |
| EP | 0452156 | 10/1991 |
| EP | 0561476 | 9/1993 |
| EP | 0726271 | 8/1996 |
| EP | 0 726 271 A1 * | 8/1996 |
| EP | 0906914 | 4/1999 |
| EP | 1081167 | 3/2001 |
| EP | 001217016 A1 * | 6/2002 |
| JP | 5819309 | 2/1983 |
| JP | 60130604 | 7/1985 |
| JP | 60260602 | 12/1985 |
| JP | 63130601 | 6/1988 |
| JP | 6136053 | 5/1994 |
| JP | 6329714 | 11/1994 |
| JP | 2693538 | 9/1997 |
| WO | 9410180 | 5/1994 |
| WO | 9532095 | 11/1995 |

OTHER PUBLICATIONS

European Search Report dated Apr. 25, 2001.
E. Lindner, et al., "Poly(Alumosiloxanes) as Matrixes for the Immobilization of Catalytically Active Ruthenium (II) Complexes", *Chem. Mater.*, vol. 10, No. 1, 1998, pp. 217–225.

* cited by examiner

*Primary Examiner*—Ling-Siu Choi
(74) *Attorney, Agent, or Firm*—Stevens, Davis, Miller & Mosher, L.L.P.

(57) ABSTRACT

A modified aluminum oxy compound(A) obtained by reacting an aluminum oxy compound(a), water (b) and a compound having a hydroxyl group(c); a polymerization catalyst component comprising the modified aluminum oxy compound; a polymerization catalyst obtained by contacting said modified aluminum oxy compound(A), a transition metal compound(B) and optionally an organoaluminum compound(C) and a specified boron compound; and a process for producing an olefin polymer or an alkenyl aromatic hydrocarbon polymer with the polymerization catalyst.

14 Claims, 6 Drawing Sheets

MODIFIED ALUMINUM OXY COMPOUND, POLYMERIZATION CATALYST AND PROCESS FOR PRODUCING OLEFIN POLYMER AND ALKENYL AROMATIC HYDROCARBON POLYMER

CROSS-REFERENCE TO RELATED APPLICATION

This application is a continuation-in-part of U.S. application Ser. No. 09/391,662, filed Sep. 7, 1999, now pending.

BACKGROUND OF THE INVENTION

1. Field of the Invention

The present invention relates to a modified aluminum oxy compound, a polymerization catalyst containing said modified aluminum oxy compound as a component, and a process for producing a polymer with said catalyst.

2. Description of the Related Arts

Many processes for producing an olefin polymer with a polymerization catalyst using a transition metal compound (for example, a metallocene and non-metallocene compound) and an aluminum oxy compound, are well-known. For example, a process using bis(cyclopentadienyl) zirconium dichloride and methylaluminoxane, is reported in JP58/019309A. However, in order to obtain the olefin polymer at a high yield, it is necessary to add a large amount of the aluminum oxy compound such as 1000 to 10000 moles of aluminum atom per 1 mole of transition metal atom. This has lead to major problems such as a high production cost and the residue of a large amount of aluminum atoms in the olefin polymer causes a bad influence on the properties of the olefin polymer.

In order to solve these problems, many reports concerning the reduction of the amount of aluminum oxy compound used have been made. For example, processes using a transition metal compound and a combination of an aluminum oxy compound and an organoaluminum compound are reported in JP60260602A and JP60130604A. Further, a process using methylaluminoxane and an aluminum oxy compound in which at least one isobutyl group is bonded with an aluminum atom, and a metallocene complex, and the like, are reported in JP63130601A. However, these processes do not reach a sufficient solution of the above-mentioned problems.

Further, polymers obtained with these catalysts have a low molecular weight in general, and the improvement has been further required for practical use.

A process using an aluminum oxy compound having an electron withdrawing group or an electron withdrawing group-containing group as an olefin polymerization catalyst component is recently reported in JP06329714A. According to this process, a highly active catalyst can be obtained, and an olefin polymer with a relatively high molecular weight can be obtained by polymerizing an olefin using said catalyst. However, the catalyst activity and the molecular weight of the olefin polymer obtained are not always sufficient, the invention of an aluminum oxy compound for realizing the more improvement of activity and the molecular weight of a polymer has been desired in order to produce an industrially useful olefin polymer.

Moreover, various investigations for synthesis of an α-olefin polymer having stereoregularity using a metallocene complex have been further carried out, and a trial of synthesizing a highly stereoregular α-olefin polymer by designing the structure of a metallocene complex is carried out.

For example, a production example of a highly stereoregular isotactic propylene polymer using a metallocene complex in which a methyl group is introduced at 2-position of the indenyl group of a silicon-bridging type bis(indenyl) complex and an isopropyl group, a phenyl group or a naphthyl group is introduced at 4-position (Organometallics 1994, 13, 954.), and a production example of a highly stereoregular isotactic propylene polymer using a metallocene complex in which two of mono- to tri-substituted $\eta^5$-cyclopentadienyl groups are bridged (JP-B-258725, JP-B-2627669 and JP-B-2668732) are known.

Further, it is reported that a syndiotactic propylene polymer is obtained by using an aluminum oxy compound with isopropylidene(cyclopentadienyl) (fluorenyl)zirconium dichloride which is a metallocene complex having Cs symmetry, or the like (J.Am.Chem.Soc.,1988,110,6255.).

SUMMARY OF THE INVENTION

An object of the present invention is to provide a modified aluminum oxy compound that is useful as a component of an olefin polymerization catalyst, which catalyst is capable of producing a high molecular weight olefin polymer with a high efficiency, and is prepared by contacting a transition metal compound with the modified aluminum compound.

Another object of the present invention is to provide a highly active olefin polymerization catalyst component using said aluminum oxy compound.

Further, another object of the present invention is to provide a process for producing a high molecular weight olefin polymer with said polymerization catalyst.

Still further, another object of the present invention is to provide an alkenyl aromatic hydrocarbon copolymer of high molecular weight and a process for producing the same with said polymerization catalyst.

Moreover, another object of the present invention is to provide a catalyst for α-olefin polymerization capable of producing a highly stereoregular α-olefin polymer, and a process for producing a highly stereoregular α-olefin polymer with said catalyst.

Other objects and advantages of the present invention will be apparent from the following description.

Namely, the present invention relates to a modified aluminum oxy compound, which has been modified with a compound having a hydroxy group, in which the ratio [M2/M1] of the intensity (M2) at 30 ppm to the intensity (M1) at 10 ppm of the spectrum in the $^{27}$Al-solid NMR is 0.60 or more; a polymerization catalyst component containing (A)said modified aluminum oxy compound; and an olefin polymerization catalyst obtained by a process that comprises contacting (A)said modified aluminum oxy compound, (B)a transition metal compound, and optionally (C)an organoaluminum compound or optionally (C)an organoaluminum compound and (D)a boron compound. Further, the present invention relates to a process for producing an olefin polymer which comprises homopolymerizing an olefin or copolymerizing olefins with said polymerization catalyst, and a process for producing an alkenyl aromatic hydrocarbon polymer which comprises homopolymerizing an alkenyl aromatic hydrocarbon or copolymerizing an alkenyl aromatic hydrocarbon and an olefin with said polymerization catalyst, and a copolymer of an alkenyl aromatic hydrocarbon and an olefin, having a number average molecular weight of 700,000 or more and a molecular weight distribution in terms of a ratio of weight average molecular weight(Mw) to number average molecular weight (Mn)[Mw/Mn] of 1.85 to 2.5.

Further, the present invention relates to a catalyst for α-olefin polymerization obtained by contacting said modified aluminum oxy compound with (B) a transition metal compound having a capability of stereoregular polymerization of α-olefin. Further, the present invention relates to a process for producing a stereoregular α-olefin polymer using said catalyst.

DETAILED DESCRIPTION OF THE INVENTION

Figure 1:
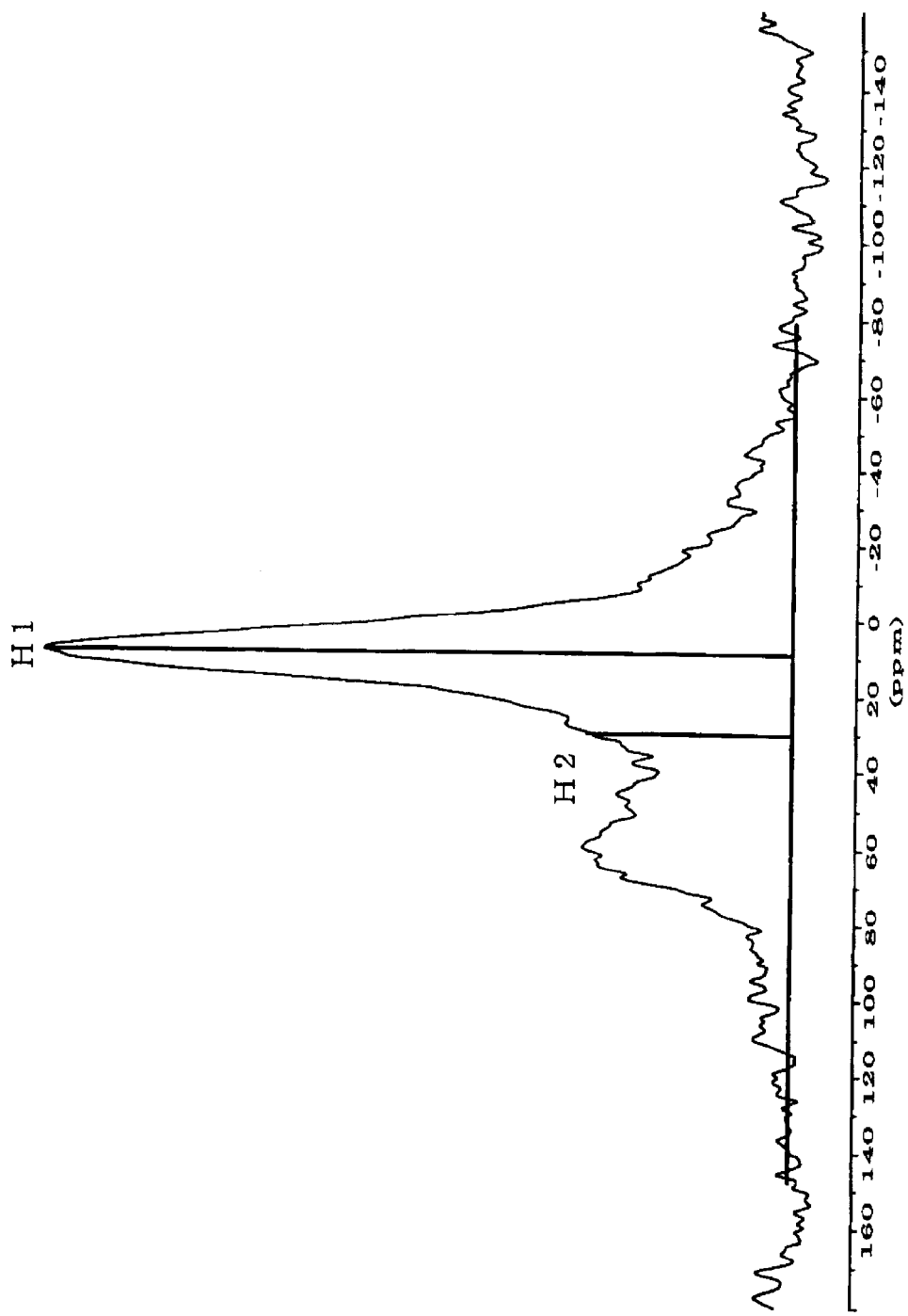
FIG. 1 shows an $^{27}$Al-solid NMR spectrum of a sample obtained by drying MMAO3A(toluene solution, manufactured by TOSOH-AKZO Co., Ltd.) used as in Example 1, under reduced pressure. The ratio of H2 to H1 was 0.27 from this spectrum.

The present invention is illustrated in detail below.
(A)Modified Aluminum Oxy Compound The modified aluminum oxy compound (A) of the present invention is a modified aluminum oxy compound in which an aluminum oxy compound is modified with a compound having a hydroxy group, and in which the ratio [M2/M1] of the intensity (M2) at 30 ppm to the intensity(Ml) at 10 ppm of the spectrum in the $^{27}$Al-solid NMR is 0.60 or more. Herein, the solid NMR spectrum means a NMR spectrum obtained by measuring a solid sample at a magic angle spinning using a high speed rotation. In the present invention, the $^{27}$Al-solid NMR spectrum measurement of the modified aluminum oxy compound or an aluminum oxy compound is conducted as follows:

When the modified aluminum oxy compound or aluminum oxy compound obtained is in a solution state dissolved in a solvent, the solvent is removed by a known method such as a reduced-pressure drying, etc. to dry and solidify the modified aluminum oxy compound or aluminum oxy compound. Herein-after, the modified aluminum oxy compound or aluminum oxy compound dried and solidified is sometimes referred to as "solid NMR measurement sample".

In a nitrogen box or a globe box, the solid NMR measurement sample was packed in a rotation cell(,or a spinner or a rotor) for solid NMR measurement in an appropriate amount so that the cell can be stably rotated. A solid NMR spectrum at a magnetic field intensity of 7.0 T ($^1$H observation magnetic field intensity at 300 MHz) is measured using a solid NMR spectrometer in which the cell is capable of high speed rotating with a nitrogen gas or an inert gas. The sample is measured under a cell rotation speed of 8 kHz or more, preferably 12 to 15 kHz. As the standard of the chemical shift, the peak appeared in high magnetic field side of an active alumina is determined as 7 ppm. The width of the spectrum is set to 400 ppm or more, preferably 600 to 1000 ppm as a chemical shift width of $^{27}$Al, considering that the group of peaks to be measured can be measured. The pulse width is set to smaller than the 900 pulse width used in a solution $^{27}$Al-NMR spectrum. The pulse interval is determined so that the relaxation does not occur.

As a measurement pulse sequences, there is illustrated a single pulse method without decoupling, for example, a pulse sequence is a HPDEC without decoupling. The measurement is usually carried out room at temperature(about 20 to about 25° C.). In the case of solid NMR measurement of $^{27}$Al nucleus, shapes of peaks and the chemical shift depend on magnetic field intensity due to an interaction of secondary quadrupole of nucleus.

Due to the reason as above, for comparisons of spectra measured, it is necessary that measurements of $^{27}$Al-solid NMR of various solid NMR samples are carried out at the same magnetic field intensity. After the measurement, the data are subjected to Fourier transfer to obtain an $^{27}$Al-solid NMR spectrum. In the obtained $^{27}$Al-solid NMR spectrum, the phase and baseline correction thereof are compensated so that the heights of bases of the highest magnetic field peak group and the lowest magnetic field peak group among peak groups appeared from a vicinity of −150 ppm to a vicinity of 150 ppm, are mutually made the same height, and the spectrum of a part in which no peak is observed in regions −150 ppm under and 150 ppm over, become parallel to the chemical shift axis (axis of abscissa) as far as possible. The baseline as a standard is drawn between bases of the highest magnetic field peak group and the lowest magnetic field peak group. A vertical line is drawn at 10 ppm to the chemical shift axis (axis of abscissa), The intensity M1 is defined as a distance between the intersecting point of the vertical line with baseline and the intersecting point of the vertical line with the spectrum. And, when a vertical is drawn at 30 ppm to the chemical shift axis (axis of abscissa), the intensity M2 is defined as a distance between the intersecting point of the vertical line with the baseline and the intersecting point of the vertical line with the spectrum. Further, H1 and H2, L1 and L2, and N1 and N2(these are as defined below) can be determined by the same method as above.

The modified aluminum oxy compound of the present invention has a ratio of M2/M1 calculated from these values above of 0.60 or more, preferably 0.65 or more, most preferably 0.70 to 1.5. The modified aluminum oxy compound of the present invention satisfies the scope of M2/M1 described above, and is one modified with a compound having a hydroxy group. The modified aluminum oxy compound of the present invention is obtained by reacting an aluminum oxy compound (a) having a ratio of an intensity (H2) at 30 ppm to a intensity(H1) at 10 ppm of less than 0.35, water(b) and a compound (c) having a hydroxy group.

The present invention will be described in more detail.

(a) Aluminum Oxy Compound

As the aluminum oxy compound used as a raw material of the modified aluminum oxy compound of the present invention, there is illustrated an aluminum oxy compound having a ratio of the intensity(H2) at 30 ppm to the intensity (H1) at 10 ppm, in the $^{27}$Al-solid NMR spectrum, of less than 0.35.

As (a) aluminum oxy compound used in the present invention, an aluminum oxy compound soluble in an aromatic hydrocarbon or an aliphatic hydrocarbon which represented by the general formula (1) or (2) described below, is preferable.

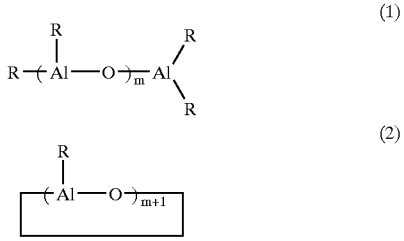

(wherein each of the R groups respectively indicates a hydrocarbon group having 1 to 20 carbon atoms, which R groups may be the same or different, and m represents a number of 1 to 50.)

The hydrocarbon group in the above-mentioned general formula (1) or (2) includes an alkyl group, alkenyl group, aryl group and aralkyl group having up to 20 carbon atoms, and the like, and an alkyl group having 1 to 20 carbon atoms is preferable.

The specific examples thereof include methylaluminoxane, ethylaluminoxane, propylaluminoxane, butylaluminoxane, isobutylaluminoxane, methylethylaluminoxane, methylbutylaluminoxane, methylisobutylaluminoxane, and the like are exemplified. Most of these compounds are commercially available or can be synthesized by well-known methods. Among them, methylisobutyl aluminoxane is preferable in particular, R in the above-mentioned general formula (1) or (2) represents a methyl group or an isobutyl group in respective cases. An aluminum oxy compound in which the existence ratio of a methyl group as R to an isobutyl group as R (methyl group/isobutyl group) is (5 to 95)/(95 to 5) is more preferable, and the ratio is preferably (10 to 90)/(90 to 10) in particular.

These aluminum oxy compounds may be used alone or in combination of 2 or more kinds.

(b) Water

When the modified aluminum oxy compound of the present invention is produced, a water(b) is used. The water(b) is preferably a distilled water or de-ionized water. When water(b) is used in the present invention, it is unknown in detail why the molecular weight of the aluminum oxy compound seems to increase, and the viscosity thereof increases, and as the case may be, the precipitation of a solid, are observed.

(c) Compound Having Hydroxyl Group

The compound(c) having a hydroxyl group used in preparation of the modified aluminum oxy compound (A) of the present invention, is a compound having at least one hydroxyl group in its molecule, and an organic compound having a hydroxyl group is preferable. An alcohol compound, a phenol compound or a silanol compound is more preferable. Herein, the alcohol compound preferably includes a compound indicated by the general formula below:

$$CR^1R^2R^3\text{---}OH$$

(wherein each of $R^1$, $R^2$ and $R^3$ independently represents a hydrogen atom or a hydrocarbon group having 1 to 20 carbon atoms, and they may be mutually the same or different.)

The hydrocarbon group in the above-mentioned general formula includes an alkyl group, an aralkyl group, an aryl group and the like, and these groups may be optionally substituted with a halogen atom.

Tertiary alcohols and alcohols substituted with a halogen atom are preferable, and in particular, tert-butyl alcohol, triphenylmethanol, tricyclohexylmethanol or 1,1,1,3,3,3-hexafluoroisopropanol is preferable.

Further, as the phenol compound, non-substituted phenols or substituted phenols can be used. Wherein the substituent includes a halogen atom, an alkyl group, aralkyl group, aryl group, silyl group, alkoxy group, aralkyloxy group, aryloxy group or silyloxy group which may be substituted with a halogen atom, or the like.

Specific examples of such phenol compound include 2-substituted phenols such as 2-methylphenol, 2-ethylphenol, 2-n-butylphenol, 2-isobutylphenol, 2-tert-butylphenol, 2-n-propylphenol, 2-isopropylphenol, 2-phenylphenol, 2-fluorophenol, 2-chlorophenol, 2-bromophenol and the like; 3-substituted phenols such as 3-methylphenol, 3-ethylphenol, 3-n-butylphenol, 3-isobutylphenol, 3-tert-butylphenol, 3-n-propylphenol, 3-isopropylphenol, 3-phenylphenol, 3-fluorophenol, 3-chlorophenol, 3-bromophenol and the like; 4-substituted phenols such as 4-methylphenol, 4-ethylphenol, 4-n-butylphenol, 4-isobutylphenol, 4-tert-butylphenol, 4-n-propylphenol, 4-isopropylphenol, 4-phenylphenol, 4-fluorophenol, 4-chlorophenol, 4-bromophenol and the like; 2,6-substituted phenols such as 2,6-dimethylphenol, 2,6-diethylphenol, 2,6-di-n-butylphenol, 2,6-diisobutylphenol, 2,6-di-tert-butylphenol, 2,6-di-n-propylphenol, 2,6-diisopropylphenol, 2,6-diphenylphenol, 2,6-difluorophenol, 2,6-dichlorophenol, 2,6-dibromophenol and the like; 2,6,X-substituted phenols (X is one or more numerals selected from 3, 4 and 5) such as 2,4,6-trimethylphenol, 2,6-di-tert-butyl-4-methylphenol, 2,3,5,6-tetrafluorophenol, pentafluorophenol and the like; 2,3-substituted phenols such as 2,3-difluorophenol and the like; 2,4-substituted phenols such as 2,4-difluorophenol and the like; 3,5-substituted phenols such as 3,5-dimethylphenol, 3,5-diethylphenol, 3,5-di-n-butylphenol, 3,5-diisobutylphenol, 3,5-di-tert-butylphenol, 3,5-di-n-propylphenol, 3,5-diisopropylphenol, 3,5-diphenylphenol, 3,5-difluorophenol, 3,5-dichlorophenol, 3,5-dibromophenol and the like; phenols having 2 or more hydroxy groups such as catechol, resorcinol, hydroquinone, bisphenol-A, 2,2-thiobis-6-tert-butyl-4-methylphenol and the like.

As the phenol compound, a phenol having bulky substituents at 2,6-position or a halogenated phenol is preferable, and in particular, pentafluorophenol is preferable.

Further, the silanol is preferably a compound represented by the general formula below:

$$SiR^4R^5R^6\text{---}OH$$

(wherein each of $R^4$, $R^5$ and $R^6$ dependently represents a hydrogen atom or a hydrocarbon group having 1 to 20 carbon atoms, they may be mutually the same or different.)

The hydrocarbon group in the above-mentioned general formula includes an alkyl group, an aralkyl group, an aryl group and the like, and these groups may be optionally substituted with a halogen atom.

A tertiary silanol or a silanol substituted with a halogen atom is preferred, and triphenylsilanol or tricyclohexylsilanol is more preferred.

As the compound(c) having a hydroxyl group used in the present invention, an alcohol compound or a phenol compound is preferable, and in particular, pentafluorophenol, triphenylmethanol, tricyclohexylmethanol or 1,1,1,3,3,3-hexafluoroisopropanol is preferable.

These compounds having a hydroxyl group may be used alone or in combination of 2 or more kinds.

(d) Preparation of Modified Aluminum Oxy Compound (A)

The modified aluminum oxy compound (A) of the present invention is obtained by reacting (a) an aluminum oxy compound having a ratio of the intensity(H2) at 30 ppm in the $^{27}$Al-solid NMR spectrum to the intensity(H1) at 10 ppm in that of less than 0.35, (b) water and (c) a compound having a hydroxyl group.

The reaction is preferably carried out in an inert gas atmosphere. The reaction temperature is not specifically limited, but is usually −80° C. to 200° C. and preferably −50° C. to 120° C. The reaction time is usually 1 minute to 12 hours and preferably 2 minutes to 1 hour. Further, in this reaction, a solvent may be used, and these reactants (a), (b) and (c) may be directly reacted without a solvent. The solvent used is not specifically limited, and includes an aliphatic hydrocarbon solvent or an aromatic hydrocarbon solvent. Specific example thereof includes hexane, heptane, benzene, toluene or the like.

The modified aluminum oxy compound of the present invention is preferably obtained by reacting (a) the aluminum oxy compound with (b) water to obtain (a') an aluminum oxy compound having a ratio (L2/L1) of an intensity (L2) at 30 ppm in an $^{27}$Al-solid NMR spectrum to an intensity(L1) at 10 ppm in that of 0.35 or more, and then reacting (a') the resulting aluminum oxy compound with (c) a compound having a hydroxyl group, or by reacting (a)the aluminum oxy compound with (c) the compound having a hydroxyl group to obtain (a")an aluminum oxy compound having a ratio(N2/N1) of an intensity(N2) at 30 ppm in a $^{27}$Al-solid NMR spectrum to an intensity (N1) at 10 ppm in that of 0.35 or more, and then reacting (a") with (b) water. When the (a') the aluminum oxy compound is available, a modified aluminum oxy compound (A) is obtained by reacting the (a') with (c) a compound having a hydroxyl group.

The ratio, L2/L1 is preferably 0.35 or more and less than 0.90, more preferably 0.35 to 0.85.

And, the ratio of (L2/L1) to (H2/H1) [(L2/L1)/(H2/H1)] is preferably 1.5 or more, more preferably 1.5 or more and less than 9.0. Further, the ratio, N2/N1 is preferably 0.35 or more and less than 0.65, more preferably 0.35 to 0.60.

The molar ratio of respective components used in the reaction is not specifically limited, and the molar ratio of the component (a)(in terms of mol of Al atom) to the component (b) ((a)/(b)) is preferably within the range of 1/3 to 1/0.01, more preferably 1/1 to 1/0.05. Further, the molar ratio of the component (a)(in terms of mol of Al atom) to the component (c)is preferably within the range of 1/3 to 1/0.01, more preferably 1/1 to 1/0.05. The molar ratio of the component (a')(in terms of mol of Al atom) to the component (c) ((a')/(c)) is preferably within the range of 1/3 to 1/0.01, more preferably 1/1 to 1/0.05. Further, the molar ratio of the component (a")(in terms of mol of Al atom) to the component(b) is preferably within the range of 1/3 to 1/0.01, more preferably 1/1 to 1/0.05.

The modified aluminum oxy compound of the present invention obtained by the preparation method described above or the like can be used as a polymerization catalyst component after purification by isolation such as recrystallization or the like, but the reaction solution containing the modified aluminum oxy compound can be also used as the polymerization catalyst component as it is.

The modified aluminum oxy compound of the present invention is useful as the polymerization catalyst component. Examples of the polymerization catalyst using the modified aluminum oxy compound of the present invention include the polymerization catalyst obtained by contacting (A) the modified aluminum oxy compound and (B) a transition metal compound; the polymerization catalyst obtained by contacting (A) the modified aluminum oxy compound, (B) the transition metal compound and (C) the organoaluminum compound; and the polymerization catalyst obtained by contacting (A) the modified aluminum oxy compound, (B) the transition metal compound, (C) the organoaluminum compound and (D) any one boron compounds (D1) to (D3) described below:

(D1) a boron compound represented by the general formula $BQ^1Q^2Q^3$, (D2) a boron compound represented by the general formula $G^+(BQ^1Q^2Q^3Q^4)^-$, and (D3) a boron compound represented by the general formula $(L—H)^+(BQ^1Q^2Q^3Q^4)^-$ (wherein B represents a boron atom in the trivalent valence state; $Q^1$ to $Q^4$ may be the same or different and represent a halogen atom, a hydrocarbon group, a halogenated hydrocarbon group, a substituted silyl group, an alkoxy group or a di-substituted amino group; $G^+$ represents an inorganic or organic cation; L represents a neutral Lewis base; and $(L—H)^+$ represents a Brfnsted acid).

The polymerization catalyst of the present invention will be described in more detail below.

(B) Transition Metal Compound

The transition metal compound used for the olefin polymerization catalyst of the present invention is not specifically limited so far as it is a transition metal compound having an olefin polymerization activity. A transition metal compound having a transition metal atom of the Group IV to X of the Periodic Table of the Elements and Lanthanide Series is preferable. Example of the transition metal compound includes a transition metal compound indicated by the general formula (3) described below, a μ-oxo type transition metal compound obtained by reacting the transition metal compound with water as a dimer thereof, and the like.

$$L_aMX_b \qquad (3)$$

(wherein M is a transition metal atom of the Group IV to Group X of the Periodic Table or Lanthanide Series; L is a group having a cyclopentadienyl type anion skeleton or a group containing a hetero-atom, and a plurality of L groups may be optionally linked in direct, or through a group containing a carbon atom, a silicone atom, a nitrogen atom, an oxygen atom, a sulfur atom or a phosphorus atom; X is a halogen atom or a hydrocarbon group having 1 to 20 carbon atoms; a represents a numeral satisfying an equation of $0<a\leq8$; b represents a numeral satisfying an equation of $0<b\leq8$; and a and b are properly selected so that the transition metal compound become neutral taking into account of the valency of the transition metal M and the valencies of L and X.)

In the general formula (3) representing the transition metal compound, M is a transition metal atom of the Group IV to Group X of the Periodic Table (IUPAC 1985) or Lanthanide Series. Specific examples of the transition metal atom include titanium, zirconium, hafnium, vanadium, niobium, tantalum, chromium, iron, ruthenium, cobalt, rhodium, nickel, palladium, samarium, ytterbium and the like.

In the general formula (3) representing the transition metal compound, L is a group having a cyclopentadienyl type anion skeleton or a group containing a hetero-atom, and L groups may be the same or different. Further, L groups may be optionally linked in direct, or through a group containing a carbon atom, a silicone atom, a nitrogen atom, an oxygen atom, a sulfur atom or a phosphorus atom.

A cyclopentadienyl type anion skeleton in L includes a cyclopentadienyl group, a substituted cyclopentadienyl group, an indenyl group, a substituted indenyl group, a fluorenyl group, a substituted fluorenyl group and the like. Examples of the group having a cyclopentadiene type anion skeleton include an $\eta^5$-(substituted)cyclopentadienyl group, an $\eta^5$-(substituted)indenyl group, an $\eta^5$-(substituted) fluorenyl group and the like. Specific examples include an $\eta^5$-cyclopentadienyl group, an $\eta^5$-methylcyclopentadienyl group, an $\eta^5$-tert-butylcyclopentadienyl group, an $\eta^5$-1,2-dimethylcyclopentadienyl group, an $\eta^5$-1,3-dimethylcyclopentadienyl group, an $\eta^5$-1-tert-butyl-2-methylcyclopentadienyl group, an $\eta^5$-1-tert-butyl-3-methylcyclopentadienyl group, an $\eta^5$-1-methyl-2-isopropylcyclopentadienyl group, an $\eta^5$-1-methyl-3-isopropylcyclopentadienyl group, an $\eta^5$-1,2,3-trimethylcyclopentadienyl group, an $\eta^5$-1,2,4-trimethylcyclopentadienyl group, an $\eta^5$-tetramethylcyclopentadienyl group, an $\eta^5$-pentamethylcyclopentadienyl group, an $\eta^5$-indenyl group, an $\eta^5$-4,5,6,7-tetrahydroindenyl group, an $\eta^5$-2-methylindenyl group, an $\eta^5$-3-methylindenyl group, an $\eta^5$-4-methylindenyl group, an $\eta^5$-5-methylindenyl group, an $\eta^5$-6-methylindenyl group, an $\eta^5$-7-methylindenyl group, an $\eta^5$-2-tert-butylindenyl group, an $\eta^5$-3-tert-butylindenyl group, an $\eta^5$-4-tert-butylindenyl group, an $\eta^5$-tert-butylindenyl group, an $\eta^5$-6-tert-butylindenyl group, an $\eta^5$-7-tert-butylindenyl group, an $\eta^5$-2,3-dimethylindenyl group, an $\eta^5$-4,7-dimethylindenyl group, an $\eta^5$-2,4,7-trimethylindenyl group, an $\eta^5$-2-methyl-4-isopropylindenyl group, an $\eta^5$-4,5-benzindenyl group, an $\eta^5$-2-methyl-4,5-benzindenyl group, an $\eta^5$-4-phenylindenyl group, an $\eta^5$-2-methyl-5-phenylindenyl group, an $\eta^5$-2-methyl-4-phenylindenyl group, an $\eta^5$-2-methyl-4-naphthylindenyl group, an $\eta^5$-fluorenyl group, an $\eta^5$-2,7-dimethylfluorenyl group, an $\eta^5$-2,7-di-tert-butylfluorenyl group(herein-after, $\eta^5$ may be omitted for simplifying), and substitution products thereof, etc.

The hetero-atom in the group containing a hetero-atom includes an oxygen atom, a sulfur atom, a nitrogen atom, a phosphorus atom and the like, and examples thereof include an alkoxy group, an aryloxy group, a thioalkoxy group, a thioaryloxy group, an alkylamino group, an arylamino group, an alkylphosphino group, an arylphosphino group, or an aromatic or aliphatic heterocyclic group having an oxygen atom, a sulfur atom, a nitrogen atom and/or a phosphorus atom, a chelating ligand.

Specific examples of the group containing a hetero-atom include a methoxy group, an ethoxy group, a n- or iso-propoxy group, a n-, sec-, iso- or tert-butoxy group, a phenoxy group, a 2-methylphenoxy group, a 2,6-dimethylphenoxy group, a 2,4,6-trimethylphenoxy group, a 2-ethylphenoxy group, a 4-n-propylphenoxy group, a 2-isopropylphenoxy group, a 2,6-diisopropylphenoxy group, a 4-sec-butylphenoxy group, a 4-tert-butylphenoxy group, a 2,6-di-sec-butylphenoxy group, a 4-tert-butyl-4-methylphenoxy group, a 2,6-di-tert-butylphenoxy group, a 4-methoxyphenoxy group, a 2,6-dimethoxyphenoxy group, a 3,5-dimethoxyphenoxy group, a 2-chlorophenoxy group, a 4-nitrosophenoxy group, a 4-nitrophenoxy group, a 2-aminophenoxy group, a 3-aminophenoxy group, a 4-aminothiophenoxy group, a 2,3,6-trichlorophenoxy group, a 2,4,6-trifluorophenoxy group, a thiomethoxy group, a dimethylamino group, a diethylamino group, a di-n- or iso-propylamino group, a diphenylamino group, an isopropylamino group, a tert-butylamino group, a pyrrolyl group, a dimethylphosphino group, a 2-(2-oxy-1-propyl)phenoxy group, catechol, resorcinol, 4-isopropylcatechol, 3-methoxycatechol, a 1,8-dihydroxynahpthyl group, a 1,2-dihydroxynahpthyl group, a 2,2'-biphenyldiol group, a 1,1'-bi-2-naphthol group, a 2,2'-dihydroxy-6,6'-dimethylbiphenyl group, a 4,4',6,6'-tetra-tert-butyl-2,2'-methylenediphenoxy group, a 4,4',6,6'-tetramethyl-2,2'-isobutylidenediphenoxy group and the like.

Further, the chelating ligand means a ligand having a plural number of coordinating positions, and specific examples include acetylacetonate, diimine, oxazoline, bisoxazoline, terpyridine, acylhydrazone, diethylenetriamine, triethylenetetramine, porphyrin, a crown ether, a cryptate and the like.

The mutual groups having the cyclopentadienyl type anion skeleton, the group having a cyclopentadienyl type anion skeleton and the group containing a hetero-atom, or the mutual groups containing a hetero-atom may be directly linked, or may be linked through a group containing a carbon atom, a silicone atom, a nitrogen atom, an oxygen atom, a sulfur atom or a phosphorus atom, respectively. Examples of the group include alkylene groups such as an ethylene group, a propylene group and the like, substituted alkylene groups such as a dimethylmethylene group, a diphenylmethylene group and the like, or a silylene group, substituted silylene groups such as a dimethylsilylene group, a diphenylsilylene group, a tetramethyldisilylene group and the like, or hetero-atoms such as a nitrogen atom, an oxygen atom, a sulfur atom and/or a phosphorus atom and the like, etc.

X in the general formula (3) representing the transition metal compound is a halogen atom or a hydrocarbon group having 1 to 20 carbon atoms. Specific examples of X include a fluorine atom, a chlorine atom, a bromine atom, an iodine atom, and examples of the hydrocarbon group having 1 to 20 carbon atoms include alkyl groups, aryl groups, aralkylgroups(e.g. a methyl group, an ethyl group, a n-propyl group, an isopropyl group, a n-butyl group, a phenyl group, a benzyl group), and the like.

Among the transition metal compound, specific examples of the compound in which a transition metal is a titanium atom include bis(cyclopentadienyl)titanium dichloride, bis(methylcyclopentadienyl)titanium dichloride, bis(n-butylcyclopentadienyl)titanium dichloride, bis(dimethylcyclopentadienyl)titanium dichloride, bis(ethylmethylcyclopentadienyl)titanium dichloride, bis(trimethylcyclopentadienyl)titanium dichloride, bis(tetramethylcyclopentadienyl)titanium dichloride, bis(pentamethylcyclopentadienyl)titanium dichloride, bis(indenyl)titanium dichloride, bis(4,5,6,7-tetrahydroindenyl)titanium dichloride, bis(fluorenyl)titanium dichloride, cyclopentadienyl(pentamethylcyclopentadienyl)titanium dichloride, cyclopentadienyl(indenyl)titanium dichloride, cyclopentadienyl(fluorenyl)titanium dichloride, indenyl (fluorenyl)titanium dichloride, pentamethylcyclopentadienyl (indenyl)titanium dichloride, pentamethylcyclopentadienyl(fluorenyl)titanium dichloride, ethylenebis(cyclopentadienyl)titanium dichloride, ethylenebis(2-methylcyclopentadienyl)titanium dichloride, ethylenebis(3-methylcyclopentadienyl)titanium dichloride, ethylenebis(2-n-butylcyclopentadienyl)titanium dichloride, ethylenebis(3-n-butylcyclopentadienyl)titanium dichloride, ethylenebis(2,3-dimethylcyclopentadienyl)titanium dichloride, ethylenebis(2,4-dimethylcyclopentadienyl)titanium dichloride, ethylenebis(2,5-dimethylcyclopentadienyl)titanium dichloride, ethylenebis(3,4-dimethylcyclopentadienyl)titanium dichloride, ethylenebis(2,3-ethylmethylcyclopentadienyl)titanium dichloride, ethylenebis(2,4-ethylmethylcyclopentadienyl)titanium dichloride, ethylenebis(2,5-ethylmethylcyclopentadienyl)titanium dichloride, ethylenebis(3,5-ethylmethylcyclopentadienyl)titanium dichloride, ethylenebis(2,3,4-trimethylcyclopentadienyl)titanium dichloride, ethylenebis(2,3,5-trimethylcyclopentadienyl)titanium dichloride, ethylenebis(tetramethylcyclopentadienyl)titanium dichloride, ethylenebis(indenyl)titanium dichloride, ethylenebis(4,5,6,7-tetrahydroindenyl)titanium dichloride, ethylenebis(2-phenylindenyl)titanium dichloride, ethylenebis(2-methylindenyl)titanium dichloride, ethylenebis(2-methyl-4-phenylindenyl)titanium dichloride, ethylenebis(2-methyl-4-naphthylindenyl)titanium dichloride, ethylenebis(2-methyl-4,5-benzoindenyl)titanium dichloride, ethylenebis(fluorenyl)titanium dichloride, ethylene(cyclopentadienyl)(pentamethylcyclopentadienyl)titanium dichloride, ethylene(cyclopentadienyl)(indenyl)titanium dichloride, ethylene(methylcyclopentadienyl)(indenyl)titanium dichloride, ethylene(n-butylcyclopentadienyl)(indenyl)titanium dichloride, ethylene(tetramethylcyclopentadienyl)(indenyl)titanium dichloride, ethylene(cyclopentadienyl)(fluorenyl)titanium dichloride, ethylene(methylcyclopentadienyl)(fluorenyl)titanium dichloride, ethylene(pentamethylcyclopentadienyl)(fluorenyl)titanium dichloride, ethylene(n-butylcyclopentadienyl)(fluorenyl)titanium dichloride, ethylene(tetramethylpentadienyl)(fluorenyl)titanium dichloride, ethylene(indenyl)(fluorenyl)titanium dichloride, isopropylidenebis(cyclopentadienyl)titanium dichloride, isopropylidenebis(2-methylcyclopentadienyl)titanium dichloride, isopropylidenebis(3-methylcyclopentadienyl)titanium dichloride, isopropylidenebis(2-n-butylcyclopentadienyl)titanium dichloride, isopropylidenebis(3-n-butylcyclopentadienyl)titanium dichloride, isopropylidenebis(2,3-dimethylcyclopentadienyl)titanium dichloride, isopropylidenebis(2,4-dimethylcyclopentadienyl)titanium dichloride, isopropylidenebis(2,5-dimethylcyclopentadienyl)titanium dichloride, isopropylidenebis(3,4-dimethylcyclopentadienyl)titanium dichloride, isopropylidenebis(2,3-ethylmethylcyclopentadienyl)titanium dichloride, isopropylidenebis(2,4-ethylmethylcyclopentadienyl)titanium dichloride, isopropylidenebis(2,5-ethylmethylcyclopentadienyl)titanium dichloride, isopropylidenebis(3,5-ethylmethylcyclopentadienyl)titanium dichloride, isopropylidenebis(2,3,4-trimethylcyclopentadienyl)titanium dichloride, isopropylidenebis(2,3,5-trimethylcyclopentadienyl)titanium dichloride, isopropylidenebis(tetramethylcyclopentadienyl)titanium dichloride, isopropylidenebis(indenyl)titanium dichloride, isopropylidenebis(4,5,6,7-tetrahydroindenyl)titanium dichloride, isopropylidenebis(2-phenylindenyl)titanium dichloride, isopropylidenebis(2-methylindenyl)titanium dichloride, isopropylidenebis(2-methyl-4-phenylindenyl)titanium dichloride, isopropylidenebis(2-methyl-4-naphthylindenyl)titanium dichloride, isopropylidenebis(2-methyl-4,5-benzoindenyl)titanium dichloride, isopropylidenebis(fluorenyl)titanium dichloride, isopropylidene(cyclopentadienyl)(tetramethylcyclopentadienyl)titanium dichloride, isopropylidene(cyclopentadienyl)(indenyl)titanium dichloride, isopropylidene(methylcyclopentadienyl)(indenyl)titanium dichloride, isopropylidene(n-butylcyclopentadienyl)(indenyl)titanium dichloride, isopropylidene(tetramethylcyclopentadienyl)(indenyl)titanium dichloride, isopropylidene(cyclopentadienyl)(fluorenyl)titanium dichloride, isopropylidene(methylcyclopentadienyl)(fluorenyl)titanium dichloride, isopropylidene(n-butylcyclopentadienyl)(fluorenyl)titanium dichloride, isopropylidene(tetramethylcyclopentadienyl)(fluorenyl)titanium dichloride, isopropylidene(indenyl)(fluorenyl)titanium dichloride, dimethylsilylenebis(cyclopentadienyl)titanium dichloride, dimethylsilylenebis(2-methylcyclopentadienyl)titanium dichloride, dimethylsilylenebis(3-methylcyclopentadienyl)titanium dichloride, dimethylsilylenebis(2-n-butylcyclopentadienyl)titanium dichloride, dimethylsilylenebis(3-n-butylcyclopentadienyl)titanium dichloride, dimethylsilylenebis(2,3-dimethylcyclopentadienyl)titanium dichloride, dimethylsilylenebis(2,4-dimethylcyclopentadienyl)titanium dichloride, dimethylsilylenebis(2,5-dimethylcyclopentadienyl)titanium dichloride, dimethylsilylenebis(3,4-dimethylcyclopentadienyl)titanium dichloride, dimethylsilylenebis(2,3-ethylmethylcyclopentadienyl)titanium dichloride, dimethylsilylenebis(2,4-ethylmethylcyclopentadienyl)titanium dichloride, dimethylsilylenebis(2,5-ethylmethylcyclopentadienyl)titanium dichloride, dimethylsilylenebis(3,5-ethylmethylcyclopentadienyl)titanium dichloride, dimethylsilylenebis(2,3,4-trimethylcyclopentadienyl)titanium dichloride, dimethylsilylenebis(2,3,5-trimethylcyclopentadienyl)titanium dichloride, dimethylsilylenebis(tetramethylcyclopentadienyl)titanium dichloride, dimethylsilylenebis(indenyl)titanium dichloride, dimethylsilylenebis(4,5,6,7-tetrahydroindenyl)titanium dichloride, dimethylsilylenebis(2-methylindenyl)titanium dichloride, dimethylsilylenebis(2-methyl-4-phenylindenyl)titanium dichloride, dimethylsilylenebis(2-methyl-4-naphthylindenyl)titanium dichloride, dimethylsilylenebis(2-methyl-4,5-benzoindenyl)titanium dichloride, dimethylsilylene(cyclopentadienyl)(indenyl)titanium dichloride, dimethylsilylene(methylcyclopentadienyl)(indenyl)titanium dichloride, dimethylsilylene(n-butylcyclopentadienyl)(indenyl)titanium dichloride, dimethylsilylene(tetramethylcyclopentadienyl)(indenyl)titanium dichloride, dimethylsilylene(cyclopentadienyl)(fluorenyl)titanium dichloride, dimethylsilylene(methylcyclopentadienyl)(fluorenyl)titanium dichloride, dimethylsilylene(n-butylcyclopentadienyl)(fluorenyl)titanium dichloride, dimethylsilylene-(tetramethylcyclopentadienyl)(indenyl)titanium dichloride, dimethylsilylene-(indenyl)(fluorenyl)titanium dichloride, cyclopentadienyltitanium trichloride, pentamethylcyclopentadienyltitanium trichloride, cyclopentadienyl(dimethylamido)titanium dichloride, cyclopentadienyl(phenoxy)titanium dichloride, cyclopentadienyl(2,6- dimethylphenyl)titanium dichloride, cyclopentadienyl(2,6-diisopropylphenyl)titanium dichloride, cyclopentadienyl(2,6-di-tert-butylphenyl)titanium dichloride, pentamethylcyclopentadienyl(2,6-dimethylphenyl)titanium dichloride, pentamethylcyclopentadienyl(2,6-diisopropylphenyl)titanium dichloride, pentamethylcyclopentadienyl(2,6-di-tert-butylphenyl)titanium dichloride, indenyl(2,6-diisopropylphenyl)titanium dichloride, fluorenyl(2,6-diisopropylphenyl)titanium dichloride, methylene(cyclopentadienyl)(3,5-dimethyl-2-phenoxy)titanium dichloride, methylene(cyclopentadienyl)(3-tert-butyl-2-phenoxy)titanium dichloride, methylene(cyclopentadienyl)(3-tert-butyl-5-methyl-2-phenoxy)titanium dichloride, methylene(cyclopentadienyl)(3-phenyl-2-phenoxy)titanium dichloride, methylene(cyclopentadienyl)(3-tert-butyldimethylsilyl-5-methyl-2-phenoxy)titanium dichloride, methylene(cyclopentadienyl)(3-trimethylsilyl-5-methyl-2-phenoxy)titanium dichloride, methylene(cyclopentadienyl)(3-tert-butyl-5-methoxy-2-phenoxy)titanium dichloride, methylene(cyclopentadienyl)(3-tert-butyl-5-chloro-2-phenoxy)titanium dichloride, methylene(methylcyclopentadienyl)(3,5-dimethyl-2-phenoxy)titanium dichloride, methylene(methylcyclopentadienyl)(3-tert-butyl-2-phenoxy)titanium dichloride, methylene(methylcyclopentadienyl)(3-tert-butyl-5-methyl-2-phenoxy)titanium dichloride, methylene(methylcyclopentadienyl)(3-phenyl-2-phenoxy)titanium dichloride, methylene(methylcyclopentadienyl)(3-tert-butyldimethylsilyl-5-methyl-2-phenoxy)titanium dichloride, methylene(methylcyclopentadienyl)(3-trimethylsilyl-5-methyl-2-phenoxy)titanium dichloride, methylene(methylcyclopentadienyl)(3-tert-butyl-5-methoxy-2-phenoxy)titanium dichloride, methylene(methylcyclopentadienyl)(3-tert-butyl-5-chloro-2-phenoxy)titanium dichloride, methylene(tert-butylcyclopentadienyl)(3,5-dimethyl-2-phenoxy)titanium dichloride, methylene(tert-butylcyclopentadienyl)(3-tert-butyl-2-phenoxy)titanium dichloride, methylene(tert-butylcyclopentadienyl)(3-tert-butyl-5-methyl-2-phenoxy)titanium dichloride, methylene(tert-butylcyclopentadienyl)(3-phenyl-2-phenoxy)titanium dichloride, methylene(tert-butylcyclopentadienyl)(3-tert-butyldimethylsilyl-5-methyl-2-phenoxy)titanium dichloride, methylene(tert-butylcyclopentadienyl)(3-trimethylsilyl-5-methyl-2-phenoxy)titanium dichloride, methylene(tert-butylcyclopentadienyl)(3-tert-butyl-5-methoxy-2-phenoxy)titanium dichloride, methylene(tert-butylcyclopentadienyl)(3-tert-butyl-5-chloro-2-phenoxy)titanium dichloride, methylene(tetramethylcyclopentadienyl)(3,5-dimethyl-2-phenoxy)titanium dichloride, methylene(tetramethylcyclopentadienyl)(3-tert-butyl-2-phenoxy)titanium dichloride, methylene(tetramethylcyclopentadienyl)(3-tert-butyl-5-methyl-2-phenoxy)titanium dichloride, methylene(tetramethylcyclopentadienyl)(3-phenyl-2-phenoxy-)titanium dichloride, methylene(tetramethylcyclopentadienyl)(3-tert-butyldimethylsilyl-5-methyl-2-phenoxy)titanium dichloride, methylene(tetramethylcyclopentadienyl)(3-trimethylsilyl-5-methyl-2-phenoxy)titanium dichloride, methylene(tetramethylcyclopentadienyl)(3-tert-butyl-5-methoxy-2-phenoxy)titanium dichloride, methylene(tetramethylcyclopentadienyl)(3-tert-butyl-5-chloro-2-phenoxy)titanium dichloride, methylene(trimethylsilylcyclopentadienyl)(3,5-dimethyl-2-phenoxy)titanium dichloride, methylene(trimethylsilylcyclopentadienyl)(3-tert-butyl-2-phenoxy)titanium dichloride, methylene(trimethylsilylcyclopentadienyl)(3-tert-butyl-5-methyl-2-phenoxy)titanium dichloride, methylene(trimethylsilylcyclopentadienyl)(3-phenyl-2-phenoxy)titanium dichloride, methylene(trimethylsilylcyclopentadienyl)(3-tert-butyldimethylsilyl-5-methyl-2-phenoxy)titanium dichloride, methylene(trimethylsilylcyclopentadienyl)(3-trimethylsilyl-5-methyl-2-phenoxy)titanium dichloride, methylene(trimethylsilylcyclopentadienyl)(3-tert-butyl-5-methoxy-2-phenoxy)titanium dichloride, methylene(trimethylsilylcyclopentadienyl)(3-tert-butyl-5-chloro-2-phenoxy)titanium dichloride, methylene(fluorenyl)(3,5-dimethyl-2-phenoxy)titanium dichloride, methylene(fluorenyl)(3-tert-butyl-2-phenoxy)titanium dichloride, methylene(fluorenyl)(3-tert-butyl-5-methyl-2-phenoxy)titanium dichloride, methylene(fluorenyl)(3-phenyl-2-phenoxy)titanium dichloride, methylene(fluorenyl)(3-tert-butyldimethylsilyl-5-methyl-2-phenoxy)titanium dichloride, methylene(fluorenyl)(3-trimethylsilyl-5-methyl-2-phenoxy)titanium dichloride, methylene(fluorenyl)(3-tert-butyl-5-methoxy-2-phenoxy)titanium dichloride, methylene(fluorenyl)(3-tert-butyl-5-chloro-2-phenoxy)titanium dichloride, isopropylidene(cyclopentadienyl)(3,5-dimethyl-2-phenoxy)titanium dichloride, isopropylidene(cyclopentadienyl)(3-tert-butyl-2-phenoxy)titanium dichloride, isopropylidene(cyclopentadienyl)(3-tert-butyl-5-methyl-2-phenoxy)titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene(cyclopentadienyl)(3-trimethylsilyl-5-methyl-2-phenoxy)titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene(methylcyclopentadienyl)(3-tert-butyl-2-phenoxy)titanium dichloride, isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene(methylcyclopentadienyl)(3-tert-butyldimethylsilyl-5-methyl-2-phenoxy)titanium dichloride, isopropylidene(methylcyclopentadienyl)(3-trimethylsilyl-5-methyl-2-phenoxy)titanium dichloride, isopropylidene(methylcyclopentadienyl)(3-tert-butyl-5-methoxy-2-phenoxy)titanium dichloride, isopropylidene(methylcyclopentadienyl)(3-tert-butyl-5-chloro-2-phenoxy)titanium dichloride, isopropylidene(tert-butylcyclopentadienyl)(3,5-dimethyl-2-phenoxy)titanium dichloride, isopropylidene(tert-butylcyclopentadienyl)(3-tert-butyl-2-phenoxy)titanium dichloride, isopropylidene(tert-butylcyclopentadienyl)(3-tert-butyl-5-methyl-2-phenoxy)titanium dichloride, isopropylidene(tert-butylcyclopentadienyl)(3-phenyl-2-phenoxy)titanium dichloride, isopropylidene(tert-butylcyclopentadienyl)(3-tert-butyldimethylsilyl-5-methyl-2-phenoxy)titanium dichloride, isopropylidene(tert-butylcyclopentadienyl)(3-trimethylsilyl-5-methyl-2-phenoxy)titanium dichloride, isopropylidene(tert-butylcyclopentadienyl)(3-tert-butyl-5-methoxy-2-phenoxy)titanium dichloride, isopropylidene(tert-butylcyclopentadienyl)(3-tert-butyl-5-chloro-2-phenoxy)titanium dichloride, isopropylidene(tetramethylcyclopentadienyl)(3,5-dimethyl-2-phenoxy)

titanium dichloride, isopropylidene(tetramethylcyclopentadienyl)(3-tert-butyl-2-phenoxy)titanium dichloride, isopropylidene(tetramethylcyclopentadienyl)(3-tert-butyl-5-methyl-2-phenoxy)titanium dichloride, isopropylidene(tetramethylcyclopentadienyl)(3-phenyl-2-phenoxy)titanium dichloride, isopropylidene(tetramethylcyclopentadienyl)(3-tert-butyldimethylsilyl-5-methyl-2-phenoxy)titanium dichloride, isopropylidene(tetramethylcyclopentadienyl)(3-trimethylsilyl-5-methyl-2-phenoxy)titanium dichloride, isopropylidene(tetramethylcyclopentadienyl)(3-tert-butyl-5-methoxy-2-phenoxy)titanium dichloride, isopropylidene(tetramethylcyclopentadienyl)(3-tert-butyl-5-chloro-2-phenoxy)titanium dichloride, isopropylidene(trimethylsilylcyclopentadienyl)(3,5-dimethyl-2-phenoxy)titanium dichloride, isopropylidene(trimethylsilylcyclopentadienyl)(3-tert-butyl-2-phenoxy)titanium dichloride, isopropylidene(trimethylsilylcyclopentadienyl)(3-tert-butyl-5-methyl-2-phenoxy)titanium dichloride, isopropylidene(trimethylsilylcyclopentadienyl)(3-phenyl-2-phenoxy)titanium dichloride, isopropylidene(trimethylsilylcyclopentadienyl)(3-tert-butyldimethylsilyl-5-methyl-2-phenoxy)titanium dichloride, isopropylidene(trimethylsilylcyclopentadienyl)(3-trimethylsilyl-5-methyl-2-phenoxy)titanium dichloride, isopropylidene(trimethylsilylcyclopentadienyl)(3-tert-butyl-5-methoxy-2-phenoxy)titanium dichloride, isopropylidene(trimethylsilylcyclopentadienyl)(3-tert-butyl-5-chloro-2-phenoxy)titanium dichloride, isopropylidene(fluorenyl)(3,5-dimethyl-2-phenoxy)titanium dichloride, isopropylidene(fluorenyl)(3-tert-butyl-2-phenoxy)titanium dichloride, isopropylidene(fluorenyl)(3-tert-butyl-5-methyl-2-phenoxy)titanium dichloride, isopropylidene(fluorenyl)(3-phenyl-2-phenoxy)titanium dichloride, isopropylidene(fluorenyl)(3-tert-butyldimethylsilyl-5-methyl-2-phenoxy)titanium dichloride, isopropylidene(fluorenyl)(3-trimethylsilyl-5-methyl-2-phenoxy)titanium dichloride, isopropylidene(fluorenyl)(3-tert-butyl-5-methoxy-2-phenoxy)titanium dichloride, isopropylidene(fluorenyl)(3-tert-butyl-5-chloro-2-phenoxy)titanium dichloride, diphenylmethylene(cyclopentadienyl)(3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethylsilyl-5-methyl-2-phenoxy)titanium dichloride, diphenylmethylene(cyclopentadienyl)(3-trimethylsilyl-5-methyl-2-phenoxy)titanium dichloride, diphenylmethylene(cyclopentadienyl)(3-tert-butyl-5-methoxy-2-phenoxy)titanium dichloride, diphenylmethylene(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene(methylcyclopentadienyl)(3-tert-butyldimethylsilyl-5-methyl-2-phenoxy)titanium dichloride, diphenylmethylene(methylcyclopentadienyl)(3-trimethylsilyl-5-methyl-2-phenoxy)titanium dichloride, diphenylmethylene(methylcyclopentadienyl)(3-tert-butyl-5-methoxy-2-phenoxy)titanium dichloride, diphenylmethylene(methylcyclopentadienyl)(3-tert-butyl-5-chloro-2-phenoxy)titanium dichloride, diphenylmethylene(tert-butylcyclopentadienyl)(3,5-dimethyl-2-phenoxy)titanium dichloride, diphenylmethylene(tert-butylcyclopentadienyl)(3-tert-butyl-2-phenoxy)titanium dichloride, diphenylmethylene(tert-butylcyclopentadienyl)(3-tert-butyl-5-methyl-2-phenoxy)titanium dichloride, diphenylmethylene(tert-butylcyclopentadienyl)(3-phenyl-2-phenoxy)titanium dichloride, diphenylmethylene(tert-butylcyclopentadienyl)(3-tert-butyldimethylsilyl-5-methyl-2-phenoxy)titanium dichloride, diphenylmethylene(tert-butylcyclopentadienyl)(3-trimethylsilyl-5-methyl-2-phenoxy)titanium dichloride, diphenylmethylene(tert-butylcyclopentadienyl)(3-tert-butyl-5-methoxy-2-phenoxy)titanium dichloride, diphenylmethylene(tert-butylcyclopentadienyl)(3-tert-butyl-5-chloro-2-phenoxy)titanium dichloride, diphenylmethylene(tetramethylcyclopentadienyl)(3,5-dimethyl-2-phenoxy)titanium dichloride, diphenylmethylene(tetramethylcyclopentadienyl)(3-tert-butyl-2-phenoxy)titanium dichloride, diphenylmethylene(tetramethylcyclopentadienyl)(3-tert-butyl-5-methyl-2-phenoxy)titanium dichloride, diphenylmethylene(tetramethylcyclopentadienyl)(3-phenyl-2-phenoxy)titanium dichloride, diphenylmethylene(tetramethylcyclopentadienyl)(3-tert-butyldimethylsilyl-5-methyl-2-phenoxy)titanium dichloride, diphenylmethylene(tetramethylcyclopentadienyl)(3-trimethylsilyl-5-methyl-2-phenoxy)titanium dichloride, diphenylmethylene(tetramethylcyclopentadienyl)(3-tert-butyl-5-methoxy-2-phenoxy)titanium dichloride, diphenylmethylene(tetramethylcyclopentadienyl)(3-tert-butyl-5-chloro-2-phenoxy)titanium dichloride, diphenylmethylene(trimethylsilylcyclopentadienyl)(3,5-dimethyl-2-phenoxy)titanium dichloride, diphenylmethylene(trimethylsilylcyclopentadienyl)(3-tert-butyl-2-phenoxy)titanium dichloride, diphenylmethylene(trimethylsilylcyclopentadienyl)(3-tert-butyl-5-methyl-2-phenoxy)titanium dichloride, diphenylmethylene(trimethylsilylcyclopentadienyl)(3-phenyl-2-phenoxy)titanium dichloride, diphenylmethylene(trimethylsilylcyclopentadienyl)(3-tert-butyldimethylsilyl-5-methyl-2-phenoxy)titanium dichloride, diphenylmethylene(trimethylsilylcyclopentadienyl)(3-trimethylsilyl-5-methyl-2-phenoxy)titanium dichloride, diphenylmethylene(trimethylsilylcyclopentadienyl)(3-tert-butyl-5-methoxy-2-phenoxy)titanium dichloride, diphenylmethylene(trimethylsilylcyclopentadienyl)(3-tert-butyl-5-chloro-2-phenoxy)titanium dichloride, diphenylmethylene(fluorenyl)(3,5-dimethyl-2-phenoxy)titanium dichloride, diphenylmethylene(fluorenyl)(3-tert-butyl-2-phenoxy)titanium dichloride, diphenylmethylene(fluorenyl)(3-tert-butyl-5-methyl-2-phenoxy)titanium dichloride, diphenylmethylene(fluorenyl)(3-phenyl-2-phenoxy)titanium dichloride, diphenylmethylene(fluorenyl)(3-tert-butyldimethylsilyl-5-methyl-2-phenoxy)titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride, diphenylmethylene(fluorenyl)(3-tert-butyl-5-chloro-2-phenoxy)titanium dichloride, dimethylsilylene(cyclopentadienyl)(2-phenoxy)titanium dichloride, dimethylsilylene-(cyclopentadienyl)(3-methyl-2-phenoxy)titanium dichloride, dimethylsilylene(cyclopentadienyl)(3,5-dimethyl-2-phenoxy)titanium dichloride, dimethylsilylene(cyclopentadienyl)(3-tert-butyl-2-phenoxy)titanium dichloride, dimethylsilylene(cyclopentadienyl)(3-tert-butyl-5-methyl-2-phenoxy)titanium dichloride, dimethylsilylene(cyclopentadienyl)(3,5-di-tert-butyl-2-phenoxy)titanium dichloride, dimethylsilylene(cyclopentadienyl)(5-methyl-3-phenyl-2-phenoxy)titanium dichloride, dimethylsilylene(cyclopentadienyl)(3-tert-butyldimethylsilyl-5-methyl-2-phenoxy)titanium dichloride, dimethylsilylene(cyclopentadienyl)(5-methyl-3-trimethylsilyl-2-phenoxy)titanium dichloride, dimethylsilylene(cyclopentadienyl)(3-tert-butyl-5-methoxy-2-phenoxy)titanium dichloride, dimethylsilylene(cyclopentadienyl)(3-tert-butyl-5-chloro-2-phenoxy)titanium dichloride, dimethylsilylene(cyclopentadienyl)(3,5-diamyl-2-phenoxy)titanium dichloride, dimethylsilylene(methylcyclopentadienyl)(2-phenoxy)titanium dichloride, dimethylsilylene(methylcyclopentadienyl)(3-methyl-2-phenoxy)titanium dichloride, dimethylsilylene(methylcyclopentadienyl)(3,5-dimethyl-2-phenoxy)titanium dichloride, dimethylsilylene(methylcyclopentadienyl)(3-tert-butyl-2-phenoxy)titanium dichloride, dimethylsilylene(methylcyclopentadienyl)(3-tert-butyl-5-methyl-2-phenoxy)titanium dichloride, dimethylsilylene(methylcyclopentadienyl)(3,5-di-tert-butyl-2-phenoxy)titanium dichloride, dimethylsilylene(methylcyclopentadienyl)(5-methyl-3-phenyl-2-phenoxy)titanium dichloride, dimethylsilylene(methylcyclopentadienyl)(3-tert-butyldimethylsilyl-5-methyl-2-phenoxy)titanium dichloride, dimethylsilylene(methylcyclopentadienyl)(5-methyl-3-trimethylsilyl-2-phenoxy)titanium dichloride, dimethylsilylene(methylcyclopentadienyl)(3-tert-butyl-5-methoxy-2-phenoxy)titanium dichloride, dimethylsilylene(methylcyclopentadienyl)(3-tert-butyl-5-chloro-2-phenoxy)titanium dichloride, dimethylsilylene(methylcyclopentadienyl)(3,5-diamyl-2-phenoxy)titanium dichloride, dimethylsilylene(n-butylcyclopentadienyl)(2-phenoxy)titanium dichloride, dimethylsilylene(n-butylcyclopentadienyl)(3-methyl-2-phenoxy)titanium dichloride, dimethylsilylene(n-butylcyclopentadienyl)(3,5-dimethyl-2-phenoxy)titanium dichloride, dimethylsilylene(n-butylcyclopentadienyl)(3-tert-butyl-2-phenoxy)titanium dichloride, dimethylsilylene(n-butylcyclopentadienyl)(3-tert-butyl-5-methyl-2-phenoxy)titanium dichloride, dimethylsilylene(n-butylcyclopentadienyl)(3,5-di-tert-butyl-2-phenoxy)titanium dichloride, dimethylsilylene(n-butylcyclopentadienyl)(5-methyl-3-phenyl-2-phenoxy)titanium dichloride, dimethylsilylene(n-butylcyclopentadienyl)(3-tert-butyldimethylsilyl-5-methyl-2-phenoxy)titanium dichloride, dimethylsilylene(n-butylcyclopentadienyl)(5-methyl-3-trimethylsilyl-2-phenoxy)titanium dichloride, dimethylsilylene(n-butylcyclopentadienyl)(3-tert-butyl-5-methoxy-2-phenoxy)titanium dichloride, dimethylsilylene(n-butylcyclopentadienyl)(3-tert-butyl-5-chloro-2-phenoxy)titanium dichloride, dimethylsilylene(n-butylcyclopentadienyl)(3,5-diamyl-2-phenoxy)titanium dichloride, dimethylsilylene(tert-butylcyclopentadienyl)(2-phenoxy)titanium dichloride, dimethylsilylene(tert-butylcyclopentadienyl)(3-methyl-2-phenoxy)titanium dichloride, dimethylsilylene(tert-butylcyclopentadienyl)(3,5-dimethyl-2-phenoxy)titanium dichloride, dimethylsilylene(tert-butylcyclopentadienyl)(3-tert-butyl-2-phenoxy)titanium dichloride, dimethylsilylene(tert-butylcyclopentadienyl)(3-tert-butyl-5-methyl-2-phenoxy)titanium dichloride, dimethylsilylene(tert-butylcyclopentadienyl)(3,5-di-tert-butyl-2-phenoxy)titanium dichloride, dimethylsilylene(tert-butylcyclopentadienyl)(5-methyl-3-phenyl-2-phenoxy)titanium dichloride, dimethylsilylene(tert-butylcyclopentadienyl)(3-tert-butyldimethylsilyl-5-methyl-2-phenoxy)titanium dichloride, dimethylsilylene(tert-butylcyclopentadienyl)(5-methyl-3-trimethylsilyl-2-phenoxy)titanium dichloride, dimethylsilylene(tert-butylcyclopentadienyl)(3-tert-butyl-5-methoxy-2-phenoxy)titanium dichloride, dimethylsilylene(tert-butylcyclopentadienyl)(3-tert-butyl-5-chloro-2-phenoxy)titanium dichloride, dimethylsilylene(tert-butylcyclopentadienyl)(3,5-diamyl-2-phenoxy)titanium dichloride, dimethylsilylene(tetramethylcyclopentadienyl)(2-phenoxy)titanium dichloride, dimethylsilylene(tetramethylcyclopentadienyl)(3-methyl-2-phenoxy)titanium dichloride, dimethylsilylene(tetramethylcyclopentadienyl)(3,5-dimethyl-2-phenoxy)titanium dichloride, dimethylsilylene(tetramethylcyclopentadienyl)(3-tert-butyl-2-phenoxy)titanium dichloride, dimethylsilylene(tetramethylcyclopentadienyl)(3-tert-butyl-5-methyl-2-phenoxy)titanium dichloride, dimethylsilylene(tetramethylcyclopentadienyl)(3,5-di-tert-butyl-2-phenoxy)titanium dichloride, dimethylsilylene(tetramethylcyclopentadienyl)(5-methyl-3-phenyl-2-phenoxy)titanium dichloride, dimethylsilylene(tetramethylcyclopentadienyl)(3-tert-butyldimethylsilyl-5-methyl-2-phenoxy)titanium dichloride, dimethylsilylene(tetramethylcyclopentadienyl)(5-methyl-3-trimethylsilyl-2-phenoxy)titanium dichloride, dimethylsilylene(tetramethylcyclopentadienyl)(3-tert-butyl-5-methoxy-2-phenoxy)titanium dichloride, dimethylsilylene(tetramethylcyclopentadienyl)(3-tert-butyl-5-chloro-2-phenoxy)titanium dichloride, dimethylsilylene(tetramethylcyclopentadienyl)(3,5-diamyl-2-phenoxy)titanium dichloride, dimethylsilylene(trimethylsilylcyclopentadienyl)(2-phenoxy)titanium dichloride, dimethylsilylene(trimethylsilylcyclopentadienyl)(3-methyl-2-phenoxy)titanium dichloride, dimethylsilylene(trimethylsilylcyclopentadienyl)(3,5-dimethyl-2-phenoxy)titanium dichloride, dimethylsilylene(trimethylsilylcyclopentadienyl)(3-tert-butyl-2-phenoxy)titanium dichloride, dimethylsilylene(trimethylsilylcyclopentadienyl)(3-tert-butyl-5-methyl-2-phenoxy)titanium dichloride, dimethylsilylene(trimethylsilylcyclopentadienyl)(3,5-di-tert-butyl-2-phenoxy)titanium dichloride, dimethylsilylene(trimethylsilylcyclopentadienyl)(5-methyl-3-phenyl-2-phenoxy)titanium dichloride, dimethylsilylene(trimethylsilylcyclopentadienyl)(3-tert-butyldimethylsilyl-5-methyl-2-phenoxy)titanium dichloride, dimethylsilylene(trimethylsilylcyclopentadienyl)(5-methyl-3-trimethylsilyl-2-phenoxy)titanium dichloride, dimethylsilylene(trimethylsilylcyclopentadienyl)(3-tert-butyl-5-methoxy-2-phenoxy)titanium dichloride, dimethylsilylene(trimethylsilylcyclopentadienyl)(3-tert-butyl-5-chloro-2-phenoxy)titanium dichloride, dimethylsilylene(trimethylsilylcyclopentadienyl)(3,5-diamyl-2-phenoxy)titanium dichloride, dimethylsilylene(indenyl)(2-phenoxy)titanium dichloride, dimethylsilylene(indenyl)(3-methyl-2-phenoxy)titanium dichloride, dimethylsilylene(indenyl)(3,5-dimethyl-2-phenoxy)titanium dichloride, dimethylsilylene(indenyl)(3-tert-butyl-2-phenoxy)titanium dichloride, dimethylsilylene(indenyl)(3-tert-butyl-5-methyl-2-phenoxy)titanium dichloride, dimethylsilylene(indenyl)(3,5-di-tert-butyl-2-phenoxy)titanium dichloride, dimethylsilylene(indenyl)(5-methyl-3-phenyl-2-phenoxy) titanium dichloride, dimethylsilylene(indenyl)(3-tert-butyldimethylsilyl-5-methyl-2-phenoxy)titanium dichloride, dimethylsilylene(indenyl)(5-methyl-3-trimethylsilyl-2-phenoxy)titanium dichloride, dimethylsilylene(indenyl)(3-tert-butyl-5-methoxy-2-phenoxy)titanium dichloride, dimethylsilylene(indenyl)(3-tert-butyl-5-chloro-2-phenoxy)titanium dichloride, dimethylsilylene(indenyl)(3,5-diamyl-2-phenoxy)titanium dichloride, dimethylsilylene(fluorenyl)(2-phenoxy)titanium dichloride, dimethylsilylene(fluorenyl)(3-methyl-2-phenoxy)titanium dichloride, dimethylsilylene(fluorenyl)(3,5-dimethyl-2-phenoxy)titanium dichloride, dimethylsilylene(fluorenyl)(3-tert-butyl-2-phenoxy) titanium dichloride, dimethylsilylene(fluorenyl)(3-tert-butyl-5-methyl-2-phenoxy)titanium dichloride, dimethylsilylene(fluorenyl)(3,5-di-tert-butyl-2-phenoxy) titanium dichloride, dimethylsilylene(fluorenyl)(5-methyl-3-phenyl-2-phenoxy)titanium dichloride, dimethylsilylene (fluorenyl)(3-tert-butyldimethylsilyl-5-methyl-2-phenoxy) titanium dichloride, dimethylsilylene(fluorenyl)(5-methyl-3-trimethylsilyl-2-phenoxy)titanium dichloride, dimethylsilylene(fluorenyl)(3-tert-butyl-5-methoxy-2-phenoxy)titanium dichloride, dimethylsilylene(fluorenyl)(3-tert-butyl-5-chloro-2-phenoxy)titanium dichloride, dimethylsilylene(fluorenyl)(3,5-diamyl-2-phenoxy)titanium dichloride, dimethylsilylene(tetramethylcyclopentadienyl) (1-naphthox-2-yl)titanium dichloride and the like, and compounds wherein (2-phenoxy) of these compounds is replaces with (3-phenyl-2-phenoxy), (3-trimethylsilyl-2-phenoxy) or (3-tert-butyldimethylsilyl-2-phenoxy), compounds wherein dimethylsilylene of these compounds is replaced with diethylsilylene, diphenylsilylene or dimethoxysilylene, compounds wherein dichloride of these compounds is replaced with difluoride, dibromide, diiodide, dimethyl, diethyl, diisopropyl, bis(dimethylamido), bis(diethylamido), dimethoxide, diethoxide, di-n-butoxide or diisopropoxide. (tert-butylamido)tetramethylcyclopentadienyl-1,2-ethanediyltitanium dichloride, (tert-butylamido) tetramethylcyclopentadienyl-1,2-ethanediyltitanium dimethyl, (tert-butylamido)tetramethylcyclopentadienyl-1, 2-ethanediyltitanium dibenzyl, (methylamido) tetramethylcyclopentadienyl-1,2-ethanediyltitanium dichloride, (ethylamido)tetramethylcyclopentadienyl-1,2-ethanediyltitanium dichloride, (tert-butylamido) tetramethylcyclopentadienyldimethylsilanetitanium dichloride, (tert-butylamido) tetramethylcyclopentadienyldimethylsilanetitanium dimethyl, (tert-butylamido) tetramethylcyclopentadienyldimethylsilane-titanium dibenzyl, (benzylamido)tetramethylcyclopentadienyl-dimethylsilanetitanium dichloride, (phenylphosphido) tetramethylcyclopentadienyldimethyl-silanetitanium dibenzyl, (tert-butylamido)indenyl-1,2-ethanediyltitanium dichloride, (tert-butylamido)indenyl-1,2-ethanediyltitanium dimethyl, (tert-butylamido)tetrahydroindenyl-1,2-ethanediyltitanium dichloride, (tert-butylamido) tetrahydroindenyl-1,2-ethanediyltitanium dimethyl, (tert-butylamido)fluorenyl-1,2-ethanediyltitanium dichloride, (tert-butylamido)fluorenyl-1,2-ethanediyltitanium dimethyl, (tert-butylamido)indenyldimethylsilanetitanium dichloride, (tert-butylamido)indenyldimethylsilanetitanium dimethyl, (tert-butylamido)tetrahydroindenyldimethylsilanetitanium dichloride, (tert-butylamido) tetrahydroindenyldimethylsilanetitanium dimethyl, (tert-butylamido)fluorenyldimethylsilanetitanium dichloride, (tert-butylamido)fluorenyldimethylsilanetitanium dimethyl, (dimethylaminomethyl)tetramethylcyclopenta-dienyltitanium(III) dichloride, (dimethylaminoethyl) tetramethylcyclopentadienyltitanium(III) dichloride, (dimethylaminopropyl)tetramethylcyclopenta-dienyltitanium(III) dichloride, (N-pyrrolidinylethyl) tetramethylcyclopentadienyltitanium dichloride, (B-dimethylaminoborabenzene)cyclopentadienylzirconium dichloride, cyclopentadienyl(9-mesitylboraanthracenyl) zirconium dichloride, 2,2'-thiobis[4-methyl-6-(1-methylethyl)phenoxy]titanium dichloride, 2,2'-thiobis[4,6-dimethylphenoxy]titanium dichloride, 2,2'-thiobis(4-methyl-6-tert-butylphenoxy)titanium dichloride, 2,2'-methylenebis(4-methyl-6-tert-butylphenoxy)titanium dichloride, 2,2'-ethylenebis(4-methyl-6-tert-butylphenoxy) titanium dichloride, 2,2'-sulfinylbis(4-methyl-6-tert-butylphenoxy)titanium dichloride, 2,2'-(4,4',6,6'-tetra-tert-butyl-1,1'-biphenoxy)titanium dichloride, 2,2'-thiobis[4-methyl-6-tert-butylphenoxy]titanium diisopropoxide, 2,2'-methylenebis(4-methyl-6-tert-butylphenoxy)titanium diisopropoxide, 2,2'-ethylenebis(4-methyl-6-tert-butylphenoxy)titanium diisopropoxide, 2,2'-sulfinylbis(4-methyl-6-tert-butylphenoxy)titanium diisopropoxide, (di-tert-butyl-1,3-propanediamido)titanium dichloride, (dicyclohexyl-1,3-propanediamido)titanium dichloride, [bis (trimethylsilyl)-1,3-propanediamido]titanium dichloride, [bis(tert-butyldimethylsilyl)-1,3-propanediamido]titanium dichloride, [bis(2,6-dimethylphenyl)-1,3-propanediamido] titanium dichloride, [bis(2,6-diisopropylphenyl)-1,3-propanediamido]titanium dichloride, [bis(2,6-di-tert-butylphenyl)-1,3-propanediamido]titanium dichloride, [bis (triisopropylsilyl)naphthalenediamido]titanium dichloride, [bis(trimethylsilyl)naphthalenediamido]titanium dichloride, [bis(tert-butyldimethylsilyl)naphthalenediamido]titanium dichloride, [bis(tert-butyldimethylsilyl) naphthalenediamido]titanium dibromide, [hydrotris(3,5-dimethylpyrazolyl)borate]titanium trichloride, [hydrotris(3, 5-dimethylpyrazolyl)borate]titanium tribromide, [hydrotris (3,5-dimethylpyrazolyl)borate]titanium triiodide, [hydrotris (3,5-diethylpyrazolyl)borate]titanium trichloride, [hydrotris (3,5-diethylpyrazolyl)borate]titanium tribromide, [hydrotris (3,5-diethylpyrazolyl)borate]titanium triiodide, [hydrotris (3,5-di-tert-butylpyrazolyl)borate]titanium trichloride, [hydrotris(3,5-di-tert-butylpyrazolyl)borate]titanium tribromide, [hydrotris(3,5-di-tert-butylpyrazolyl)borate] titanium triiodide, [tris(3,5-dimethylpyrazolyl)methyl] titanium trichloride, [tris(3,5-dimethylpyrazolyl)methyl] titanium tribromide, [tris(3,5-dimethylpyrazolyl)methyl] titanium triiodide, [tris(3,5-diethylpyrazolyl)methyl] titanium trichloride, [tris(3,5-diethylpyrazolyl)methyl] titanium tribromide, [tris(3,5-diethylpyrazolyl)methyl] titanium triiodide, [tris(3,5-di-tert-butylpyrazolyl)methyl] titanium trichloride, [tris(3,5-di-tert-butylpyrazolyl)methyl] titanium tribromide, [tris(3,5-di-tert-butylpyrazolyl)methyl] titanium triiodide, μ-oxobis{isopropylidene (cyclopentadienyl)(2-phenoxy)titanium chloride}, μ-oxobis{isopropylidene(cyclopentadienyl)(2-phenoxy) titanium methoxide}, μ-oxobis{isopropylidene (cyclopentadienyl)(3-tert-butyl-5-methyl-2-phenoxy) titanium chloride}, μ-oxobis{isopropylidene (cyclopentadienyl)(3-tert-butyl-5-methyl-2-phenoxy) titanium methoxide}, μ-oxobis{isopropylidene (methylcyclopentadienyl)(2-phenoxy)titanium chloride}, μ-oxobis{isopropylidene(methylcyclopentadienyl)(2-phenoxy)titanium methoxide}, μ-oxobis{isopropylidene (methylcyclopentadienyl)(3-tert-butyl-5-methyl-2-phenoxy)titanium chloride}, μ-oxobis{isopropylidene (methylcyclopentadienyl)(3-tert-butyl-5-methyl-2- phenoxy)titanium methoxide}, μ-oxobis{isopropylidene (tetramethylcyclopentadienyl)(2-phenoxy)titanium chloride}, μ-oxobis{isopropylidene (tetramethylcyclopentadienyl)(2-phenoxy)titanium methoxide}, μ-oxobis{isopropylidene (tetramethylcyclopentadienyl)(3-tert-butyl-5-methyl-2-phenoxy)titanium chloride}, μ-oxobis{isopropylidene (tetramethylcyclopentadienyl)(3-tert-butyl-5-methyl-2-phenoxy)titanium methoxide}, μ-oxobis{dimethylsilylene (cyclopentadienyl)(2-phenoxy)titanium chloride}, μ-oxobis{dimethylsilylene(cyclopentadienyl)(2-phenoxy) titanium methoxide}, μ-oxobis{dimethylsilylene (cyclopentadienyl)(3-tert-butyl-5-methyl-2-phenoxy) titanium chloride}, μ-oxobis{dimethylsilylene (cyclopentadienyl)(3-tert-butyl-5-methyl-2-phenoxy) titanium methoxide}, μ-oxobis{dimethylsilylene (methylcyclopentadienyl)(2-phenoxy)titanium chloride}, μ-oxobis{dimethylsilylene(methylcyclopentadienyl)(2-phenoxy)titanium methoxide}, μ-oxobis{dimethylsilylene (methylcyclopentadienyl)(3-tert-butyl-5-methyl-2-phenoxy)titanium chloride}, μ-oxobis{dimethylsilylene (methylcyclopentadienyl)(3-tert-butyl-5-methyl-2-phenoxy)titanium methoxide}, μ-oxobis{dimethylsilylene (tetramethylcyclopentadienyl)(2-phenoxy)titanium chloride}, μ-oxobis{dimethylsilylene (tetramethylcyclopentadienyl)(2-phenoxy)titanium methoxide}, μ-oxobis{dimethylsilylene (tetramethylcyclopentadienyl)(3-tert-butyl-5-methyl-2-phenoxy)titanium chloride}, μ-oxobis{dimethylsilylene (tetramethylcyclopentadienyl)(3-tert-butyl-5-methyl-2-phenoxy)titanium methoxide}di-μ-oxobis[isopropylidene (cyclopentadienyl)(2-phenoxy)titanium], di-μ-oxobis [isopropylidene(cyclopentadienyl)(3-tert-butyl-5-methyl-2-phenoxy)titanium], di-μ-oxobis[isopropylidene (methylcyclopentadienyl)(2-phenoxy)titanium], di-μ-oxobis [isopropylidene(methylcyclopentadienyl)(3-tert-butyl-5-methyl-2-phenoxy)titanium], di-μ-oxobis[isopropylidene (tetramethylcyclopentadienyl)(2-phenoxy)titanium], di-μ-oxobis[isopropylidene(tetramethylcyclopentadienyl)(3-tert-butyl-5-methyl-2-phenoxy)titanium], di-μ-oxobis [dimethylsilylene(cyclopentadienyl)(2-phenoxy)titanium], di-μ-oxobis[dimethylsilylene(cyclopentadienyl)(3-tert-butyl-5-methyl-2-phenoxy)titanium], di-μ-oxobis [dimethylsilylene(methylcyclopentadienyl)(2-phenoxy) titanium], di-μ-oxobis[dimethylsilylene (methylcyclopentadienyl)(3-tert-butyl-5-methyl-2-phenoxy)titanium], di-μ-oxobis[dimethylsilylene (tetramethylcyclopentadienyl)(2-phenoxy)titanium], di-μ-oxobis[dimethylsilylene(tetramethylcyclopentadienyl)(3-tert-butyl-5-methyl-2-phenoxy)titanium] and the like.

Further, compounds wherein a titanium atom is replaced with a zirconium atom or a hafnium atom can be similarly exemplified in the above-mentioned titanium compounds. Among the transition metal compounds, specific examples of a compound in which a transition metal atom is a vanadium atom include vanadium acetylacetonate, vanadium tetrachloride, vanadium oxy trichloride and the like.

Among the transition metal compounds, specific examples of a compound in which a transition metal atom is a samarium atom include bis(pentamethylcyclopentadienyl) samarium methyltetrahydrofuran and the like.

Among the transition metal compounds, specific examples of a compound in which a transition metal atom is an ytterbium atom include bis (pentamethylcyclopentadienyl)ytterbium methyltetrahydrofuran and the like.

Among the transition metal compounds, specific examples of a compound in which a transition metal atom is a nickel atom include 2,2'-methylenebis[(4R)-4-phenyl-5,5'-dimethyloxazoline]nickel dichloride, 2,2'-methylenebis [(4R)-4-phenyl-5,5'-dimethyloxazoline]nickel dibromide, 2,2'-methylenebis[(4R)-4-phenyl-5,5'-diethyloxazoline] nickel dichloride, 2,2'-methylenebis[(4R)-4-phenyl-5,5'-diethyloxazoline]nickel dibromide, 2,2'-methylenebis[(4R)-4-phenyl-5,5'-di-n-propyloxazoline]nickel dichloride, 2,2'-methylenebis[(4R)-4-phenyl-5,5'-di-n-propyloxazoline] nickel dibromide, 2,2'-methylenebis[(4R)-4-phenyl-5,5'-diisopropyloxazoline]nickel dichloride, 2,2'-methylenebis [(4R)-4-phenyl-5,5'-diisopropyloxazoline]nickel dibromide, 2,2'-methylenebis[(4R)-4-phenyl-5,5'-dicyclohexyloxazoline]nickel dichloride, 2,2'-methylenebis [(4R)-4-phenyl-5,5'-dicyclohexyloxazoline]nickel dibromide, 2,2'-methylenebis[(4R)-4-phenyl-5,5'-dimethoxyoxazoline]nickel dichloride, 2,2'-methylenebis [(4R)-4-phenyl-5,5'-dimethoxyoxazoline]nickel dibromide, 2,2'-methylenebis[(4R)-4-phenyl-5,5'-diethoxyoxazoline] nickel dichloride, 2,2'-methylenebis[(4R)-4-phenyl-5,5'-diethoxyoxazoline]nickel dibromide, 2,2'-methylenebis [(4R)-4-phenyl-5,5'-diphenyloxazoline]nickel dichloride, 2,2'-methylenebis[(4R)-4-phenyl-5,5'-diphenyloxazoline] nickel dibromide, methylenebis[(4R)-4-methyl-5,5'-di-(2-methylphenyl)oxazoline]nickel dibromide, methylenebis [(4R)-4-methyl-5,5'-di-(3-methylphenyl)oxazoline]nickel dibromide, methylenebis[(4R)-4-methyl-5,5'-di-(4-methylphenyl)oxazoline]nickel dibromide, methylenebis [(4R)-4-methyl-5,5'-di-(2-methoxyphenyl)oxazoline]nickel dibromide, methylenebis[(4R)-4-methyl-5,5'-di-(3-methoxyphenyl)oxazoline]nickel dibromide, methylenebis [(4R)-4-methyl-5,5'-di-(4-methoxyphenyl)oxazoline]nickel dibromide, methylenebis[spiro{(4R)-4-methyloxazoline-5,1'-cyclobutane}]nickel dibromide, methylenebis[spiro{ (4R)-4-methyloxazoline-5,1'-cyclopentane}]nickel dibromide, methylenebis[spiro{(4R)-4-methyloxazoline-5, 1'-cyclohexane}]nickel dibromide, methylenebis[spiro{ (4R)-4-methyloxazoline-5,1'-cycloheptane}]nickel dibromide, 2,2'-methylenebis[(4R)-4-isopropyl-5,5-dimethyloxazoline]nickel dibromide, 2,2'-methylenebis [(4R)-4-isopropyl-5,5-diethyloxazoline]nickel dibromide, 2,2'-methylenebis[(4R)-4-isopropyl-5,5-di-n-propyloxazoline]nickel dibromide, methylenebis[(4R)-4-isopropyl-5,5-diisopropyloxazoline]nickel dibromide, 2,2'-methylenebis[(4R)-4-isopropyl-5,5-dicyclohexyloxazoline] nickel dibromide, 2,2'-methylenebis[(4R)-4-isopropyl-5,5-diphenyloxazoline]nickel dibromide, 2,2'-methylenebis [(4R)-4-isopropyl-5,5-di-(2-methylphenyl)oxazoline]nickel dibromide, 2,2'-methylenebis[(4R)-4-isopropyl-5,5-di-(3-methylphenyl)oxazoline]nickel dibromide, 2,2'-methylenebis[(4R)-4-isopropyl-5,5-di-(4-methylphenyl) oxazoline]nickel dibromide, 2,2'-methylenebis[(4R)-4-isopropyl-5,5-di-(2-methoxyphenyl)oxazoline]nickel dibromide, 2,2'-methylenebis[(4R)-4-isopropyl-5,5-di-(3-methoxyphenyl)oxazoline]nickel dibromide, 2,2'-methylenebis[(4R)-4-isopropyl-5,5-di-(4-methoxyphenyl) oxazoline]nickel dibromide, 2,2'-methylenebis[spiro{(4R)-4-isopropyloxazoline-5,1'-cyclobutane}]nickel dibromide, 2,2'-methylenebis[spiro{(4R)-4-isopropyloxazoline-5,1'-cyclopentane}]nickel dibromide, 2,2'-methylenebis[spiro{ (4R)-4-isopropyloxazoline-5,1'-cyclohexane}]nickel dibromide, 2,2'-methylenebis[spiro{(4R)-4-isopropyloxazoline-5,1'-cycloheptane}]nickel dibromide, 2,2'-methylenebis[(4R)-4-isobutyl-5,5-dimethyloxazoline] nickel dibromide, 2,2'-methylenebis[(4R)-4-isobutyl-5,5-diethyloxazoline]nickel dibromide, 2,2'-methylenebis[(4R)-4-isobutyl-5,5-di-n-propyloxazoline]nickel dibromide, 2,2'-methylenebis[(4R)-4-isobutyl-5,5-diisopropyloxazoline]

nickel dibromide, 2,2'-methylenebis[(4R)-4-isobutyl-5,5-dicyclohexyloxazoline]nickel dibromide, 2,2'-methylenebis[(4R)-4-isobutyl-5,5-diphenyloxazoline]nickel dibromide, 2,2'-methylenebis[(4R)-4-isobutyl-5,5-di-(2-methylphenyl)oxazoline]nickel dibromide, 2,2'-methylenebis[(4R)-4-isobutyl-5,5-di-(3-methylphenyl)oxazoline]nickel dibromide, 2,2'-methylenebis[(4R)-4-isobutyl-5,5-di-(4-methylphenyl)oxazoline]nickel dibromide, 2,2'-methylenebis[(4R)-4-isobutyl-5,5-di-(2-methoxyphenyl)oxazoline]nickel dibromide, 2,2'-methylenebis[(4R)-4-isobutyl-5,5-di-(3-methoxyphenyl)oxazoline]nickel dibromide, 2,2'-methylenebis[(4R)-4-isobutyl-5,5-di-(4-methoxyphenyl)oxazoline]nickel dibromide, 2,2'-methylenebis[spiro{(4R)-4-isobutyloxazoline-5,1'-cyclobutane}]nickel dibromide, 2,2'-methylenebis[spiro{(4R)-4-isobutyloxazoline-5,1'-cyclopentane}]nickel dibromide, 2,2'-methylenebis[spiro{(4R)-4-isobutyloxazoline-5,1'-cyclohexane}]nickel dibromide, 2,2'-methylenebis[spiro{(4R)-4-isobutyloxazoline-5,1'-cycloheptane}]nickel dibromide, 2,2'-methylenebis[(4R)-4-tert-butyl-5,5-dimethyloxazoline]nickel dibromide, 2,2'-methylenebis[(4R)-4-tert-butyl-5,5-diethyloxazoline]nickel dibromide, 2,2'-methylenebis[(4R)-4-tert-butyl-5,5-di-n-propyloxazoline]nickel dibromide, 2,2'-methylenebis[(4R)-4-tert-butyl-5,5-diisopropyloxazoline]nickel dibromide, 2,2'-methylenebis[(4R)-4-tert-butyl-5,5-diphenyloxazoline]nickel dibromide, 2,2'-methylenebis[(4R)-4-tert-butyl-5,5-dicyclohexyloxazoline]nickel dibromide, 2,2'-methylenebis[(4R)-4-tert-butyl-5,5-di-(2-methylphenyl)oxazoline]nickel dibromide, 2,2'-methylenebis[(4R)-4-tert-butyl-5,5-di-(3-methylphenyl)oxazoline]nickel dibromide, 2,2'-methylenebis[(4R)-4-tert-butyl-5,5-di-(4-methylphenyl)oxazoline]nickel dibromide, 2,2'-methylenebis[(4R)-4-tert-butyl-5,5-di-(2-methoxyphenyl)oxazoline]nickel dibromide, 2,2'-methylenebis[(4R)-4-tert-butyl-5,5-di-(3-methoxyphenyl)oxazoline]nickel dibromide, 2,2'-methylenebis[(4R)-4-tert-butyl-5,5-di-(4-methoxyphenyl)oxazoline]nickel dibromide, 2,2'-methylenebis[spiro{(4R)-4-tert-butyloxazoline-5,1'-cyclobutane}]nickel dibromide, 2,2'-methylenebis[spiro{(4R)-4-tert-butyloxazoline-5,1'-cyclopentane}]nickel dibromide, 2,2'-methylenebis[spiro{(4R)-4-tert-butyloxazoline-5,1'-cyclohexane}]nickel dibromide, 2,2'-methylenebis[spiro{(4R)-4-tert-butyloxazoline-5,1'-cycloheptane}]nickel dibromide, 2,2'-methylenebis[(4R)-4-phenyl-5,5-dimethyloxazoline]nickel dibromide, 2,2'-methylenebis[(4R)-4-phenyl-5,5-diethyloxazoline]nickel dibromide, 2,2'-methylenebis[(4R)-4-phenyl-5,5-di-n-propyloxazoline]nickel dibromide, 2,2'-methylenebis[(4R)-4-phenyl-5,5-diisopropyloxazoline]nickel dibromide, 2,2'-methylenebis[(4R)-4-phenyl-5,5-dicyclohexyloxazoline]nickel dibromide, 2,2'-methylenebis[(4R)-4-phenyl-5,5-diphenyl)oxazoline]nickel dibromide, 2,2'-methylenebis[(4R)-4-phenyl-5,5-di-(2-methylphenyl)oxazoline]nickel dibromide, 2,2'-methylenebis[(4R)-4-phenyl-5,5-di-(3-methylphenyl)oxazoline]nickel dibromide, 2,2'-methylenebis[(4R)-4-phenyl-5,5-di-(4-methylphenyl)oxazoline]nickel dibromide, 2,2'-methylenebis[(4R)-4-phenyl-5,5-di-(2-methoxyphenyl)oxazoline]nickel dibromide, 2,2'-methylenebis[(4R)-4-phenyl-5,5-di-(3-methoxyphenyl)oxazoline]nickel dibromide, 2,2'-methylenebis[(4R)-4-phenyl-5,5-di-(4-methoxyphenyl)oxazoline]nickel dibromide, methylenebis[spiro{(4R)-4-phenyloxazoline-5,1'-cyclobutane}]nickel dibromide, 2,2'-methylenebis[spiro{(4R)-4-phenyloxazoline-5,1'-cyclopentane}]nickel dibromide, 2,2'-methylenebis[spiro{(4R)-4-phenyloxazoline-5,1'-cyclohexane}]nickel dibromide, 2,2'-methylenebis[spiro{(4R)-4-phenyloxazoline-5,1'-cycloheptane}]nickel dibromide, 2,2'-methylenebis[(4R)-4-benzyl-5,5-dimethyloxazoline]nickel dibromide, 2,2'-methylenebis[(4R)-4-benzyl-5,5-diethyloxazoline]nickel dibromide, 2,2'-methylenebis[(4R)-4-benzyl-5,5-di-n-propyloxazoline]nickel dibromide, 2,2'-methylenebis[(4R)-4-benzyl-5,5-diisopropyloxazoline]nickel dibromide, 2,2'-methylenebis[(4R)-4-benzyl-5,5-dicyclohexyloxazoline]nickel dibromide, 2,2'-methylenebis[(4R)-4-benzyl-5,5-diphenyl)oxazoline]nickel dibromide, 2,2'-methylenebis[(4R)-4-benzyl-5,5-di-(2-methylphenyl)oxazoline]nickel dibromide, 2,2'-methylenebis[(4R)-4-benzyl-5,5-di-(3-methylphenyl)oxazoline]nickel dibromide, 2,2'-methylenebis[(4R)-4-benzyl-5,5-di-(4-methylphenyl)oxazoline]nickel dibromide, 2,2'-methylenebis[(4R)-4-benzyl-5,5-di-(2-methoxyphenyl)oxazoline]nickel dibromide, 2,2'-methylenebis[(4R)-4-benzyl-5,5-di-(3-methoxyphenyl)oxazoline]nickel dibromide, 2,2'-methylenebis[(4R)-4-benzyl-5,5-di-(4-methoxyphenyl)oxazoline]nickel dibromide, 2,2'-methylenebis[spiro{(4R)-4-benzyloxazoline-5,1'-cyclobutane}]nickel dibromide, 2,2'-methylenebis[spiro{(4R)-4-benzyloxazoline-5,1'-cyclopentane}]nickel dibromide, 2,2'-methylenebis[spiro{(4R)-4-benzyloxazoline-5,1'-cyclohexane}]nickel dibromide, 2,2'-methylenebis[spiro{(4R)-4-benzyloxazoline-5,1'-cycloheptane}]nickel dibromide, and compounds in which (4R) in each of the above-mentioned compounds corresponds to (4S), etc. Further, examples of the meso type isomer include compounds in which (4R) of two skeletons in each of the compounds which are mentioned above as the optically active substances of bisoxazolines were changed to (4R) of one oxazoline skeleton and (4S) of another oxazoline skeleton, and [hydrotris(3,5-dimethylpyrazolyl)borate]nickel chloride, [hydrotris(3,5-dimethylpyrazolyl)borate]nickel bromide, [hydrotris(3,5-dimethylpyrazolyl)borate]nickel iodide, [hydrotris(3,5-dimethylpyrazolyl)borate]nickel methyl, [hydrotris(3,5-dimethylpyrazolyl)borate]nickel ethyl, [hydrotris(3,5-dimethylpyrazolyl)borate]nickel allyl, [hydrotris(3,5-dimethylpyrazolyl)borate]nickel methallyl, [hydrotris(3,5-diethylpyrazolyl)borate]nickel chloride, [hydrotris(3,5-diethylpyrazolyl)borate]nickel bromide, [hydrotris(3,5-diethylpyrazolyl)borate]nickel iodide, [hydrotris (3,5-diethylpyrazolyl) borate]nickel methyl, [hydrotris(3,5-diethylpyrazolyl)borate]nickel ethyl, [hydrotris(3,5-diethylpyrazolyl)borate]nickel allyl, [hydrotris(3,5-diethylpyrazolyl)borate]nickel methallyl, [hydrotris(3,5-di-tert-butylpyrazolyl)borate]nickel chloride, [hydrotris(3,5-di-tert-butylpyrazolyl)borate]nickel bromide, [hydrotris(3,5-di-tert-butylpyrazolyl)borate]nickel iodide, [hydrotris(3,5-di-tert-butylpyrazolyl)borate]nickel methyl, [hydrotris(3,5-di-tert-butylpyrazolyl)borate]nickel ethyl, [hydrotris(3,5-di-tert-butylpyrazolyl)borate]nickel allyl, [hydrotris(3,5-di-tert-butylpyrazolyl)borate]nickel methallyl, compounds indicated by the structural formula described below:

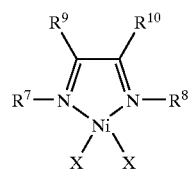

(wherein each of $R^7$ and $R^8$ is a 2,6-diisopropylphenyl group, and X, $R^9$ and $R^{10}$ are any one of the combination of the substituents represented in Table 1 described below.) $R^9$ and $R^{10}$ may be one bi-valent group (e.g. a acenaphthyl group) in one united body.

TABLE 1

| | | |
|---|---|---|
| $R^9 = R^{10} = H$ | $R^9 = R^{10}$ = methyl | Acenaphthyl by $R^9$ & $R^{10}$ |
| X = F | X = F | X = F |
| $R^9 = R^{10} = H$ | $R^9 = R^{10}$ = methyl | Acenaphthyl by $R^9$ & $R^{10}$ |
| X = Cl | X = Cl | X = Cl |
| $R^9 = R^{10} = H$ | $R^9 = R^{10}$ = methyl | Acenaphthyl by $R^9$ & $R^{10}$ |
| X = I | X = I | X = I |
| $R^9 = R^{10} = H$ | $R^9 = R^{10}$ = methyl | Acenaphthyl by $R^9$ & $R^{10}$ |
| X = Methyl | X = methyl | X = methyl |
| $R^9 = R^{10} = H$ | $R^9 = R^{10}$ = methyl | Acenaphthyl by $R^9$ & $R^{10}$ |
| X = Ethyl | X = ethyl | X = ethyl |
| $R^9 = R^{10} = H$ | $R^9 = R^{10}$ = methyl | Acenaphthyl by $R^9$ & $R^{10}$ |
| X = n-propyl | X = n-propyl | X = n-propyl |
| $R^9 = R^{10} = H$ | $R^9 = R^{10}$ = methyl | Acenaphthyl by $R^9$ & $R^{10}$ |
| X = isopropyl | X = isopropyl | X = isopropyl |
| $R^9 = R^{10} = H$ | $R^9 = R^{10}$ = methyl | Acenaphthyl by $R^9$ & $R^{10}$ |
| X = n-butyl | X = n-butyl | X = n-butyl |
| $R^9 = R^{10} = H$ | $R^9 = R^{10}$ = methyl | Acenaphthyl by $R^9$ & $R^{10}$ |
| X = phenyl | X = phenyl | X = phenyl |
| $R^9 = R^{10} = H$ | $R^9 = R^{10}$ = methyl | Acenaphthyl by $R^9$ & $R^{10}$ |
| X = benzyl | X = benzyl | X = benzyl |

Further, compounds wherein a nickel atom is replaced with a palladium atom, a cobalt atom, a rhodium atom or a ruthenium atom can be similarly exemplified in the above-mentioned nickel compounds.

Among the transition metal compounds, specific examples of a compound in which a transition metal atom is an iron atom include 2,6-bis-[1-(2,6-dimethylphenylimino)ethyl]pyridineiron dichloride, 2,6-bis-[1-(2,6-diisopropylphenylimino)ethyl]pyridineiron dichloride, 2,6-bis-[1-(2-tert-butylphenylimino)ethyl]pyridineiron dichloride, [hydrotris(3,5-dimethylpyrazolyl)borate]iron chloride, [hydrotris(3,5-dimethylpyrazolyl)borate]iron bromide, [hydrotris(3,5-dimethylpyrazolyl)borate]iron iodide, [hydrotris(3,5-dimethylpyrazolyl)borate]iron methyl, [hydrotris(3,5-dimethylpyrazolyl)borate]iron ethyl, [hydrotris(3,5-dimethylpyrazolyl)borate]iron allyl, [hydrotris(3,5-dimethylpyrazolyl)borate]iron methallyl, [hydrotris (3,5-diethylpyrazolyl)borate]iron chloride, [hydrotris(3,5-diethylpyrazolyl)borate]iron bromide, [hydrotris(3,5-diethylpyrazolyl)borate]iron iodide, [hydrotris(3,5-diethylpyrazolyl)borate]iron methyl, [hydrotris(3,5-diethylpyrazolyl)borate]iron ethyl, [hydrotris (3,5-diethylpyrazolyl)borate]iron allyl, [hydrotris(3,5-diethylpyrazolyl)borate]iron methallyl, [hydrotris(3,5-di-tert-butylpyrazolyl)borate]iron chloride, [hydrotris(3,5-di-tert-butylpyrazolyl)borate]iron bromide, [hydrotris(3,5-di-tert-butylpyrazolyl)borate]iron iodide, [hydrotris(3,5-di-tert-butylpyrazolyl)borate]iron methyl, [hydrotris(3,5-di-tert-butylpyrazolyl)borate]iron ethyl, [hydrotris(3,5-di-tert-butylpyrazolyl)borate]iron allyl, [hydrotris(3,5-di-tert-butylpyrazolyl)borate]iron methallyl, and the like.

Further, compounds wherein an iron atom is replaced with a cobalt atom or a nickel atom can be similarly exemplified in the above-mentioned iron compounds.

These transition metal compounds may be used alone, or in combination of 2 or more kinds of the compounds.

Moreover, the catalyst for α-olefin polymerization obtained by contacting the above-mentioned modified aluminum oxy compound with a transition metal compound having a capability of stereoregular polymerization of an α-olefin is illustrated.

The transition metal compound used for the catalyst for α-olefin polymerization is not specifically limited if it is a transition metal compound capable of producing a stereoregular α-olefin polymer such as an isotactic propylene polymer or a syndiotactic propylene polymer, and for example, can be appropriately selected from the forementioned transition metal compounds.

Among the transition metal compounds having a capability of stereoregular polymerization of an α-olefin, specific examples of a compound in which the transition metal atom is a titanium atom include ethylenebis(2-methylcyclopentadienyl)titanium dichloride, ethylenebis(2-n-butylcyclopentadienyl)titanium dichloride, ethylenebis(3-methylcyclopentadienyl)titanium dichloride, ethylenebis(3-n-butylcyclopentadienyl)titanium dichloride, ethylenebis(2,3-dimethylcyclopentadienyl)titanium dichloride, ethylenebis(2,4-dimethylcyclopentadienyl)titanium dichloride, ethylenebis(2-ethyl-3-methylcyclopentadienyl)titanium dichloride, ethylenebis(2-ethyl-4-methylcyclopentadienyl)titanium dichloride, ethylenebis(2-methyl-3-ethylcyclopentadienyl)titanium dichloride, ethylenebis(2-methyl-4-ethylcyclopentadienyl)titanium dichloride, ethylenebis(2,3,4-trimethylcyclopentadienyl)titanium dichloride, ethylenebis(2,4,5-trimethylcyclopentadienyl)titanium dichloride, ethylenebis{2-(2-furyl)-3,5-dimethylcyclopentadienyl}titanium dichloride, ethylenebis(2-(2-furyl)-4,5-dimethylcyclopentadienyl}titanium dichloride, ethylenebis(indenyl)titanium dichloride, ethylenebis(4,5,6,7-tetrahydroindenyl)titanium dichloride, ethylenebis(2-phenylindenyl)titanium dichloride, ethylenebis(fluorenyl)titanium dichloride, ethylene(cyclopentadienyl)(fluorenyl)titanium dichloride, ethylene(methylcyclopentadienyl)(fluorenyl)titanium dichloride, ethylene(n-butylcyclopentadienyl)(fluorenyl)titanium dichloride, ethylene(tetramethylpentadienyl)(fluorenyl)titanium dichloride, isopropylidenebis(2-methylcyclopentadienyl)titanium dichloride, isopropylidenebis(2-n-butylcyclopentadienyl)titanium dichloride, isopropylidenebis(3-methylcyclopentadienyl)titanium dichloride, isopropylidenebis(3-n-butylcyclopentadienyl)titanium dichloride, isopropylidenebis(2,3-dimethylcyclopentadienyl)titanium dichloride, isopropylidenebis(2,4-dimethylcyclopentadienyl)titanium dichloride, isopropylidenebis(2-ethyl-3-methylcyclopentadienyl)titanium dichloride, isopropylidenebis(2-ethyl-4-methylcyclopentadienyl)titanium dichloride, isopropylidenebis(2-methyl-3-ethylcyclopentadienyl)titanium dichloride, isopropylidenebis(2-methyl-4-ethylcyclopentadienyl)titanium dichloride, isopropylidenebis(2,3,4-trimethylcyclopentadienyl)titanium dichloride, isopropylidenebis(2,4,5-trimethylcyclopentadienyl)titanium dichloride, isopropylidenebis{2-(2-furyl)-3,5-dimethylcyclopentadienyl}titanium dichloride, isopropylidenebis{2-(2-furyl)-4,5-dimethylcyclopentadienyl}titanium dichloride, isopropylidenebis(indenyl)titanium dichloride, isopropylidenebis(4,5,6,7-tetrahydroindenyl)titanium dichloride, isopropylidenebis(2-phenylindenyl)titanium dichloride, isopropylidene(cyclopentadienyl)(fluorenyl)titanium dichloride, isopropylidene(methylcyclopentadienyl)(fluorenyl)-titanium dichloride, isopropylidene(n-butylcyclopentadienyl)(fluorenyl)titanium dichloride, isopropylidene(tetramethylcyclopentadienyl)(fluorenyl)titanium dichloride, dimethylsilylenebis(2-methylcyclopentadienyl)titanium dichloride, dimethylsilylenebis(2-n-butylcyclopentadienyl)titanium dichloride, dimethylsilylenebis(3-methylcyclopentadienyl)titanium dichloride, dimethylsilylenebis(3-n-butylcyclopentadienyl)titanium dichloride, dimethylsilylenebis(2,3-dimethylcyclopentadienyl)titanium dichloride, dimethylsilylenebis(2,4- dimethylcyclopentadienyl)titanium dichloride, dimethylsilylenebis(2-ethyl-3-methylcyclopentadienyl) titanium dichloride, dimethylsilylenebis(2-ethyl-4-methylcyclopentadienyl)titanium dichloride, dimethylsilylenebis(2-methyl-3-ethylcyclopentadienyl) titanium dichloride, dimethylsilylenebis(2-methyl-4-ethylcyclopentadienyl)titanium dichloride, dimethylsilylenebis(2,3,4-trimethylcyclopentadienyl) titanium dichloride, dimethylsilylenebis(2,4,5-trimethylcyclopentadienyl)titanium dichloride, dimethylsilylenebis{2-(2-furyl)-3,5-dimethylcyclopentadienyl}titanium dichloride, dimethylsilylenebis{2-(2-furyl)-4,5-dimethylcyclopentadienyl}titanium dichloride, dimethylsilylenebis(indenyl)titanium dichloride, dimethylsilylenebis(2-methyl-indenyl)titanium dichloride, dimethylsilylenebis(2-methyl-4-phenyl-indenyl)titanium dichloride, dimethylsilylenebis(2-methyl-4,5-benzo-indenyl)titanium dichloride, dimethylsilylenebis(2-methyl-4-naphthylindenyl)titanium dichloride, dimethylsilylenebis (2-methyl-4-isopropyl-1-indenyl)titanium dichloride, dimethylsilylene(2-methyl-1-indenyl)(2-methyl-4-phenyl-1-indenyl)titanium dichloride, dimethylsilylene(2-methyl-1-indenyl)(2-methyl-4-naphthyl-1-indenyl)titanium dichloride, dimethylsilylene(2-methyl-1-indenyl)(2-methyl-4-isopropyl-1-indenyl)titanium dichloride, dimethylsilylene (2-methyl-4-phenyl-1-indenyl)(2-methyl-4-naphthyl-1-indenyl)titanium dichloride, dimethylsilylene(2-methyl-4-phenyl-1-indenyl)(2-methyl-4-isopropyl-1-indenyl)titanium dichloride, dimethylsilylene(2-methyl-4-naphthyl-1-indenyl)(2-methyl-4-isopropyl-1-indenyl)titanium dichloride, dimethylsilylenebis(2-ethyl-indenyl)titanium dichloride, dimethylsilylenebis(2-ethyl-4-phenyl-1-indenyl) titanium dichloride, dimethylsilylenebis(2-ethyl-4,5-benzo-indenyl)titanium dichloride, dimethylsilylenebis(2-ethyl-4-naphthyl-1-indenyl)titanium dichloride, dimethylsilylenebis (2-ethyl-4-isopropyl-1-indenyl)titanium dichloride, dimethylsilylene(2-ethyl-1-indenyl)(2-methyl-4-phenyl-1-indenyl)titanium dichloride, dimethylsilylene(2-ethyl-1-indenyl)(2-methyl-4naphthyl-1-indenyl)titanium dichloride, dimethylsilylene(2-ethyl-1-indenyl)(2-methyl-4-isopropyl-1-indenyl)titanium dichloride, dimethylsilylene(2-ethyl-4-phenyl-1-indenyl)(2-ethyl-4-naphthyl-1-indenyl)titanium dichloride, dimethylsilylene(2-ethyl-4-phenyl-1-indenyl)(2-ethyl-4-isopropyl-1-indenyl)titanium dichloride, dimethylsilylene(2-ethyl-4-naphthyl-1-indenyl)(2-ethyl-4-isopropyl-1-indenyl)titanium dichloride, dimethylsilylenebis(2,4,6-trimethyl-1-indenyl)titanium dichloride, dimethylsilylenebis(4,5,6,7-tetrahydroindenyl) titanium dichloride, dimethylsilylene(cyclopentadienyl) (fluorenyl)titanium dichloride, dimethylsilylene (methylcyclopentadienyl)(fluorenyl)-titanium dichloride, dimethylsilylene(n-butylcyclopentadienyl)(fluorenyl) titanium dichloride, dimethylsilylene (tetramethylcyclopentadienyl)(indenyl)titanium dichloride, (tert-butylamido)fluorenyl-1,2-ethanediyltitanium dichloride, (tert-butylamido)fluorenyl-1,2-ethanediyltitanium dimethyl, (tert-butylamido) fluorenyldimethylsilanetitanium dichloride, (tert-butylamido)fluorenyldimethylsilanetitanium dimethyl, and the like.

Further, in the above-mentioned titanium compound, a compound in which titanium is replaced with zirconium or hafnium can be similarly exemplified.

When a racemic modification and a meso modification exist in the above-mentioned transition metal compound, the racemic modification is preferable.

Among these transition metal compounds, the transition metal compound represented by the general formula (4) described below or the transition metal compound represented by the general formula (5) described below is preferable.

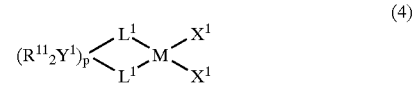

(4)

(wherein M is a transition metal atom of the Group IV of the Periodic Table, $L^1$ is an $\eta^5$-indenyl group or a substituted $\eta^5$-indenyl group, and two $L^1$'s may be mutually the same or different. $Y^1$ is a carbon atom, a silicon atom, a germanium atom or a tin atom, each of $R^{11}$ and $X^1$ is a hydrogen atom, a halogen atom, an alkyl group, an aralkyl group, an aryl group, a substituted silyl group, an alkoxy group, an aralkyloxy group, an aryloxy group or a heterocyclic group, and all of $R^{11}$ and $X^1$ may be the same or different mutually. p is 1 or 2.)

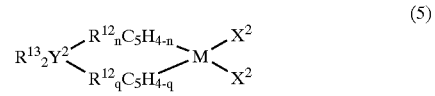

(5)

(wherein M is a transition metal atom of the Group IV of the Periodic Table, $Y^2$ is a silicon atom, a germanium atom or a tin atom, each of ($R^{12}_n$—$C_5H_{4-n}$) and ($R^{12}_q$—$C_5H_{4-q}$) is a substituted $\eta^5$-cyclopentadienyl group, and each of n and q is an integer of 1 to 3. The respective $R^{12}$ may be mutually the same or different, and indicate a halogen atom, an alkyl group, an aralkyl group, an aryl group, a substituted silyl group, an alkoxy group, an aralkyloxy group, an aryloxy group or a heterocyclic group. The position and/or kind of $R^{12}$ in the substituted $\eta^5$-cyclopentadienyl group is selected so that a symmetric plane including M does not exist. Each of $R^{13}$ and $X^2$ is a hydrogen atom, a halogen atom, an alkyl group, an aralkyl group, an aryl group, a substituted silyl group, an alkoxy group, an aralkyloxy group, an aryloxy group or a heterocyclic group, and all of $R^{13}$ and $X^2$ may be the same or different mutually.)

In the above-mentioned general formula (4) or (5), examples of the transition metal atom indicated by M include a titanium atom, a zirconium atom, a hafnium atom, and the like. A titanium atom or a zirconium atom is preferable.

In the above-mentioned general formula (4), $L^1$ is an $\eta^5$-indenyl group or a substituted $\eta^5$-indenyl group, and two $L^1$'s may be mutually the same or different. Specific examples of $L^1$ include an $\eta^5$-indenyl group, an $\eta^5$-methylindenyl group, an $\eta^5$-dimethylindenyl group, an $\eta^5$-n-propylindenyl group, an $\eta^5$-isopropylindenyl group, an $\eta^5$-n-butylindenyl group, an $\eta^5$-tert-butylindenyl group, an $\eta^5$-phenylindenyl group, an $\eta^5$-methylphenylindenyl group, an $\eta^5$-naphthylindenyl group, an $\eta^5$-trimethylsilylindenyl group, an $\eta^5$-tetrahydroindenyl group, and the like.

In the above-mentioned general formula (5), each of ($R^{12}_n$—$C_5H_{4-n}$) and ($R^{12}_q$—$C_5H_{4-q}$) is a substituted $\eta^5$-cyclopentadienyl group, and n and q are an integer of 1 to 3. The respective $R^{12}$ may be mutually the same or different, and indicate a halogen atom, an alkyl group, an aralkyl group, an aryl group, a substituted silyl group, an alkoxy group, an aralkyloxy group, an aryloxy group or a heterocyclic group. The position and/or kind of $R^{12}$ in the substituted $\eta^5$-cyclopentadienyl group is selected so that a symmetric plane including M does not exist.

As the halogen atom, a fluorine atom, a chlorine atom, a bromine atom and an iodine atom are exemplified, a chlorine atom or a bromine atom is preferable, and a chlorine atom is more preferable.

Further, the alkyl group is preferably an alkyl group having 1 to 20 carbon atoms, and examples the alkyl group include a methyl group, an ethyl group, a n-propyl group, an isopropyl group, a n-butyl group, a sec-butyl group, a tert-butyl group, an isobutyl group, a n-pentyl group, a neopentyl group, an isoamyl group, a n-hexyl group, a n-octyl group, a n-decyl group, a n-dodecyl group, a n-pentadecyl group, a n-eicosyl group and the like. A methyl group, an ethyl group, an isopropyl group, a tert-butyl group, an isobutyl group, or an amyl group is more preferable.

All of these alkyl groups may be substituted with a halogen atom such as a fluorine atom, a chlorine atom, a bromine atom or an iodine atom. Examples of the alkyl group having 1 to 10 carbon atoms which is substituted with a halogen atom include a fluoromethyl group, a trifluoromethyl group, a chloromethyl group, a trichloromethyl group, a fluoroethyl group, a pentafluoroethyl group, a perfluoropropyl group, a perfluorobutyl group, a perfluorohexyl group, a perfluorooctyl group, a perchloropropyl group, a perchlorobutyl group, a perbromopropyl group and the like.

Further, all of these alkyl groups may be partially substituted with an alkoxy group such as a methoxy group, an ethoxy group or the like, an aryloxy group such as a phenoxy group or the like or an aralkyloxy group such as a benzyloxy group or the like, etc.

As the aralkyl group, an aralkyl group having 7 to 20 carbon atoms is preferable. Examples include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-timethylphenyl)methyl group, a (2,3,5-timethylphenyl)methyl group, a (2,3,6-timethylphenyl)methyl group, a (3,4,5-timethylphenyl)methyl group, a (2,4,6-timethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-dodecylphenyl)methyl group, a naphthylmethyl group, an anthracenylmethyl group and the like, and a benzyl group is more preferable.

All of these aralkyl groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

As the aryl group, an aryl group having 6 to 20 carbon atoms is preferable. Examples include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, an anthracenyl group and the like, and a phenyl group is more preferable.

All of these aryl groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

The substituted silyl group is a silyl group substituted with a hydrocarbon group. Examples of the hydrocarbon group include alkyl groups having 1 to 10 carbon atoms such as a methyl group, an ethyl group, a n-propyl group, an isopropyl group, a n-butyl group, a sec-butyl group, a tert-butyl group, an isobutyl group, a n-pentyl group, a n-hexyl group, a cyclohexyl group and the like, aryl groups such as a phenyl group and the like, etc. Examples of the substituted silyl group having 1 to 20 carbon atoms include mono-substituted silyl groups having 1 to 20 carbon atoms such as a methylsilyl group, an ethylsilyl group, a phenylsilyl group and the like, di-substituted silyl groups having 2 to 20 carbon atoms such as a dimethylsilyl group, a diethylsilyl group, a diphenylsilyl group and the like, tri-substituted silyl groups having 3 to 20 carbon atoms such as a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a triisobutylsilyl group, a tert-butyldimethylsilyl group, a tri-n-pentylsilyl group, a tri-n-hexylsilyl group, a tricyclohexylsilyl group, a triphenylsilyl group and the like, etc. A trimethylsilyl group, a tert-butyldimethylsilyl group or a triphenylsilyl group is preferable.

All of these substituted silyl groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

An alkoxy group having 1 to 20 carbon atoms is preferable as the alkoxy group, and examples thereof include a methoxy group, an ethoxy group, a n-propoxy, an isopropoxy, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group, a n-eicosoxy group and the like. A methoxy group, an ethoxy group, an isopropoxy or a tert-butoxy group is more preferable.

All of these alkoxy groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

As the aralkyloxy group, an aralkyloxy group having 7 to 20 carbon atoms is preferable, and examples include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)

methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a naphthylmethoxy group, an anthracenylmethoxy group and the like, and a benzyloxy group is more preferable.

All of these aralkyloxy groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like or an aralkyloxy group such as a benzyloxy group or the like, etc.

As the aryloxy group, an aryloxy group having 6 to 20 carbon atoms is preferable, and examples include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2-tert-butyl-3-methylphenoxy group, a 2-tert-butyl-4-methylphenoxy group, a 2-tert-butyl-5-methylphenoxy group, a 2-tert-butyl-6-methylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 2-tert-butyl-3,4-dimethylphenoxy group, a 2-tert-butyl-3,5-dimethylphenoxy group, a 2-tert-butyl-3,6-dimethylphenoxy group, a 2,6-di-tert-butyl-3-methylphenoxy group, a 2-tert-butyl-4,5-dimethylphenoxy group, a 2,6-di-tert-butyl-4-methylphenoxy group, a 3,4,5-trimethylphenoxy group, a 2,3,4,5-tetramethylphenoxy group, a 2-tert-butyl-3,4,5-trimethylphenoxy group, a 2,3,4,6-tetramethylphenoxy group, a 2-tert-butyl-3,4,6-trimethylphenoxy group, a 2,6-di-tert-butyl-3,4-dimethylphenoxy group, a 2,3,5,6-tetramethylphenoxy group, a 2-tert-butyl-3,5,6-trimethylphenoxy group, a 2,6-di-tert-butyl-3,5-dimethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group, an anthracenoxy group and the like.

All of these aryloxy groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like or an aralkyloxy group such as a benzyloxy group or the like, etc.

The heterocyclic group is a group having a heterocyclic ring, a group having a 4 to 8-membered heterocyclic ring is preferable, and a group having a 4 to 8-membered aromatic heterocyclic ring is more preferable. A hetero atom contained in the heterocyclic ring is preferably a nitrogen atom, an oxygen atom or a sulfur atom. Specific examples of the heterocyclic group include, for example, an indolyl group, a furyl group, a thienyl group, a pyridyl group, a piperidyl group, a quinolyl group, an isoquinolyl group and the like. Specific examples of the heterocyclic group is more preferably a furyl group.

All of these heterocyclic groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

$R^{12}$ is preferably an alkyl group or a heterocyclic group. Each of n and q is an integer of 1 to 3.

As $(R^{12}_n$—$C_5H_{4-n})$ or $(R^{12}_q$—$C_5H_{4-q})$ having $R^{12}$, in which the position and/or kind of $R^{12}$ in the substituted $\eta^5$-cyclopentadienyl group is selected so that a symmetric plane including M does not exist, examples include a 2-methylcyclopentadienyl group, a 2-ethylcyclopentadienyl group, a 2-n-propylcyclopentadienyl group, a 2-isopropylcyclopentadienyl group, a 2-n-butylcyclopentadienyl group, a 2-isobutylcyclopentadienyl group, a 2-tert-butylcyclopentadienyl group, a 2-n-hexylcyclopentadienyl group, a 3-methylcyclopentadienyl group, a 3-ethylcyclopentadienyl group, a 3-n-propylcyclopentadienyl group, a 3-isopropylcyclopentadienyl group, a 3-n-butylcyclopentadienyl group, a 3-isobutylcyclopentadienyl group, a 3-tert-butylcyclopentadienyl group, a 3-n-hexylcyclopentadienyl group, a 2,3-dimethylcyclopentadienyl group, a 2,3-diethylcyclopentadienyl group, a 2,3-di-n-propylcyclopentadienyl group, a 2,3-diisopropylcyclopentadienyl group, a 2,3-di-n-butylcyclopentadienyl group, a 2,3-diisobutylcyclopentadienyl group, a 2,3-di-tert-butylcyclopentadienyl group, a 2,3-di-n-hexylcyclopentadienyl group, a 2,4-dimethylcyclopentadienyl group, a 2,4-diethylcyclopentadienyl group, a 2,4-di-n-propylcyclopentadienyl group, a 2,4-diisopropylcyclopentadienyl group, a 2,4-di-n-butylcyclopentadienyl group, a 2,4-diisobutylcyclopentadienyl group, a 2,4-di-tert-butylcyclopentadienyl group, a 2,4-di-n-hexylcyclopentadienyl group, a 3,5-dimethylcyclopentadienyl group, a 3,5-diethylcyclopentadienyl group, a 3,5-di-n-propylcyclopentadienyl group, a 3,5-diisopropylcyclopentadienyl group, a 3,5-di-n-butylcyclopentadienyl group, a 3,5-diisobutylcyclopentadienyl group, a 3,5-di-tert-butylcyclopentadienyl group, a 3,5-di-n-hexylcyclopentadienyl group, a 2-ethyl-3-methylcyclopentadienyl group, a 2-methyl-3-ethylcyclopentadienyl group, a 2-methyl-3-n-propylcyclopentadienyl group, 2-methyl-3-isopropylcyclopentadienyl group, a 2-ethyl-3isopropylcyclopentadienyl group, a 2-methyl-3-n-butylcyclopentadienyl group, a 2-methyl-3-isobutylcyclopentadienyl group, a 2-methyl-3-tert-butylcyclopentadienyl group, a 2-methyl-3-n-hexylcyclopentadienyl group, a 2-ethyl-4-methylcyclopentadienyl group, a 2-methyl-4-ethylcyclopentadienyl group, a 2-methyl-4-n-propylcyclopentadienyl group, a 2-methyl-4-isopropylcyclopentadienyl group, a 2-ethyl-4- isopropylcyclopentadienyl group, a 2-methyl-4-n-butylcyclopentadienyl group, a 2-methyl-4-isobutylcyclopentadienyl group, a 2-methyl-4-tert-butylcyclopentadienyl group, a 2-methyl-4-n-hexylcyclopentadienyl group, a 3-ethyl-5-methylcyclopentadienyl group, a 3-methyl-5-ethylcyclopentadienyl group, a 3-methyl-5-n-propylcyclopentadienyl group, a 3-methyl-5-isopropylcyclopentadienyl group, 3-ethyl-5-isopropylcyclopentadienyl group, a 3-methyl-5-n-butylcyclopentadienyl group, a 3-methyl-5-isobutylcyclopentadienyl group, a 3-methyl-5-tert-butylcyclopentadienyl group, a 3-methyl-5-n-hexylcyclopentadienyl group, a 2,3,5-trimethylcyclopentadienyl group, a 2,4,5-trimethylcyclopentadienyl group, a 2-(2-furyl)-3,5-dimethylcyclopentadienyl group, a 2-(2-furyl)-4,5-dimethylcyclopentadienyl group, and the like.

In the above-mentioned general formula (4) or (5), each of $Y^1$ and $Y^2$ is a carbon atom, a silicone atom, a germanium atom or a tin atom, and a carbon atom or a silicone atom is preferable, respectively. p in the above-mentioned general formula (4) is 1 or 2.

In the above-mentioned general formula (4) or (5), each of $R^{11}$, $R^{13}$ and X is a hydrogen atom, a halogen atom, an alkyl group, an aralkyl group, an aryl group, a substituted silyl group, an alkoxy group, an aralkyloxy group, an aryloxy group or a heterocyclic group, and two $R^{11}$'s, $R^{13}$'s, $X^1$'s and $X^2$'s may be respectively the same or different mutually. Wherein the halogen atom, the alkyl group, the aralkyl group, the aryl group, the substituted silyl group, the alkoxy group, the aralkyloxy group, the aryloxy group and the heterocyclic group are respectively the same as those already illustrated as $R^{12}$.

As $R^{11}$ or $R^{13}$, a hydrogen atom or an alkyl group is preferable, respectively.

As $X^1$ or $X^2$, a halogen atom, an alkyl group, an aralkyl group or an alkoxy group is preferable.

One of these transition metal compounds may be used alone, or two or more may be used in combination.

These specific examples can mention a transition metal compound satisfying the general formula (4) or (5) among the fore-mentioned specific examples.

(C) Organoaluminum Compound

As the organoaluminum compound of the component(C) used in the olefin polymerization catalyst of the present invention, well-known organoaluminum compounds can be used. An organoaluminum compound indicated by the general formula (6) is preferable.

$$R_cAlY_{3-c} \qquad (6)$$

(wherein R represents a hydrocarbon group having 1 to 8 carbon atoms, Y represents a hydrogen atom and/or a halogen atom, and c represents a number satisfying an equation of $0<c\leq3$.)

R in the general formula (6) representing the organoaluminum compound is preferably an alkyl, and specific examples include a methyl group, an ethyl group, a n-propyl group, a n-butyl group, an isobutyl group, a n-hexyl group, a 2-methylhexyl group, a n-octyl group and the like, and a methyl group, an ethyl group, a n-butyl group, an isobutyl group and a n-hexyl group are preferable. When Y is a halogen atom, specific examples include a fluorine atom, a chlorine atom, a bromine atom and an iodine atom, and a chlorine atom is preferable.

Specific examples of the organoaluminum compound represented by the above-mentioned general formula (6) include trialkylaluminums such as trimethylaluminum, triethylaluminum, tri-n-propylaluminum, tri-n-butylaluminum, triisobutylaluminum, tri-n-hexylaluminum, tri-n-octylaluminum and the like; dialkylaluminum chlorides such as dimethylaluminum chloride, di-n-butylaluminum chloride, diisobutylaluminum chloride, di-n-hexylaluminum chloride and the like; alkylaluminum dichlorides such as methylaluminum dichloride, ethylaluminum dichloride, n-propylaluminum dichloride, n-butylaluminum dichloride, isobutylaluminum dichloride, n-hexylaluminum dichloride and the like; and dialkylaluminum hydrides such as dimethylaluminum hydride, diethylaluminum hydride, di-n-propylaluminum hydride, di-n-butylaluminum hydride, diisobutylaluminum hydride, di-n-hexylaluminum hydride and the like, etc.

Among these, trialkylaluminums are preferable and trimethylaluminum, triethylaluminum, tri-n-butylaluminum, triisobutylaluminum or tri-n-hexylaluminum is more preferable.

These organoaluminum compounds may be used alone or in combination of 2 or more kinds.

(D) Boron Compound

As the boron compound (D) in the present invention, there can be used any one of (D1) a boron compound represented by the general formula $BQ^1Q^2Q^3$, (D2) a boron compound represented by the general formula $G^+(BQ^1Q^2Q^3Q^4)^-$ and (D3) a boron compound represented by the general formula $(L—H)^+(BQ^1Q^2Q^3Q^4)^-$.

In the boron compound (D1) represented by the general formula $BQ^1Q^2Q^3$, B represents a boron atom in the trivalent valence state; $Q^1$ to $Q^3$ may be the same or different and represent a halogen atom, a hydrocarbon group, a halogenated hydrocarbon group, a substituted silyl group, an alkoxy group or a di-substituted amino group. Each of $Q^1$ to $Q^3$ is preferably a halogen atom, a hydrocarbon group having 1 to 20 carbon atoms, a halogenated hydrocarbon group having 1 to 20 carbon atoms, a substituted silyl group having 1 to 20 carbon atoms, an alkoxy group having 1 to 20 carbon atoms or an amino group having 2 to 20 carbon atoms, more preferably a hydrocarbon group having 1 to 20 carbon atoms or a halogenated hydrocarbon group having 1 to 20 carbon atoms.

Specific examples of the compound (D1) include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, etc., most preferably tris(pentafluorophenyl)borane.

In the boron compound (D2) represented by the general formula $G^+(BQ^1Q^2Q^3Q^4)^-$, $G^+$ represents an inorganic or organic cation; B represents a boron atom in the trivalent valence state; and $Q^1$ to $Q^4$ are as defined in $Q^1$ to $Q^3$.

Specific examples of $G^+$ as an inorganic cation in the compound represented by the general formula $G^+(BQ^1Q^2Q^3Q^4)^-$ include ferrocenium cation, alkyl-substituted ferrocenium cation, silver cation, etc. Examples of the $G^+$ as an organic cation include triphenylmethyl cation. $G^+$ is preferably a carbenium cation, particularly a triphenylmethyl cation. Examples of $(BQ^1Q^2Q^3Q^4)^-$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluorophenyl)borate, tetrakis(3,5-bistrifluoromethylphenyl)borate, etc.

Specific combinations of them include ferroceniumtetrakis(pentafluorophenyl)borate, 1,1'-dimethylferroceniumtetrakis(pentafluorophenyl)borate, silvertetrakis(pentafluorophenyl)borate, triphenylmethyltetrakis(pentafluorophenyl)borate, triphenylmethyltetrakis(3,5-bistrifluoromethylphenyl) borate, etc., most preferably triphenylmethyltetrakis (pentafluorophenyl)borate.

In the boron compound (D3) represented by the formula $(L—H)^+(BQ^1Q^2Q^3Q^4)^-$, L represents a neutral Lewis base; $(L—H)^+$ represents a Brfnsted acid; B represents a boron atom in the trivalent valence state; and $Q^1$ to $Q^4$ are as defined in $Q^1$ to $Q^3$.

Specific examples of $(L—H)^+$ as a Brfnsted acid in the compound represented by the formula $(L—H)^+$ $(BQ^1Q^2Q^3Q^4)^-$ include trialkyl-substituted ammoniums, N,N-dialkylaniliniums, dialkylammoniums, triarylphosphoniums, etc., and examples of $(BQ^1Q^2Q^3Q^4)^-$ include those as defined above.

Specific combination of them include triethylammoniumtetrakis(pentafluorophenyl)borate, tripropylammoniumtetrakis(pentafluorophenyl)borate, tri(n-butyl)ammoniumtetrakis(pentafluorophenyl)borate, tri(n-butyl)ammoniumtetrakis(3,5-bistrifluoromethylphenyl) borate, N,N-dimethylaniliniumtetrakis(pentafluorophenyl) borate, N,N-diethylaniliniumtetrakis(pentafluorophenyl) borate, N,N-2,4,6-pentamethylaniliniumtetrakis (pentafluorophenyl)borate, N,N-dimethylaniliniumtetrakis (3,5-bistrifluoromethylphenyl)borate, diisopropylammoniumtetrakis(pentafluorophenyl)borate, dicyclohexylammoniumtetrakis(pentafluorophenyl)borate, triphenylphosphoniumtetrakis(pentafluorophenyl)borate, tri (methylphenyl)phosphoniumtetrakis(pentafluorophenyl) borate, tri(dimethylphenyl)phosphoniumtetrakis (pentafluorophenyl)borate, etc., most preferably tri(n-butyl) ammoniumtetrakis(pentafluorophenyl)borate or N,N-dimethylanilinumtetrakis(pentafluorophenyl)borate.

The amount ratio (molar ratio) of respective catalyst components used in the present invention is not specifically limited. The molar ratio of the modified aluminum oxy compound of component(A) to the transition metal compound of component (B) [(A)/(B)] is preferably in the range of 1/1 to 10000/1, and more preferably 1/1 to 5000/1.

When the organoaluminum compound of component (C) is used, the molar ratio of (B) to (C)[(B)/(C)] is preferably in the range of 1/0.1 to 1/10000, more preferably 1/1 to 1/5000 and most preferably 1/1 to 1/1000.

When the boron compound of component (D) is used, the molar ratio of (B) to (D)[(B)/(D)] is preferably in the range of 1/0.01 to 1/100, more preferably 1/0.5 to 1/10.

A method of supplying respective catalyst components into a polymerization reactor is not specifically limited. The modified aluminum oxy compound (A), the transition metal compound (B), if necessary, further, the organoaluminum compound (C), if necessary, moreover, the boron compound (D) may be charged after previously contacted, and may be separately charged in the reactor. After contact of arbitrary two components among these, the remaining component(s) may be contacted.

When the respective components are used in a solution, each of the concentrations of the modified aluminum oxy compound(A) and the organoaluminum compound (C) is usually 0.0001 to 100 mol/L in terms of Al atom, and preferably 0.01 to 10 mol/L, respectively. The concentration of the transition metal compound (B) is usually 0.0001 to 100 mmol/L in terms of the transition metal atom, and preferably 0.01 to 50 mmol/L. The concentration of the boron compound (D) is usually 0.001 to 500 mmol/L in terms of the boron atom, and preferably 0.01 to 250 mmol/L.

The method of supplying each of the catalyst components in a reactor is not specifically limited. There is illustrated a method of supplying each of the components in a solid condition, a method of charging each of the components as a solution in which it is dissolved in a hydrocarbon solvent or in a slurry state in which it is suspended, or the like.

The polymerization process is not specifically limited, and includes a solvent polymerization using an aliphatic hydrocarbon such as butane, pentane, hexane, heptane, octane or the like; an aromatic hydrocarbon such as toluene or the like; or a halogenated hydrocarbon such as methylene dichloride or the like, as a solvent, or a slurry polymerization, a bulk polymerization which is carried out in a liquid monomer, a gas phase polymerization in which polymerization is conducted in a gaseous monomer, a high-pressure process in which polymerization is conducted in a supercritical fluid condition of a monomer under high temperature and high pressure, or the like. As the polymerization process, both of a batch-wise polymerization and a continuous polymerization are possible.

The polymerization temperature is usually −50° C. to 300° C. and preferably −20° C. to 250° C. The polymerization pressure is usually 0.1 to 300 MPa, preferably 0.1 to 200 MPa, and more preferably 0.1 to 100 MPa. In general, the polymerization time is appropriately determined according to the kind of a desired polymer and a reaction apparatus, and 1 minute to 20 hours can be adopted.

The polymerization catalyst of the present invention can be applied to polymerization of olefins. As monomers which can be applied, olefins and diolefins having 2 to 20 carbon atoms and the like can be used, and ethylene and α-olefins having 3 to 20 carbon atoms are preferable. Two or more monomers can also be used, simultaneously. These specific examples include ethylene, α-olefins such as propylene, 1-butene, 1-pentene, 4-methyl-1-pentene, 5-methyl-1-hexene, 1-hexene, 1-heptene, 1-octene, 1-nonene, 1-decene and vinylcyclohexane, cyclic olefins such as norbornene, diolefins such as 1,3-butadiene, 1,4-heptadiene, 1,5-hexadiene, 1,7-octadiene and 5-ethylidene-2-norbornene, and the like. The present invention can be applied to the homopolymerization or copolymerization of these olefins. Specific examples of the monomers constituting a copolymer include ethylene-α-olefin having 3 to 20 carbon atoms such as ethylene-propylene, ethylene-1-butene, ethylene-1-hexene and the like, said α-olefins such as propylene-1-butene and the like, but the present invention should not be limited thereto.

Further, as the olefin copolymer applying the catalyst for polymerization of the present invention, a copolymer of ethylene with an α-olefin (so called LLDPE, namely a linear low density polyethylene) is suitable in particular. Further, as the olefin polymer applying the catalyst for polymerization of the present invention, a homopolymer of an α-olefin, particularly, a homopolymer of propylene or 1-butene is suitable. Particularly, when 1-butene is polymerized using the catalyst for polymerization of the present invention, a homopolymer of 1-butene of ultra high molecular weight can be obtained.

Moreover, the use of the catalyst for α-olefin polymerization capable of producing an α-olefin polymer excellent in stereoregularity is suitable as a process for producing an isotactic stereoregular α-olefin polymer and is particularly suitable as a process for producing an isotactic stereoregular propylene polymer.

Specific examples of the isotactic stereoregular propylene polymer include a homopolymer of propylene, a copolymer of propylene with a comonomer such as ethylene and/or an α-olefin having 4 to 12 carbon atoms or the like in an amount of degree not losing crystallinity, etc. The amount of degree not losing crystallinity differs depending on the kind of comonomer, and for example, the amount of the repeating unit derived from ethylene in a copolymer is usually 10% by weight or less in case of ethylene, and the amount of the repeating unit derived from an α-olefin in a copolymer is usually 30% by weight or less in case of the α-olefin other than propylene such as 1-butene or the like. For example, a random copolymer and a block copolymer are exemplified in case of the copolymer.

Furthermore, the polymerization catalyst of the present invention can be also applied to homopolymerization of an alkenyl aromatic hydrocarbon or to copolymerization of an alkenyl aromatic hydrocarbon and an olefin.

Alkenyl aromatic hydrocarbon polymers of high molecular weight are produced with a high activity by using the polymerization catalyst of the present invention.

Specific examples of the alkenyl aromatic hydrocarbon include alkyl styrenes such as p-methylstyrene, m-methylstyrene, o-methylstyrene, p-ethylstyrene, m-ethylstyrene, o-ethylstyrene, 2,4-dimethylstyrene, 2,5-dimethylstyrene, 3,4-dimethyl styrene, 3,5-dimethyl styrene, 3-methyl-5-ethylstyrene, p-tert-butylstyrene, p-sec-butylstyrene and the like, alkenyl benzenes such as styrene, 2-phenylpropylene, 2-phenylbutene and the like, bisalkenyl benzenes such as divinylbenzene and the like, vinylnaphthalenes such as 1-vinylnaphthalene and the like. And, styrene, p-methylstyrene, m-methylstyrene, o-methylstyrene, p-tert-butylstyrene, 2-phenylpropylene, divinylbenzene and 1-vinylnaphthalene are preferred, and, among these, styrene is particularly preferred. As olefins, the olefins as described above are used.

A chain transfer agent such as hydrogen or the like can also be added to adjust the molecular weight of the polymer.

The present invention is illustrated in detail according to Examples and Comparative Examples below, but not limited thereto.

Properties of the olefin polymers in Examples were measured according to methods described below.
(1) Intrinsic Viscosity [η]

It was measured in tetralin solution at 135° C. using an Ubbelohde viscometer.(Unit: dl/g)
(2) Molecular Weight Distribution (Mw/Mn)

It was measured under the conditions described below according to gel permeation chromatography (GPC). Molecular weight distribution was represented by a ratio of weight average molecular weight (Mw) to number average molecular weight(Mn)(Mw/Mn). Further, the calibration curve was made using a standard polystyrene.

MEASURING CONDITIONS OF EXAMPLES AND COMPARATIVE EXAMPLES AS FOLLOWS (2-1) (In Examples 1-22 and 25-29 and Comparative Examples 1-8, 11 and 12)
  Measurement machine: 150C type, manufactured by Milipore Waters Co.
  Column: TSK gel GMH6-HT
  Measurement temperature: 145° C.
  Solvent: ortho-dichlorobenzene
  Sample concentration: 10 mg/10 ml (when the molecular weight is particularly high, the measurement was carried out at a lowered concentration.)
(2-2) (In Examples 23-24 and Comparative Examples 9-10)
  Measurement machine: 800 Series, manufactured by JASCO Co.
  Column: Shodex A806M
  Measurement temperature: 45° C.
  Solvent: tetrahydrofuran
  Sample concentration: 0.5 mg/ml
(3) Melting Point of Polymer (In Examples 11-18 and 20-21 and Comparative Examples 5-8)

It was measured under the conditions below using a differential scanning calorimeter (DSC) (SSC-5000 series thermal analysis system manufactured by Seiko Instruments Inc.).
  Heating: 40° C. to 150° C. (10° C./minute), retention for 5 minutes
  Cooling: 150° C. to 10° C. (5° C./minute), retention for 10 minutes
  Measurement: 10° C. to 160° C. (heating at 5° C./minute)
(4) Glass Transition Temperature and Melting Point (In Examples 23-24 and Comparative Examples 9 and 10)

It was measured under the conditions below using a differential scanning calorimeter (DSC) (DSC-5200 manufactured by Seiko Instruments Inc.).
  Heating: 20° C. to 200° C. (20° C./minute), retention for 10 minutes
  Cooling: 200° C. to −50° C. (20° C./minute), retention for 10 minutes
  Measurement: −50° C. to 300° C. (heating at 20° C./minute)
(5) Melting Point of Polymer (In Examples 26-29 and Comparative Examples 11 and 12)

It was measured under the conditions below using a differential scanning calorimeter (DSC) (DSC-5200 manufactured by Seiko Instruments Inc.).
  Heating: −50° C. to 200° C. (20° C./minute), retention for 5 minutes
  Cooling: 200° C. to −50° C. (20° C./minute), retention for 5 minutes
  Measurement: −50° C. to 300° C. (heating at 20° C./minute)
(6) α-olefin Unit Content of Copolymer It was determined from the characteristic absorptions of ethylene and α-olefin and indicated in terms of the number of short branches per 1000 carbon atoms (SCB) in the copolymer.
(7) $^{13}$C-NMR Measurement(Isotactic Pentad Fraction (mmmm %))

It was carried out by measuring a solution of 200 mg of a sample dissolved in a mixed solvent of o-dichlorobenzene with deuterated benzene (volume ration of o-dichlorobenzene to deuterated benzene:3/1) using a NMR spectrometer (AC-250) manufactured by Bruker Ltd.).
(8) $^{27}$Al-solid NMR Spectrum NMR spectrometer having a super conductive magnet of 7.0 T ($^1$H observation frequency of 300 MHz)(ASX-300 (WB) manufactured by Bruker Ltd.) was used, and a measuring probe having a rotation cell diameter of 4 mm was used.

Nitrogen gas was used as a gas for rotating the cell, and the measurement was carried out after the inner atmosphere of a housing of the measuring probe was thoroughly replaced with nitrogen. Modified aluminum oxy compounds and aluminum oxy compounds samples were prepared by drying the solution thereof under reduced pressure to remove the solvent thereby to dry and solidify the solution. In a nitrogen box, the solid NMR measurement sample was packed in a rotation cell of a diameter of 4 mm for solid NMR measurement in a predetermined amount so that the cell could be stably rotated. The rotation speed of the cell was adjusted between 12 to 14 kHz, and the measurement was carried out in the room being adjusted at 20° C. (the measuring temperature was about 15 to about 20° C.). As a measurement pulse series, there was used a pulse series in which a de-coupler is off in the HPDEC method. The pulse width was set to $0.5\mu$ seconds which was narrower than 90° pulse width used in a solution $^{27}$Al-NMR spectrum. The pulse interval was set to 2 seconds. The width of the spectrum was set to 800 ppm as a width of the chemical shift of $^{27}$Al.

As the standard of the chemical shift, the peak appeared at higher magnetic field side was determined as 7 ppm using an active alumina of LC column packing. After completion of the measurement, the obtained data are subjected to Fourier transfer to obtain an $^{27}$Al-solid NMR spectrum. In the obtained $^{27}$Al-solid NMR spectrum, the phase and baseline correction thereof were compensated so that the heights of bases of the highest magnetic field peak group and the lowest magnetic field peak group among peak groups appeared from a vicinity of −150 ppm to a vicinity of 150 ppm, mutually became the same height, and the spectrum of a part in which no peak is observed in regions −150 ppm under and 150 ppm over, became parallel to the chemical shift axis (axis of abscissa) as far as possible. The baseline as a standard was drawn between bases of the highest magnetic field peak group and the lowest magnetic field peak group so that it became parallel to the chemical shift axis (axis of abscissa) as far as possible. A vertical line was drawn at 10 ppm to the chemical shift axis (axis of abscissa), and the distance(length) between the intersecting point of the vertical line with baseline and the intersecting point of the vertical line with the spectrum was measured. And, when a vertical was drawn at 30 ppm to the chemical shift axis(axis of abscissa), the distance between the intersecting point of the vertical line with the baseline and the intersecting point of the vertical line with the spectrum was measured.

Reference Example 1
[Synthesis Example of Dimethylsilylene (tetramethylcyclopentadienyl)(3-tert-butyl-5-methyl-2-phenoxy)titanium Dimethoxide <Compound 1>]

Methanol of 0.131 g(4.1 mmol) was dissolved with 10 ml of anhydrous diethylether in a Schlenk tube, and then a diethyl ether solution of methyl lithium (3.9 ml, 4.1 mmol) having a concentration of 1.05 mol/L was added thereto dropwise at −78° C. The resulting reaction solution was heated to 20° C., the formation of lithium methoxide was confirmed by the completion of a releasing of a gas, and then was cooled to −78° C. again. An anhydrous dimethyl ether suspension(20 ml) of 0.919 g(2.0 mmol) of dimethylsilylene (tetramethylcyclopentadienyl)(3-tert-butyl-5-methyl-2-phenoxy)titanium dichloride prepared previously in another Schlenk tube was transferred into the reaction solution above, thereafter the resulting reaction mixture was heated gradually to room temperature. After the thus obtained reaction solution was concentrated, 20 ml of toluene was added thereto, and then the insoluble matter was removed by filtration. The filtrate was concentrated to obtain dimethylsilylene(tetramethylcyclopentadienyl)(3-tert-butyl-5-methyl-2-phenoxy)titanium dimethoxide as a yellow crystal(yield 0.86 g, 95%). $^{1}$H-NMR(270 MHz, $C_6D_6$) δ7.26 (m, 2H), 4.13(s, 6H), 2.33(s, 3H), 1.97(s, 6H), 1.89(s, 6H), 1.59(s, 9H), 0.55(s, 6H)

Example 1

Figure 2:
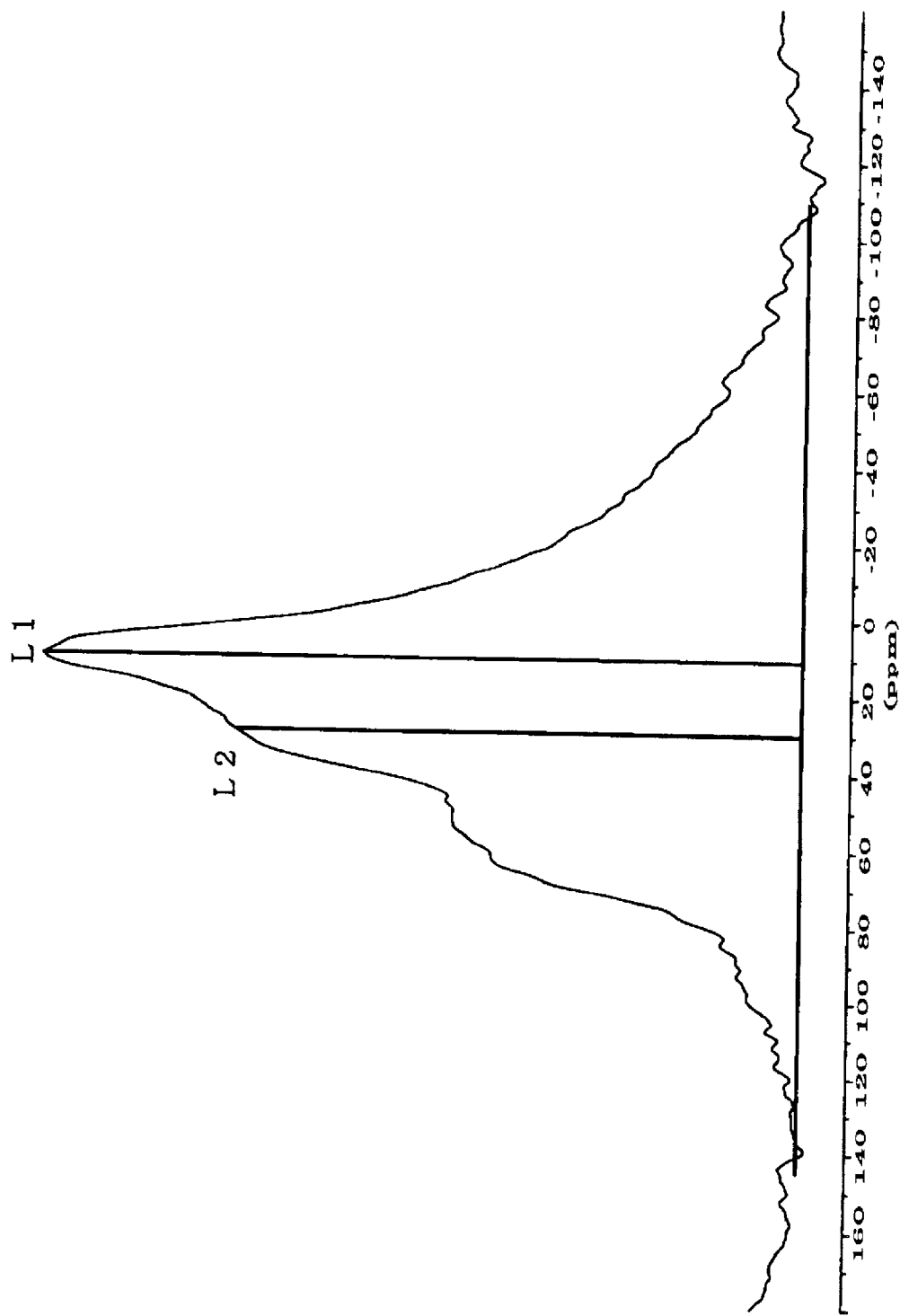
FIG. 2 shows an $^{27}$Al-solid NMR spectrum of a sample obtained by drying a reaction product obtained by mixing MMAO3A(toluene solution, manufactured by TOSOH-AKZO Co., Ltd.) and water with stirring as in Example 1, under reduced pressure. The ratio of L2 to L1 was 0.75 from this spectrum.
Figure 3:
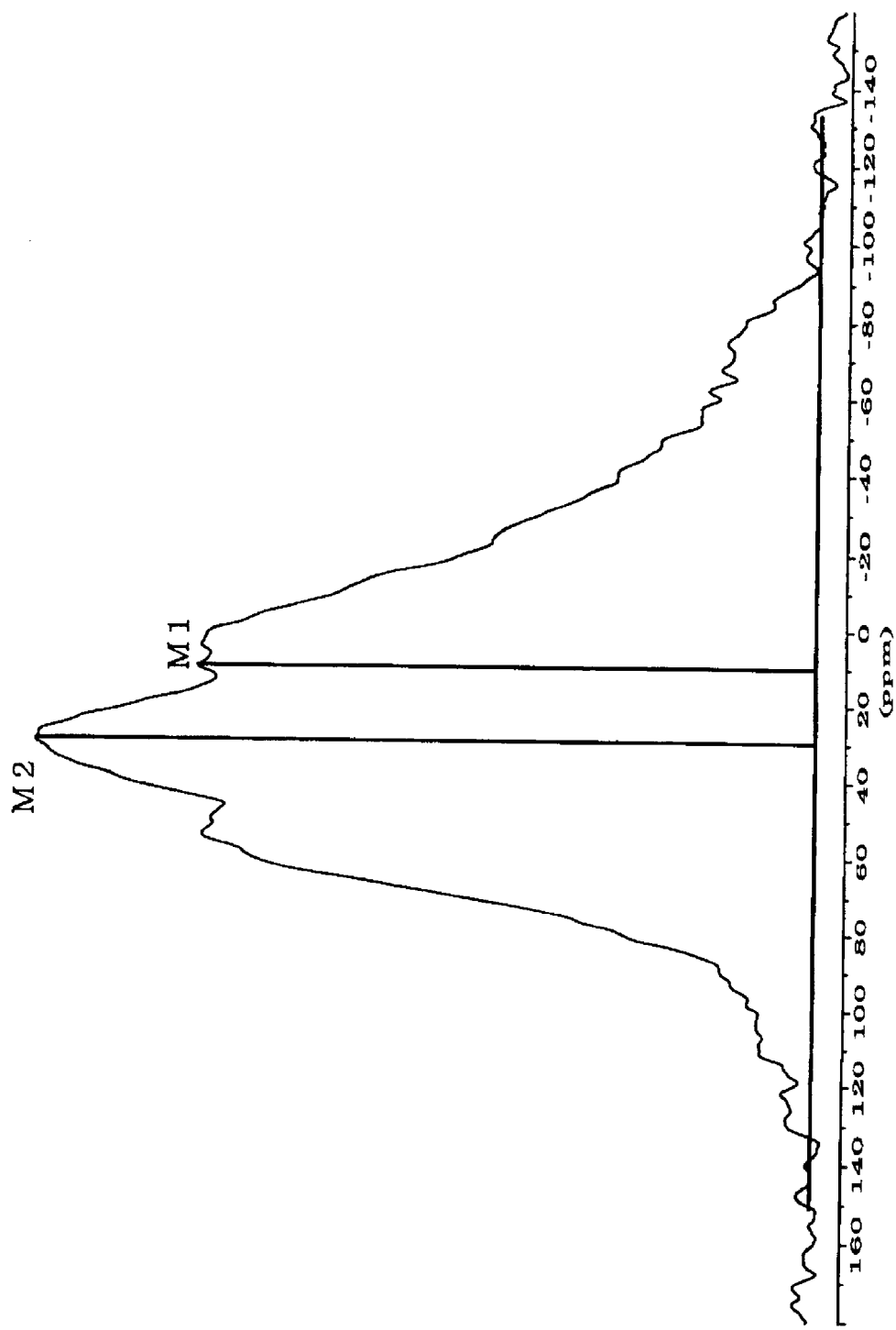
FIG. 3 shows an $^{27}$Al-solid NMR spectrum of a sample obtained by drying a reaction product obtained by mixing MMAO3A(toluene solution, manufactured by TOSOH-AKZO Co., Ltd.) and water with stirring and then adding pentafluorophenol thereto with stirring as in Example 1, under reduced pressure. The ratio of M2 to M1 was 1.26 from this spectrum.

A 100 ml stainless autoclave was replaced with argon, 2.5 mmol (in terms of Al atom) of MMAO3A (toluene solution having an Al concentration of 5.9% by weight, hereinafter, may be abbreviated as "MMAO") manufactured by TOSOH-AKZO Co., Ltd. of a toluene solution and 0.5 mmol of water were charged therein, and the mixture was stirred for 10 minutes. Further, 0.5 mmol of pentafluorophenol (toluene solution: 2 mol/l) was added, and the resultant was stirred for 10 minutes. In addition, the ratio H2/H1 of the MMAO3A was 0.27 as shown in FIG. 1, the ratio L2/L1 of the dried reaction product of the MMAO3A and water was 0.75 as shown in FIG. 2, and the ratio M2/M1 of the dried modified aluminum oxy compound was 1.26 as shown in FIG. 3.

On the other hand, in an egg-plant type flask of a volume of 25 ml in which the atmosphere was replaced with argon, 1 ml of purified toluene and 0.5 $\mu$mol of 2,2'-thiobis(4-methyl-6-tert-butylphenoxy)titanium dichloride were mixed with stirring, and then the solution was charged into the fore-mentioned autoclave using a syringe.

After the resulting catalyst solution was stirred at room temperature for 10 minutes, 30 g of 1-butene was charged and polymerization was carried out at 40° C. for 15 minutes. After completion of the reaction, the unreacted 1-butene was purged out, the contents of the autoclave were charged into about 10-fold acidic methanol, and the precipitated polymer was separated by filtration and then dried for about 2 hours at 80° C. As a result, 0.17 g of poly(1-butene) was obtained. Polymerization activity (gram of polymer per 1 mol of Ti per 1 hour) was $1.34 \times 10^6$ g/mol-Ti.hr. The [η] of the poly(1-butene) was 10.9 dl/g and Mw/Mn was 2.0.

Example 2

A 100 ml stainless autoclave was replaced with argon, 5 mmol of MMAO of a toluene solution and 1 mmol of pentafluorophenol(toluene solution: 2 mol/l) were added, and the mixture was stirred for 10 minutes. Further, 1 mmol of water was added, and the mixture was stirred for 10 minutes.

Figure 4:
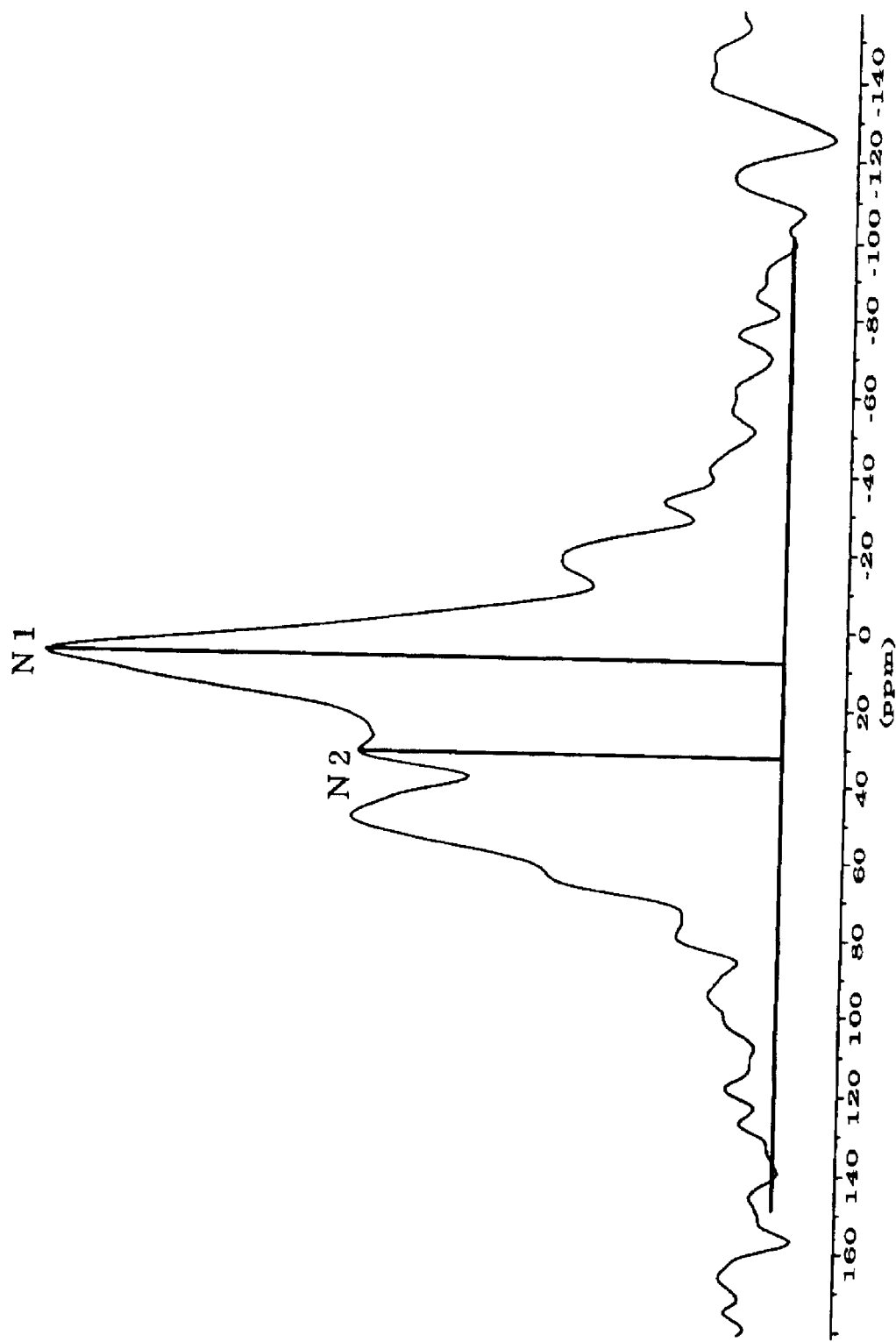
FIG. 4 shows an $^{27}$Al-solid NMR spectrum of a sample obtained by drying a reaction product obtained by mixing MMAO3A(toluene solution, manufactured by TOSOH-AKZO Co., Ltd.) and pentafluorophenol with stirring as in Example 1, under reduced pressure. The ratio of N2 to N1 was 0.57 from this spectrum.
Figure 5:
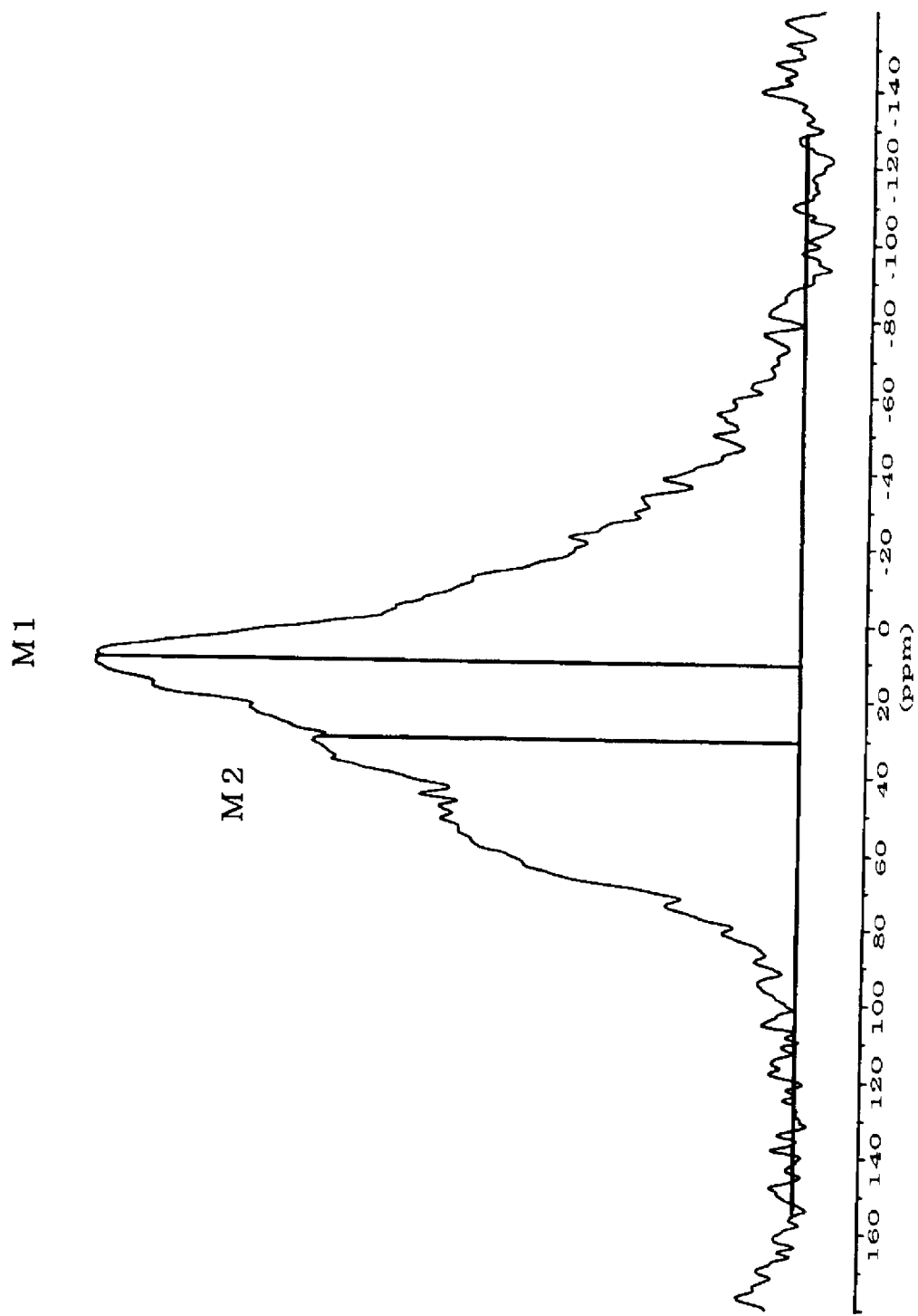
FIG. 5 shows an $^{27}$Al-solid NMR spectrum of a sample obtained by drying a reaction product obtained by mixing MMAO3A(toluene solution, manufactured by TOSOH-AKZO Co., Ltd.) and pentafluorophenol with stirring and then adding water with stirring as in Example 2, under reduced pressure. The ratio of M2 to M1 was 0.70 from this spectrum.

In addition, the ratio H2/H1 of the MMAO3A was 0.27 as shown in FIG. 1, the ratio N2/N1 of the dried reaction product of the MMAO3A and pentafluorophenol was 0.57 as shown in FIG. 4, and the ratio M2/M1 of the dried modified aluminum oxy compound was 0.70 as shown in FIG. 5.

On the other hand, in an egg-plant type flask of a volume of 25 ml in which the atmosphere was replaced with argon, 5 ml of purified toluene and 2.5 $\mu$mol of 2,2'-thiobis(4-methyl-6-tert-butylphenoxy)titanium dichloride were mixed with stirring, and then the solution was charged into the fore-mentioned autoclave using a syringe.

After the resulting catalyst solution was stirred at room temperature for 10 minutes, 30 g of 1-butene was charged and polymerization was carried out at 40° C. for 15 minutes. After completion of the reaction, the unreacted 1-butene was purged out, the content of the autoclave was charged into about 10-fold acidic methanol, and the precipitated polymer was separated by filtration and then dried at 80° C. for about 2 hours. As a result, 0.61 g of poly(1-butene) was obtained. Polymerization activity was $9.80 \times 10^5$ g/mol-Ti.hr. The [η] of the poly(1-butene) was 10.2 dl/g and Mw/Mn was 2.0.

Comparative Example 1

A 100 ml stainless autoclave was replaced with argon, 5 mmol of MMAO of a toluene solution was added thereto. On the other hand, in an egg-plant type flask of a volume of 25 ml in which the atmosphere was replaced with argon, 5 ml of purified toluene and 2.5 $\mu$mol of 2,2'-thiobis(4-methyl- 6-tert-butylphenoxy)titanium dichloride were mixed with stirring, and then the solution was charged into the fore-mentioned autoclave using a syringe. After the resulting catalyst solution was stirred at room temperature for 10 minutes, 30 g of 1-butene was charged and polymerization was carried out at 40° C. for 15 minutes. After completion of the reaction, the 1-butene that was unreacted was purged out, the content of the autoclave was charged into about 10-fold acidic methanol, and the precipitated polymer was separated by filtration and then dried at 80° C. for about 2 hours. As a result, 0.024 g of poly(1-butene) was obtained. Polymerization activity was $3.80 \times 10^4$ g/mol-Ti.hr. The [η] of the poly(1-butene) was 0.53 dl/g.

Comparative Example 2

A 100 ml stainless autoclave was replaced with argon, 2.5 mmol of MMAO of a toluene solution and 0.5 mmol of water were added thereto, and the mixture was stirred for 10 minutes.

On the other hand, in an egg-plant type flask of a volume of 25 ml in which the atmosphere was replaced with argon, 1 ml of purified toluene and 0.5 μmol of 2,2'-thiobis(4-methyl-6-tert-butylphenoxy)titanium dichloride were mixed with stirring, and then the solution was charged into the fore-mentioned autoclave using a syringe. After the resulting catalyst solution was stirred at room temperature for 10 minutes, 30 g of 1-butene was charged and polymerization was carried out at 40° C. for 15 minutes. After completion of the reaction, the unreacted 1-butene was purged out, the content of the autoclave was charged into about 10-fold acidic methanol, and the precipitated polymer was separated by filtration and dried at 80° C. for about 2 hours. As a result, 0.055 g of poly(1-butene) was obtained. Polymerization activity was $4.37 \times 10^5$ g/mol-Ti.hr. The [η] of the poly(1-butene) was 5.90 dl/g.

Comparative Example 3

A 100 ml stainless autoclave was replaced with argon, 5 mmol of MMAO of a toluene solution and 1 mmol of pentafluorophenol(toluene solution: 2 mol/l) were added thereto, and the mixture was stirred for 10 minutes.

On the other hand, in an egg-plant type flask of a volume of 25 ml in which the atmosphere was replaced with argon, 5 ml of purified toluene and 2.5 μmol of 2,2'-thiobis(4-methyl-6-tert-butylphenoxy)titanium dichloride were mixed with stirring, and then the solution was charged into the fore-mentioned autoclave using a syringe. After the resulting catalyst solution was stirred at room temperature for 10 minutes, 30 g of 1-butene was charged and polymerization was carried out at 40 for 15 minutes. After completion of the reaction, the unreacted 1-butene was purged out, the content of the autoclave was charged into about 10-fold acidic methanol, and the polymer precipitated was separated by filtration to be dried at 80° C. for about 2 hours. As a result, 0.23 g of poly(1-butene) was obtained. Polymerization activity was $3.65 \times 10^5$ g/mol-Ti.hr. The [η] of the poly(1-butene) was 5.16 dl/g.

Example 3

Example 1 was repeated except that 0.3 mmol of triphenyl methanol in place of pentafluorophenol was used. As a result, 0.14 g of poly(1-butene) was obtained. Polymerization activity was $1.11 \times 10^6$ g/mol-Ti.hr. The [η] of the poly(1-butene) was 6.0 dl/g, and Mw/Mn was 1.9.

Example 4

Example 1 was repeated except that 0.25 mmol of tricyclohexylmethanol in place of pentafluorophenol was used.

As a result, 0.16 g of poly(1-butene) was obtained. Polymerization activity was $1.23 \times 10^6$ g/mol-Ti.hr. The [η] of the poly(1-butene) was 7.7 dl/g.

Example 5

Example 1 was repeated except that 0.5 mmol of 1,1,1,3,3,3-hexafluoroisopropanol in place of pentafluorophenol was used. As a result, 0.13 g of poly(1-butene) was obtained. Polymerization activity was $1.00 \times 10^6$ g/mol-Ti.hr.

Example 6

A 100 ml stainless autoclave was replaced with argon, 5 mmol of MMAO of a toluene solution and 1 mmol of water were added, and the mixture was stirred for 10 minutes. Further, 1 mmol of pentafluorophenol(toluene solution: 2 mol/l) was added, and the mixture was stirred for 10 minutes.

On the other hand, in an egg-plant type flask of a volume of 25 ml in which the atmosphere was replaced with argon, 5 ml of purified toluene and 2.5 μmol of (tert-butylamido)(tetramethylcyclopentadienyldimethylsilane)titanium dichloride were mixed with stirring, and then the solution was charged into the fore-mentioned autoclave using a syringe. After the resulting catalyst solution was stirred at room temperature for 10 minutes, 30 g of 1-butene was charged and polymerization was carried out at 40° C. for 15 minutes. After completion of the reaction, the unreacted 1-butene was purged out, the content of the autoclave was charged into about 10-fold acidic methanol, and the precipitated polymer was separated by filtration and then dried at 80° C. for about 2 hours. As a result, 0.18 g of poly(1-butene) was obtained. Polymerization activity was $2.80 \times 10^5$ g/mol-Ti.hr. The [η] of the poly(1-butene) was 1.31 dl/g.

Comparative Example 4

A 100 ml stainless autoclave was replaced with argon, 10 mmol of MMAO of a toluene solution was added thereto.

On the other hand, in an egg-plant type flask of a volume of 25 ml in which the atmosphere was replaced with argon, 5 ml of purified toluene and 10 μmol of (tert-butylamido)(tetramethylcyclopentadienyldimethylsilane)titanium dichloride were mixed with stirring, and then the solution was charged into the fore-mentioned autoclave using a syringe. After the catalyst solution was mixed by stirring at room temperature for 10 minutes, 30 g of 1-butene was charged and polymerization was carried out at 40° C. for 60 minutes. After completion of the reaction, the unreacted 1-butene was purged out, the content of the autoclave was charged into about 10-fold acidic methanol, and the precipitated polymer was separated by filtration and then dried at 80° C. for about 2 hours. As a result, 0.02 g of poly(1-butene) was obtained. Polymerization activity was $2.04 \times 10^3$ g/mol-Ti.hr. The [η] of the poly(1-butene) was 0.50 dl/g.

Example 7

Example 6 was repeated except that isopropylidene(cyclopentadienyl)(3-tert-butyl-5-methyl-2-phenoxy) titanium dichloride in place of (tert-butylamido)(tetramethylcyclopentadienyldimethylsilane)titanium dichloride was used. As a result, 0.60 g of poly(1-butene) was obtained. Polymerization activity was $2.39 \times 10^5$ g/mol-Ti.hr.

Example 8

Example 6 was repeated except that pentamethylcyclopentadienyltitanium trichloride in place of (tert-butylamido)

(tetramethylcyclopentadienyldimethylsilane)titanium dichloride was used and polymerization time was 30 minutes. As a result, 1.07 g of poly(1-butene) and was obtained. Polymerization activity was $8.58 \times 10^5$ g/mol-Ti.hr.

Example 9

A 1 liter stainless autoclave was replaced with argon, and 200 g of 1-butene was charged, 5 mmol of MMAO of a toluene solution and 1 mmol of water were added, and the mixture was stirred for 10 minutes. Further, 1 mmol of pentafluorophenol(toluene solution: 2 mol/l) was added, and the mixture was stirred for 10 minutes.

On the other hand, in an egg-plant type flask of an inner volume of 25 ml in which the atmosphere was replaced with argon, 5 ml of purified toluene and 2.5 μmol of(pentamethylcyclopentadienyl)(2,6-diisopropylphenoxy)titanium dichloride were mixed with stirring, and then the solution was charged into the fore-mentioned autoclave using a syringe. Polymerization was carried out at 40° C. for 60 minutes. After completion of the reaction, the unreacted 1-butene was purged out, the content of the autoclave was charged into about 10-fold acidic methanol, and the precipitated polymer was separated by filtration and then dried at 80° C. for about 2 hours. As a result, 42.2 g of poly(1-butene) was obtained. Polymerization activity was $1.69 \times 10^7$ g/mol-Ti.hr. The [η] of the poly(1-butene) was 0.97 dl/g and Mw/Mn was 1.8.

Example 10

Example 9 was repeated except that the polymerization temperature was 5° C. As a result, 36.2 g of poly(1-butene) was obtained. Polymerization activity was $1.45 \times 10^7$ g/mol-Ti.hr. The [η] of the poly(1-butene) was 3.2 dl/g and Mw/Mn was 1.8.

Example 11

A 0.4 liter stainless autoclave was replaced with argon, 198 ml of toluene as a solvent and 2 ml of hexene-1 as an α-olefin were charged and the temperature of the autoclave was raised to 60° C. After raising the temperature, ethylene was fed while controlling the pressure at 0.6 MPa. After stabilization of the inside of system, 2 mmol of MMAO of a toluene solution and 0.4 mmol of water were added, and the mixture was mixed by stirring for 10 minutes. Further, 0.4 mmol of pentafluorophenol(toluene solution: 2 mol/l) was added, and the mixture was mixed by stirring for 10 minutes. On the other hand, 1 ml of 1 mmol/L toluene solution of dimethylsilylene(tetramethylcyclopentadienyl) (3-tert-butyl-5-methyl-2-phenoxy)titanium dichloride was charged into the fore-mentioned autoclave using a syringe, and polymerization was carried out for 60 minutes. The unreacted monomer was purged out, the content of the autoclave was charged into about 10-fold acidic methanol, and the precipitated polymer was separated by filtration and then dried at 80° C. for about 2 hours. As a result of the polymerization, 5.93 g of ethylene-hexene-1 copolymer having an [η] of 4.45 dl/g and a melting point of 68.4° C. was obtained. Polymerization activity was $5.93 \times 10^6$ g/mol-Ti.hr.

Comparative Example 5

A 0.4 liter stainless autoclave was replaced with argon, 198 ml of toluene as a solvent and 2 ml of 1-hexene as an α-olefin were charged and the temperature of the autoclave was heated to 60° C. After the heating, ethylene was fed while adjusting the pressure at 0.6 MPa. After the system was stabilized, 2 mmol of MMAO of a toluene solution and 1 ml of 1 mmol/L toluene solution of dimethylsilylene (tetramethylcyclopentadienyl)(3-tert-butyl-5-methyl-2-phenoxy)titanium dichloride were charged into the fore-mentioned autoclave using a syringe and polymerization was carried out for 60 minutes. The monomer unreacted was purged out, the content of the autoclave was charged into about 10-fold acidic methanol, and the precipitated polymer was separated by filtration and then dried at 80° C. for about 2 hours. As a result of the polymerization, 2.16 g of ethylene-1-hexene copolymer having an [η] of 1.21 dl/g and melting points of 75.6° C. and 89.5° C. was obtained. Polymerization activity was $2.16 \times 10^6$ g/mol-Ti.hr.

Comparative Example 6

A 0.4 liter stainless autoclave was replaced with argon, 198 ml of toluene as a solvent and 2 ml of 1-hexene as an α-olefin were charged and the temperature of the autoclave was heated to 60° C. After the heating, ethylene was fed while adjusting the pressure at 0.6 MPa. After the system was stabilized, 2 mmol of MMAO of a toluene solution and 0.4 mmol of water were added, and the mixture was stirred for 10 minutes.

On the other hand, 1 ml of 1 mmol/L toluene solution of dimethylsilylene(tetramethylcyclopentadienyl)(3-tert-butyl-5-methyl-2-phenoxy)titanium dichloride was charged into the fore-mentioned autoclave using a syringe and polymerization was carried out for 60 minutes. The unreacted monomer was purged out, the content of the autoclave was charged into about 10-fold acidic methanol, and the precipitated polymer was separated by filtration and then dried at 80 for about 2 hours. As a result of the polymerization, 0.84 g of ethylene-1-hexene copolymer having an [η] of 1.54 dl/g and a melting point of 91.5° C. was obtained. Polymerization activity was $8.40 \times 10^5$ g/mol-Ti.hr.

Example 12

Example 11 was repeated except that 2 μmol of biscyclopentadienyltitanium dichloride in place of dimethylsilylene(tetramethylcyclopentadienyl)(3-tert-butyl-5-methyl-2-phenoxy)titanium dichloride was used. As a result of the polymerization, 9.62 g of ethylene-1-hexene copolymer having an [η] of 2.00 dl/g and a melting point of 119° C. was obtained. Polymerization activity was $4.81 \times 10^6$ g/mol-Ti.hr.

Example 13

Example 11 was repeated except that 2 μmol of (pentamethylcyclopentadienyl)(2,6-diisopropylphenoxy) titanium dichloride in place of dimethylsilylene (tetramethylcyclopentadienyl)(3-tert-butyl-5-methyl-2-phenoxy)titanium dichloride was used. As a result of the polymerization, 12.17 g of ethylene-1-hexene copolymer having an [η] of 2.78 dl/g and melting points of 51° C. and 113.8° C. was obtained. Polymerization activity was $6.09 \times 10^6$ g/mol-Ti.hr.

Example 14

Example 11 was repeated except that 2 μmol of dimethylsilylenebisindenylhafnium dichloride in place of dimethylsilylene(tetramethylcyclopentadienyl)(3-tert-butyl-5-methyl-2-phenoxy)titanium dichloride was used. As a result of the polymerization, 11.61 g of ethylene-1-hexene copolymer having an [η] of 2.25 dl/g and melting points of 71° C. and 112° C. was obtained. Polymerization activity was 5.81×10⁶ g/mol-Hf.hr.

Example 15

Example 11 was repeated except that 5 μmol of hydrotris (3,5-dimethylpyrazolylborate)titanium trichloride in place of dimethylsilylene(tetramethylcyclopentadienyl)(3-tert-butyl-5-methyl-2-phenoxy)titanium dichloride, 10 mmol of MMAO, 2 mmol of water and 2 mmol of pentafluorophenol (toluene solution: 2 mol/l) were used and polymerization temperature was 80° C. As a result of the polymerization, 2.61 g of ethylene-1-hexene copolymer having an [η] of 1.42 dl/g and a melting point of 110.7° C. was obtained. Polymerization activity was 5.22×10⁵ g/mol-Ti.hr.

Example 16

Example 15 was repeated except that hydrotris(3,5-dimethylpyrazolylborate)zirconium trichloride in place of hydrotris(3,5-dimethylpyrazolylborate)titanium trichloride was used. As a result of the polymerization, 9.62 g of ethylene-1-hexene copolymer having an [η] of 1.51 dl/g and a melting point of 123.5° C. and 112° C. was obtained. Polymerization activity was 1.92×10⁶ g/mol-Zr.hr.

Example 17

A dropping funnel was set on a 100 ml four-necked flask, the flask was replaced with nitrogen and then, a thermometer was set. 10 ml of heptane as a solvent, and 20 mmol of MMAO3A (manufactured by TOSOH-AKZO Co., Ltd.; heptane solution having an Al concentration of 7.0% by weight) were charged in the flask and the mixture was stirred. To the dropping funnel, 144 μl (8 mmol) of water deaerated with nitrogen and 10 ml of toluene were charged and slowly added dropwise into the flask. After completion of the dropwise addition, the dropping funnel was rinsed with 5 ml of toluene and the mixture was stirred at 25 to 30° C. for 30 minutes. Then, 4 ml (toluene solution: 2 mol/l) of pentafluorophenol and 10 ml of toluene were charged to the dropping funnel, and slowly added dropwise into the flask. After completion of the dropwise addition, the dropping funnel was rinsed with 5 ml of toluene and the mixture was stirred at 25 to 30° C. for 1 hour. The reaction solution was concentrated under vacuum to remove the solvent and obtain a white solid (compound A).

A 0.4 liter autoclave reactor equipped with a stirrer was replaced with argon, then 185 ml of cyclohexane as a solvent and 15 ml of 1-hexene as an α-olefin were charged, and the reactor was heated to 180° C. After the heating, ethylene was fed while adjusting the pressure at 2.5 MPa. After the system was stabilized, 50.6 mg (equivalent to 0.41 mmol in terms of Al atom) of the above-mentioned compound A and 0.5 ml (namely, 0.5 μmol of dimethylsilylene (tetramethylcyclopentadienyl)(3-tert-butyl-5-methyl-2-phenoxy)titanium dimethoxide (compound 1) and 25 μmol of triisobutylaluminum) of a heptane solution (the concentration of compound 1 is 1 μmol/ml and the concentration of triisobutylaluminum is 50 μmol/ml, and a molar ratio of Al atom to Ti atom was adjusted at 50) in which the compound 1 and triisobutylaluminum are mixed, were charged thereto. Polymerization was carried out for 2 minutes. As a result of the polymerization, 1.38 g of ethylene-1-hexene copolymer having an [η] of 2.12 dl/g and melting points of 79.5° C. and 83.1° C. was obtained. Polymerization activity per 1 mol of Ti atom was 2.7×10⁶ g/mol-Ti per 2 minutes (8.1×10⁷ g/mol-Ti.hr).

Example 18

A dropping funnel was set on a 200 ml four-necked flask, the flask was replaced with nitrogen and then, a thermometer was set. 12 ml of heptane as a solvent and 20 mmol of MMAO3A (manufactured by TOSOH-AKZO Co., Ltd.; heptane solution having an Al concentration of 7.0% by weight) were charged to the flask and the mixture was stirred. To the dropping funnel, 72 μl (4 mmol) of water deaerated with nitrogen and 5 ml of toluene were charged and slowly added dropwise into the flask. After completion of the dropwise addition, the dropping funnel was washed with 5 ml of toluene and the mixture was stirred at 25 to 30° C. for 30 minutes. Then, 8 ml (toluene solution: 2 mol/l) of pentafluorophenol was charged to the dropping funnel and added dropwise thereto at 25 to 30° C., and the mixture was stirred at 25 to 30° C. for 1 hour. A white slurry was obtained. (Al concentration: 0.5 mol/L)(compound B)

A 0.4 liter autoclave reactor equipped with a stirrer was replaced with argon, then 185 ml of cyclohexane as a solvent and 15 ml of 1-hexene as an α-olefin were charged, and the reactor was heated to 180° C. After the heating, ethylene was fed while adjusting the pressure at 2.5 MPa. After the system was stabilized, 2 ml(equivalent to 1 mmol, in terms of Al atom) of the above-mentioned compound B and 0.5 ml (namely, 0.5 μmol of dimethylsilylene (tetramethylcyclopentadienyl)(3-tert-butyl-5-methyl-2-phenoxy)titanium dimethoxide (compound 1) and 25 μmol of triisobutylaluminum) of a heptane solution (the concentration of compound 1 is 1 μmol/ml and the concentration of triisobutylaluminum is 50 μmol/ml, and a molar ratio of Al atom to Ti atom was adjusted at 50) in which the compound 1 and triisobutylaluminum were mixed, were charged thereto. Polymerization was carried out for 2 minutes. As a result of the polymerization, 3.65 g of ethylene-1-hexene copolymer having an [η] of 1.59 and melting points of 73.3° C. and 84.9° C. was obtained. Polymerization activity per 1 mol of Ti atom was 7.3×10⁶ g/mol-Ti per 2 minutes (2.19× 10⁸ g/mol-Ti.hr).

Example 19

A 1 liter stainless autoclave was replaced with argon, 200 ml of toluene was charged and the temperature of the autoclave was heated to 60° C. After the heating, ethylene was fed while adjusting the pressure at 0.6 MPa. After the system was stabilized, 5 mmol of MMAO of a toluene solution and 1 mmol of water were added, and the mixture was stirred for 10 minutes. Further, 1 mmol of pentafluorophenol(toluene solution: 2 mol/l) was added, and the mixture was stirred for 10 minutes.

On the other hand, 5 ml of 0.5 mmol/L toluene solution of 2,6-bis-[1-(2,6-diisopropylphenylimino)ethyl] pyridineiron dichloride was charged into the fore-mentioned autoclave using a syringe, and polymerization was carried out for 60 minutes. The monomer unreacted was purged out, the content of the autoclave was charged into about 10-fold acidic methanol, and the precipitated polymer was separated by filtration and then dried at 80° C. for about 2 hours. As a result of the polymerization, 2.40 g of polyethylene having an [η] of 1.57 dl/g was obtained. Polymerization activity 9.62×10⁵ g/mol-Fe.hr.

Example 20

A dropping funnel was set on a 200 ml four-necked flask, the flask was replaced with nitrogen and then, a thermometer was set. 10 ml of heptane as a solvent and 20 ml of MMAO3A (manufactured by TOSOH-AKZO Co., Ltd.; heptane solution having an Al concentration of 7.0% by weight) were charged to the flask and the mixture was stirred. To the dropping funnel, 144 μl (8 mmol) of water deaerated with nitrogen and 10 ml of toluene were charged and slowly added dropwise into the flask. After completion of the dropwise addition, the dropping funnel was washed with 5 ml of toluene and the mixture was stirred at 25 to 30° C. for 30 minutes. Then, 4 ml (toluene solution: 2 mol/l) of pentafluorophenol and 10 ml of toluene were charged to the dropping funnel and added dropwise to the flask at 25 to 30° C., After completion of the dropwise addition, the dropping funnel was washed with 5 ml of toluene and the mixture was stirred at 25 to 30° C. for 1 hour. The reaction solution was concentrated under reduced pressure to obtain a white solid(compound C).

A 0.4 liter autoclave reactor equipped with a stirrer was replaced with argon, then 185 ml of cyclohexane as a solvent and 15 ml of 1-hexene as an α-olefin were charged, and the reactor was heated to 180° C. After the heating, ethylene was fed while adjusting the pressure at 2.5 MPa. After the system was stabilized, 48.9 mg(equivalent to 0.40 mmol, in terms of Al atom) of the above-mentioned compound C, 0.5 ml of a mixed heptane solution of dimethylsilylene (tetramethylcyclopentadienyl)(3-tert-butyl-5-methyl-2-phenoxy)titanium dimethoxide (compound 1) and 25 μmol of triisobutylaluminum (the concentration of compound 1 is 1 μmol/ml, the concentration of triisobutylaluminum is 50 μmol/ml, and the molar ratio of Al atom to Ti atom was adjusted at 50)(namely, the compound 1 is 0.5 μmol, and triisobutylaluminum is 25 μmol), and 1.5 ml of a heptane slurry of N,N'-dimethylanilinium (tetrakispentafluorophenyl)borate(compound 2) (concentration; 1 μmol/ml) were charged thereto. Polymerization was carried out for 2 minutes. As a result of the polymerization, 6.5 g of ethylene-1-hexene copolymer having an [η] of 1.06 dl/g, SCB of 35.3, Mw of 63400, Mw/Mn of 3.4 and melting points of 75.2° C. and 83.4° C. was obtained. Polymerization activity per 1 mol of Ti atom was $1.3 \times 10^7$ g/mol-Ti per 2 minutes ($3.9 \times 10^8$ g/mol-Ti.hr).

Example 21

A 0.4 liter stainless autoclave was replaced with argon, 185 ml of cyclohexane as a solvent and 15 ml of 1-hexene as an α-olefin were charged and the reactor was heated to 180° C. After the heating, ethylene was fed while adjusting the pressure at 2.5 MPa. After the system was stabilized, 0.1 mmol of triisobutyl aluminum, 0.2 ml(0.1 mmol in terms of Al atom) of the slurry of compound B prepared in Example 18 and 0.5 ml of a heptane mixed solution of compound 1 and triisobutyl aluminum (concentration of compound 1; 1 μmol/ml, concentration of triisobutyl aluminum; 50 μmol/ml, molar ratio of Al atom to Ti atom (Al/Ti); 50)(namely 0.5 μmol of compound 1 and 25 μmol of triisobutyl aluminum), 1.5 ml of a heptane slurry of the compound 2 (concentration; 1 μmol/ml) were added into the autoclave. Polymerization was carried out for 2 minutes.

As a result of the polymerization, 3.07 g of ethylene-1-hexene copolymer having an [η] of 1.11 dl/g, SCBof 30.4, Mw of 52100, Mw/Mn of 2.4, and melting points of 80.8° C. and 92.7° C. was obtained. Polymerization activity per 1 mol of Ti atom was $6.1 \times 10^6$ g/mol-Ti per 2 minutes($1.83 \times 10^8$ g/mol-Ti.hour).

Example 22

A dropping funnel was set on a 100 ml four-necked flask, the flask was replaced with nitrogen and then, a thermometer was set. As a solvent, 8 ml of heptane as a solvent and 10 mmol of MMAO3A (manufactured by TOSO.AKZO Co., Ltd.; 2 mol/l) were charged in the flask and the mixture was stirred. To the dropping funnel, 72 μl (4 mmol) of water deaerated with nitrogen and 5 ml of toluene were charged and slowly added dropwise into the flask. After completion of the dropwise addition, the dropping funnel was rinsed with 5 ml of toluene and the mixture was stirred at 25 to 30° C. for 30 minutes. Then, 2 ml (toluene solution: 2 mol/l) of pentafluorophenol and 10 ml of toluene were charged to the dropping funnel, and slowly added dropwise at 25 to 30° C. into the flask. After completion of the dropwise addition, the mixture was stirred at 25 to 30° C. for 2 hours. A white slurry (concentration:0.67 mol/l in terms of Al atom)(Compound D) was obtained.

A 0.4 liter autoclave reactor equipped with a stirrer was replaced with argon, then 140 ml of cyclohexane as a solvent and 60 ml of 1-hexene as an α-olefin were charged, and the reactor was heated to 180° C. After the heating, ethylene was fed while adjusting the pressure at 2.5 MPa. After the system was stabilized, 1.5 ml of slurry of the compound D (equivalent to 1 mmol in terms of Al atom), 1 ml of a toluene solution of bis(n-butyl cyclopentadienyl)zirconium dichloride (concentration; 1 μmol/ml) and 3 ml of a heptane slurry of the compound 2(concentration;1 μmol/ml) were added into the reactor. Polymerization was carried out for 2 minutes. As a result of polymerization, 5.7 g of an ethylene-1-hexene copolymer was obtained. Polymerization activity per 1 mol of Zr atom was $5.7 \times 10^6$ g/mol-Zr per 2 minutes($1.71 \times 10^8$ g/mol-Zr/hour).

Comparative Example 7

A 0.4 liter stainless autoclave was replaced with argon, 185 ml of cyclohexane as a solvent and 15 ml of 1-hexene as an α-olefin were charged and the autoclave was heated to 180° C. After the heating, ethylene was fed while adjusting the pressure at 2.5 MPa. After the system was stabilized, 0.2 mmol of triisobutylaluminum, 0.5 ml of a heptane mixed solution of the compound 1 and triisobutylaluminum (concentration of the compound 1; 1 μmol/ml, concentration of triisobutylaluminum; 50 μmol/ml) (namely, 0.5 μmol of compound 1 and 25 μmol of triisobutylaluminum) were added thereinto, and subsequently 1.5 ml of a heptane slurry of the compound 2 (slurry concentration of 1 μmol/ml) was added. Polymerization was carried out for 2 minutes. As a result of the polymerization, 2.33 g of ethylene-1-hexene copolymer having an [η] of 1.04 dl/g and SCB of 31.7, Mw of 56500, Mw/Mn of 1.9 and melting points of 78.3° C. and 89.9° C. was obtained. Polymerization activity per 1 mol of Ti atom was $4.7 \times 10^6$ g/mol-Ti per 2 minutes($1.41 \times 10^8$ g/mol-Ti.hour).

Comparative Example 8

A dropping funnel was set on a 200 ml four-necked flask, the flask was replaced with nitrogen and then, a thermometer was set. 10 ml of heptaneas a solvent and 20 mmol of MMAO3A (manufactured by TOSOH-AKZO Co., Ltd.; 2 mol/l) were charged in the flask and the mixture was stirred. To the dropping funnel, 360 μl (20 mmol) of water deaerated with nitrogen and 5 ml of toluene were charged and slowly added dropwise into the flask. After completion of the dropwise addition, the dropping funnel was rinsed with 5 ml of toluene and the mixture was stirred at 25 to 30° C. for 30 minutes. The reaction solution was concentrated under reduced pressure to remove the solvent and obtain a white solid (Compound E).

A 0.4 liter autoclave reactor equipped with a stirrer was replaced with argon, then 185 ml of cyclohexane as a solvent and 15 ml of 1-hexene as an α-olefin were charged, and the reactor was heated to 180° C. After the heating, ethylene was fed while adjusting the pressure at 2.5 MPa. After the system was stabilized, 27.6 mg of the compound E (equivalent to 0.43 mmol in terms of Al atom), 0.5 ml of a heptane mixed solution of the compound 1 and triisobutylaluminum (concentration of the compound; 1 $\mu$mol/ml, concentration of triisobutylaluminum; 50 $\mu$mol/ml, molar ratio of Al atom to Ti atom; 50) (namely, 0.5 $\mu$mol of compound 1 and 25 $\mu$mol of triisobutylaluminum) and 1.5 ml of a heptane slurry of the compound 2 (concentration; 1 $\mu$mol/ml) were added thereinto. Polymerization was carried out for 2 minutes. As a result of the polymerization, 2.45 g of ethylene-1-hexene copolymer having an [$\eta$] of 0.97 dl/g and SCB of 34.5 and melting points of 76.6° C. and 83.8° C. was obtained. Polymerization activity per 1 mol of Ti atom was $4.9 \times 10^6$ g/mol-Ti per 2 minutes($1.47 \times 10^8$ g/mol-Ti/hour).

Example 23

A 0.4 liter autoclave reactor equipped with a stirrer was replaced with argon, 27 ml of styrene and 83 ml of a purified toluene were charged, and then 0.8 MPa of ethylene was charged therein. Further, 4.4 ml of a toluene solution of MMAO3A and 14 $\mu$l of water were mixed in a 50 ml flask replaced with argon and then stirred for 10 minutes, thereafter, 0.8 ml of a toluene solution of pentafluorophenol (toluene solution: 2 mol/l) was added, and stirred for 10 minutes. The mixture was charged into fore-mentioned autoclave, subsequently 3.2 mg of isopropylidenebis (indenyl)zirconium dichloride dissolved in 6.4 ml of toluene, was charged into the fore-mentioned autoclave and polymerization was carried out at 60° C. for 1 hour.

Thereafter, thus obtained reaction solution was poured in a mixture of 5 ml of hydrochloric acid(12N) and 1000 ml of methanol and then the resulting precipitate was filtered to obtain a white solid. The solid was washed with methanol and then was dried under reduced pressure to obtain 25.24 g of a polymer. This polymer had a Mn of 65,000, Mw/Mn of 2.2, glass transition temperature of 21° C. and melting point of 95° C.

Comparative Example 9

Example 23 was repeated except that 4.4 ml of the toluene solution of MMAO was charged without mixing with water and pentafluorophenol, to obtain 25.13 g of a polymer. This polymer had a Mn of 58,000, Mw/Mn of 2.2, glass transition temperature of 20° C. and melting point of 98° C.

Example 24

Example 23 was repeated except that 14 $\mu$l of water was changed to 29 $\mu$l of water, 3.2 mg of isopropylidenebis (indenyl)zirconium dichloride dissolved in 6.4 ml of a purified toluene was changed to 2.9 mg of (tert-butylamide) (tetramethylcyclopentadienyldimethylsilane)titanium dichloride dissolved in 5.8 ml of toluene, to obtain 11.36 g of a polymer. This polymer had a Mn of 798,000, Mw/Mn of 2.0, glass transition temperature of –6° C. and melting point of 78° C. This polymer was shaped by pre-heating the polymer at 180° C. for 3 minutes, hot-pressing the pre-heated polymer at a temperature of 180° C. under a pressure of 30 to 50 kg/cm$^2$ for 3 minutes. A pressed sheet having a size of 50 mm×50 mm×0.3 mm had a excellent tensile strength.

Comparative Example 10

Example 24 was repeated except that 4.4 ml of the toluene solution of MMAO was charged without mixing with water and pentafluorophenol, to obtain 13.04 g of a polymer. This polymer had a Mn of 67,000, Mw/Mn of 2.2, glass transition temperature of –6° C. and melting point of 79° C.

Example 25

Figure 6:
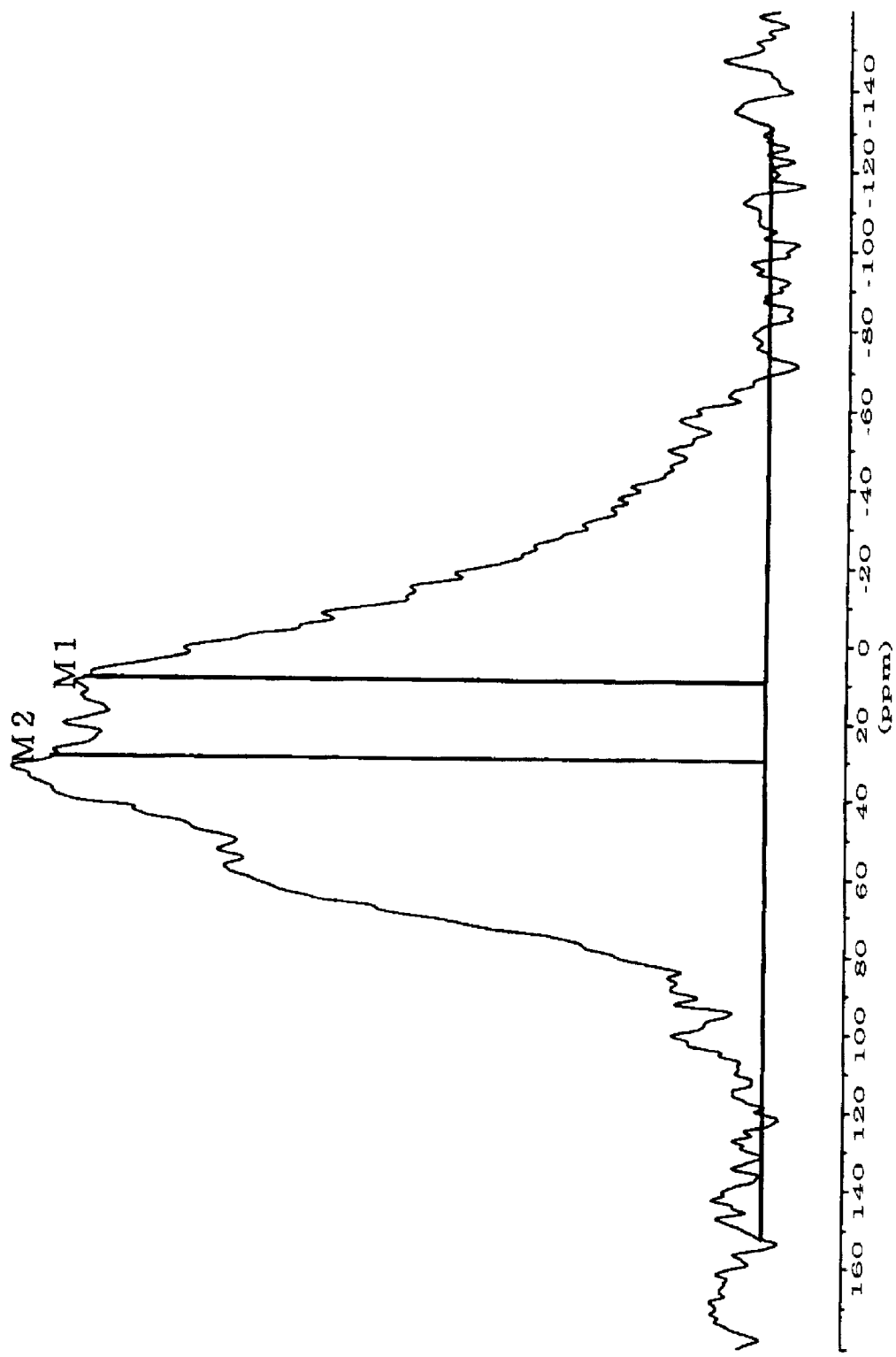
FIG. 6 shows an $^{27}$Al-solid NMR spectrum of a sample obtained by drying a reaction product obtained by simultaneously mixing MMAO3A(manufactured by TOSOH-AKZO Co., Ltd.), water and pentafluorophenol with stirring as in Example 25, under reduced pressure. The ratio of M2 to M1 was 1.04 from this spectrum. H1, H2, L1, L2, M1, M2, N1 and N2 are as defined below.

A 100 ml stainless autoclave was replaced with argon, 20 mmol (in terms of Al atom) MMAO3A of a toluene solution, 11 mmol of water and 4 mmol of pentafluorophenol(toluene solution: 2 mol/l) were simultaneously added and the resulting mixture was stirred for 10 minutes. In addition, the ratio H2/H1 of the MMAO3A was 0.27 as shown in FIG. 1, the ratio M2/M1 of the dried modified aluminum oxy compound was 1.04 as shown in FIG. 6.

On the other hand, in an egg-plant type flask of a volume of 25 ml in which the atmosphere was replaced with argon, 5 ml of purified toluene and 2.5 $\mu$mol of 2,2'-thiobis(4-methyl-6-tert-butylphenoxy)titanium dichloride were mixed with stirring, and then the resulting solution was charged into the autoclave using a syringe. After the resulting catalyst solution was stirred at room temperature for 10 minutes, 30 g of 1-butene was charged and polymerization was carried out at 40° C. for 15 minutes. After completion of the reaction, the unreacted 1-butene was purged out, the content of the autoclave was charged into about 10-fold acidic methanol, the resulting precipitated polymer was separated by filtration and then dried for at 80° C. for about 2 hours. As a result, 0.66 g of poly(1-butene) was obtained. Polymerization activity was $1.04 \times 10^6$ g/mol-Ti/hr. The [$\eta$]of poly(1-butene) was 9.21 dl/g.

Example 26

The atmosphere of a 1 liter stainless autoclave was replaced with argon, and 100 g of propylene was charged after charging 300 ml of toluene. Then, after raising a temperature to 40° C., 2.0 mmol (as a molar amount of Al atom) of MMAO3A of a toluene solution manufactured by TOSOH-AKZO Co., Ltd. (an Al concentration of 5.6% by weight; hereinafter, may be abbreviated as "MMAO1") and 0.2 mmol of water were charged therein by pressurization, and the mixture was mixed by stirring for 10 minutes. Further, 0.4 mmol of pentafluorophenol was charged therein by pressurization, and the mixture was stirred for 10 minutes.

On the other hand, in an egg-plant type flask of an inner volume of 25 ml in which the atmosphere was replaced with argon, 5 ml of purified toluene and 1 $\mu$mol of dimethylsilylenebis(2-methyl-1-indenyl)zirconium dichloride were mixed by stirring, and then the solution was charged into the fore-mentioned autoclave using a syringe. After carrying out the polymerization for 1 hour, the polymerization was stopped by charging 5 ml of methanol. After purging out the unreacted propylene, the contents of the autoclave were charged into about 1000 ml of acidic methanol, and the precipitated polymer was separated by filtration and then dried for about 2 hours at 80° C. As a result, 2.2 g of a polypropylene was obtained. The [$\eta$] of the polypropylene obtained was 2.9 dl/g, Mw/Mn was 2.0, mmmm % was 96.5% and melting point was 153.9° C. Further, in an $^{27}$Al-solid NMR spectrum of a sample obtained by drying MMAO1 under reduced pressure, the ratio of H2 to H1 was 0.27.

Example 27

Polymerization was similarly carried out except that the amount of pentafluorophenol was changed from 0.4 mmol to 0.6 mmol in Example 26. As a result, 3.2 g of a polypropylene was obtained. The [η] of the polypropylene obtained was 3.0 dl/g, Mw/Mn was 1.9, mmmm % was 96.3% and melting point was 153.8° C.

Example 28

Polymerization was similarly carried out except that the amount of water was changed from 0.2 mmol to 0.4 mmol and the amount of pentafluorophenol was changed from 0.4 mmol to 0.2 mmol in Example 26. As a result, 15.9 g of a polypropylene was obtained. The [η] of the polypropylene obtained was 2.8 dl/g, Mw/Mn was 2.0, mmmm % was 95.6% and melting point was 152.7° C.

Further, in an $^{27}$Al-solid NMR spectrum of a sample obtained by drying a reaction product obtained by mixing MMAO1 and water (molar ratio 5:1) with stirring, under reduced pressure, the ratio of L2 to L1 was 0.75.

Comparative Example 11

The atmosphere of a 1 liter stainless autoclave was replaced with argon, and 100 g of propylene was charged after charging 300 ml of toluene. Then, after raising a temperature to 40° C., 2.0 mmol of MMAO1 as a molar amount of Al atom was charged therein, and the mixture was mixed by stirring for 10 minutes.

On the other hand, in an egg-plant type flask of an inner volume of 25 ml in which the atmosphere was replaced with argon, 5 ml of purified toluene and 1 μmol of dimethylsilylenebis(2-methyl-1-indenyl)zirconium dichloride were mixed by stirring, and then the solution was charged into the fore-mentioned autoclave using a syringe. After carrying out the polymerization for 1 hour, the polymerization was stopped by charging 5 ml of methanol. After purging out the unreacted propylene, the contents of the autoclave were charged into about 1000 ml of acidic methanol, and the precipitated polymer was separated by filtration and then dried for about 2 hours at 80° C. As a result, 1.2 g of a polypropylene was obtained. The [η] of the polypropylene obtained was 2.5 dl/g, Mw/Mn was 2.0, mmmm % was 93.8% and melting point was 152.2° C.

Example 29

The atmosphere of a 1 liter stainless autoclave was replaced with argon, and propylene was introduced under a pressure of 0.3 MPa after charging 300 ml of toluene. Then, after raising a temperature to 40° C., 2.0 mmol of MMAO1 as a molar amount of Al atom and 0.2 mmol of water were charged therein under pressurization, and the mixture was mixed by stirring for 10 minutes. Further, 0.2 mmol of pentafluorophenol was charged therein by pressurization, and the mixture was stirred for 10 minutes.

On the other hand, in an egg-plant type flask of an inner volume of 25 ml in which the atmosphere was replaced with argon, 5 ml of purified toluene and 0.5 μmol of dimethylsilylenebis(2-methyl-4-naphthyl-1-indenyl)zirconium dichloride were mixed by stirring, and then the solution was charged into the fore-mentioned autoclave using a syringe. The polymerization was carried out for 1 hour. Propylene was continuously fed so that the pressure of propylene becomes always 0.3 MPa. Then, the polymerization was stopped by charging 5 ml of methanol. After purging out the unreacted propylene, the contents of the autoclave were charged into about 1000 ml of acidic methanol, and the precipitated polymer was separated by filtration and then dried for about 2 hours at 80° C. As a result, 2.0 g of a polypropylene was obtained. The Mw of the polypropylene obtained was $260 \times 10^4$, Mw/Mn was 2.0, mmmm % was 98.6% and melting point was 161.3° C.

Comparative Example 12

The atmosphere of a 1 liter stainless autoclave was replaced with argon, and propylene was introduced under a pressure of 0.3 MPa after charging 300 ml of toluene. Then, after raising a temperature to 40° C., 2.0 mmol of MMAO1 as a molar amount of Al atom was charged therein. On the other hand, in an egg-plant type flask of an inner volume of 25 ml in which the atmosphere was replaced with argon, 5 ml of purified toluene and 0.5 μmol of dimethylsilylenebis(2-methyl-4-naphthyl-1-indenyl)zirconium dichloride were mixed by stirring, and then the solution was charged into the fore-mentioned autoclave using a syringe. The polymerization was carried out for 1 hour. Propylene was continuously fed so that the pressure of propylene becomes always 0.3 MPa. Then, the polymerization was stopped by charging 5 ml of methanol. After purging out the unreacted propylene, the contents of the autoclave were charged into about 1000 ml of acidic methanol, and the precipitated polymer was separated by filtration and then dried for about 2 hours at 80° C. As a result, 1.1 g of a polypropylene was obtained. The Mw of the polypropylene obtained was $219 \times 10^4$, Mw/Mn was 2.5, mmmm % was 98.0% and melting point was 160.5° C.

According to the present invention, there is provided a modified aluminum oxy compound useful as a component of a polymerization catalyst capable of producing a high molecular weight olefin polymer with a high efficiency. Further, there are provided a polymerization catalyst obtained by using the modified aluminum oxy compound, and a process for producing an olefin polymer or an alkenyl aromatic hydrocarbon polymer with the polymerization catalyst, and a copolymer of an alkenyl aromatic hydrocarbon and an olefin.

What is claimed is:

1. A modified aluminum oxy compound, obtained by a process that comprises reacting:

an aluminum oxy compound(a) having a ratio of an intensity at 30 ppm(H2) to an intensity at 10 ppm(H1) [H2/H1] in an $^{27}$Al-solid NMR spectrum of less than 0.35, water(b), and a compound(c) having a hydroxy group selected from the group consisting of tertiary alcohols and alcohols substituted with a halogen atom, the alcohols substituted with a halogen being selected from the group consisting of alcohols indicated by the formula $CR^1R^2R^3$—OH (wherein each of $R^1$, $R^2$ and $R^3$ independently represents a hydrogen atom or hydrocarbon group having 1 to 20 carbon atoms, which is optionally substituted with a halogen atom, and they may be mutually the same or different), halogenated phenol compounds and silanol compounds;

wherein the modified aluminum oxy compound has a ratio of an intensity at 30 ppm(M2) to an intensity at 10 ppm(M1)[M2/M1] in an $^{27}$Al-solid NMR spectrum of 0.60 or more, the molar ratio[(a)/(b)] of the aluminum oxy compound(a) to water(b) is 1/3 to 1/0.01, and the molar ratio [(a)/(c)] of the aluminum oxy compound(a) to the compound(c) is 1/3 to 1/0.01.

2. The modified aluminum oxy compound according to claim 1, wherein said aluminum oxy compound (a) is an aluminum oxy compound that is soluble in an aromatic hydrocarbon or an aliphatic hydrocarbon represented by the general formula(1) or (2) below:

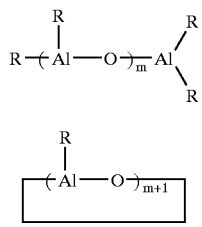

in which R indicates a hydrocarbon group having 1 to 20 carbon atoms, wherein the R groups may be the same or different; and m represents a number of 1 to 50.

3. The modified aluminum oxy compound according to claim 1, wherein the compound(c) is a member selected from the group consisting of halogenated phenol compounds, halogenated alcohol compounds and silanol compounds.

4. The modified aluminum oxy compound according to claim 3, wherein the compound(c) is a member selected from the group consisting of halogenated phenol compounds and silanol compounds.

5. A modified aluminum oxy compound, obtained by a process that comprises reacting:

an aluminum oxy compound(a') having a ratio of an intensity at 30 ppm(L2) to an intensity at 10 ppm(L1) [L2/L1] in an $^{27}$Al-solid NMR spectrum of not less than 0.35, which is obtained by reacting an aluminum oxy compound(a) having a ratio of an intensity at 30 ppm(H2) to an intensity at 10 ppm(H1)[H2/H1] in an $^{27}$Al-solid NMR spectrum of less than 0.35 and water (b); and a compound(c) having a hydroxy group selected from the group consisting of tertiary alcohols and alcohols substituted with a halogen atom, the alcohols substiuted with a halogen being selected from alcohols indicated by the formula $CR^1R^2R^3$—OH (wherein each of $R^1$, $R^2$ and $R^3$ independently represents a hydrogen atom or hydrocarbon group having 1 to 20 carbon atoms, which is optionally substituted with a halogen atom, and they may be mutually the same or different), halogenated phenol compounds and silanol compounds, wherein the modified aluminum oxy compound has a ratio of an intensity at 30 ppm(M2) to an intensity at 10 ppm(ml) [M2/M1] in an $^{27}$Al-solid NMR spectrum of 0.60 or more, the molar ratio[(a)/(b)] of the aluminum oxy copound(a) to water(b) is 1/3 to 1/0.01, and the molar ratio[(a)/(c)]]of the aluminum oxy compound(a) to the compound(c) is 1/3 to 1/0.01.

6. The modified aluminum oxy compound according to claim 5, wherein the ratio L2/L1 is not less than 0.35 and less than 0.90.

7. The modified aluminum oxy compound according to claim 5, wherein said aluminum oxy compound (a) is an aluminum oxy compound that is soluble in an aromatic hydrocarbon or an aliphatic hydrocarbon represented by the general formula (1) or (2) below:

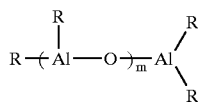

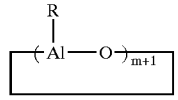

in which R indicates a hydrocarbon group having 1 to 20 carbon atoms, wherein the R groups may be the same or different; and m represents a number of 1 to 50.

8. The modified aluminum oxy compound according to claim 5, wherein the compound(c) is a member selected from the group consisting of halogenated phenol compounds, halogenated alcohol compounds and silanol compounds.

9. The modified aluminum oxy compound according to claim 8, wherein the compound(c) is a member selected from the group consisting of halogenated phenol compounds and silanol compounds.

10. A modified aluminum oxy compound, obtained by a process that comprises reacting:

an aluminum oxy compound(a") having a ratio of an intensity at 30 ppm(N2) to an intensity at 10 ppm(N1) [N2/N1] in an $^{27}$Al-solid NMR spectrum of not less than 0.35 obtained by reacting an aluminum oxy compound(a) having a ratio of an intensity at 30 ppm(H2) to an intensity at 10 ppm H1[H2/H1] in its $^{27}$Al-solid NMR spectrum of less than 0.35 and a compound(c) having a hydroxy group selected from the group consisting of tertiary alcohols and alcohols substituted with a halogen atom, the alcohol being selected from alcohols indicated by the formula $CR^1R^2R^3$—OH (wherein each of $R^1$, $R^2$ and $R^3$ independently represents a hydrogen atom or hydrocarbon group having 1 to 20 carbon atoms, which is optionally substituted with a halogen atom, and they may be mutually the same or different), halogenated phenol compounds and silanol compounds, with water(b), wherein the modified aluminum oxy compound has a ratio of an intensity at 30 ppm(M2) to an intensity at 10 ppm(M1)[M2/M1] in an $^{27}$Al-solid NMR spectrum of 0.60 or more, the molar ratio[(a)/(b)] of the aluminum oxy compound(a) to water(b) is 1/3 to 1/0.01, and the molar ratio[(a)/(c)]] of the aluminum oxy compound(a) to the compound(c) is 1/3 to 1/0.01.

11. The modified aluminum oxy compound according to claim 10, wherein the ratio N2/N1 is not less than 0.35 and less than 0.60.

12. The modified aluminum oxy compound according to claim 10, wherein said aluminum oxy compound (a) is an aluminum oxy compound that is soluble in an aromatic hydrocarbon or an aliphatic hydrocarbon represented by the general formula (1) or (2) below:

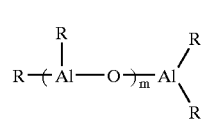

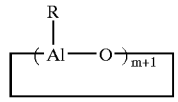

in which R indicates a hydrocarbon group having 1 to 20 carbon atoms, wherein the R groups may be the same or different; and m represents a number of 1 to 50.

13. The modified aluminum oxy compound according to claim 10, wherein the compound(c) is a member selected from the group consisting of halogenated phenol compounds, halogenated alcohol compounds and silanol compounds.

14. The modified aluminum oxy compound according to claim 13, wherein the compound(c) is a member selected from the group consisting of halogenated phenol compounds and silanol compounds.

* * * * *